(12) United States Patent
Prata et al.

(10) Patent No.: US 9,562,239 B2
(45) Date of Patent: *Feb. 7, 2017

(54) PROCESSES OF PRODUCING A FERMENTATION PRODUCT

(71) Applicant: NOVOZYMES NORTH AMERICA, INC., Franklinton, NC (US)

(72) Inventors: Rogerio Prata, Franklinton, NC (US); Alison Robey, Sioux Falls, SD (US); Todd Forman, Franklinton, NC (US); Suzanne Clark, Franklinton, NC (US); Eder Manzini Bordin, Curitiba (BR)

(73) Assignee: NOVOZYMES NORTH AMERICA, INC., Bagsvaerd (DK)

(*) Notice: Subject to any disclaimer, the term of this patent is extended or adjusted under 35 U.S.C. 154(b) by 0 days.

This patent is subject to a terminal disclaimer.

(21) Appl. No.: 14/707,786

(22) Filed: May 8, 2015

(65) Prior Publication Data

US 2015/0240265 A1    Aug. 27, 2015

Related U.S. Application Data

(62) Division of application No. 13/988,103, filed as application No. PCT/US2011/060696 on Nov. 15, 2011, now Pat. No. 9,057,087.

(60) Provisional application No. 61/415,572, filed on Nov. 19, 2010.

(51) Int. Cl.
| | | |
|---|---|---|
| C12P 7/06 | (2006.01) | |
| C12P 19/14 | (2006.01) | |
| C12P 19/02 | (2006.01) | |

(52) U.S. Cl.
CPC ............ *C12P 7/06* (2013.01); *C12P 19/02* (2013.01); *C12P 19/14* (2013.01); *C12Y 104/03002* (2013.01); *C12Y 104/03003* (2013.01); *C12Y 302/01001* (2013.01); *C12Y 305/01001* (2013.01); *C12Y 305/01038* (2013.01); *C12Y 305/03001* (2013.01); *Y02E 50/17* (2013.01); *Y02P 20/52* (2015.11)

(58) Field of Classification Search
CPC ............ C12P 19/14; C12P 19/02; C12P 7/06; C12Y 305/1038; C12Y 305/03001
See application file for complete search history.

(56) References Cited

U.S. PATENT DOCUMENTS

2011/0296543 A1* 12/2011 Chang ............ C12Y 302/01004
800/13

FOREIGN PATENT DOCUMENTS

| WO | 2005/074716 A1 | 8/2005 |
| WO | 2010/022045 A1 | 2/2010 |
| WO | 2010/080408 A2 | 7/2010 |
| WO | 2012/018775 A1 | 2/2012 |

* cited by examiner

*Primary Examiner* — Maryam Monshipouri
(74) *Attorney, Agent, or Firm* — David A. Fazzolare

(57) ABSTRACT

The invention relates to a process of process of producing a fermentation product, comprising: liquefying a starch-containing material to dextrins with an alpha-amylase in the presence of an asparaginase and/or an amino acid oxidase; saccharifying the dextrins to a sugar with a glucoamylase; and fermenting the sugar using a fermenting organism.

18 Claims, No Drawings

SEQUENCE LISTING

```
<160> NUMBER OF SEQ ID NOS: 19

<210> SEQ ID NO 1
<211> LENGTH: 378
<212> TYPE: PRT
<213> ORGANISM: Aspergillus oryzae

<400> SEQUENCE: 1

Met Gly Val Asn Phe Lys Val Leu Ala Leu Ser Ala Leu Ala Thr Ile
 1               5                  10                  15

Ser His Ala Ser Pro Leu Leu Tyr Pro Arg Ala Thr Asp Ser Asn Val
             20                  25                  30

Thr Tyr Val Phe Thr Asn Pro Asn Gly Leu Asn Phe Thr Gln Met Asn
         35                  40                  45

Thr Thr Leu Pro Asn Val Thr Ile Phe Ala Thr Gly Thr Ile Ala
     50                  55                  60

Gly Ser Ser Ala Asp Asn Thr Ala Thr Gly Tyr Lys Ala Gly Ala
 65                  70                  75                  80

Val Gly Ile Gln Thr Leu Ile Asp Ala Val Pro Glu Met Leu Asn Val
                 85                  90                  95

Ala Asn Val Ala Gly Val Gln Val Thr Asn Val Gly Ser Pro Asp Ile
                100                 105                 110

Thr Ser Asp Ile Leu Leu Arg Leu Ser Lys Gln Ile Asn Glu Val Val
            115                 120                 125

Cys Asn Asp Pro Thr Met Ala Gly Ala Val Val Thr His Gly Thr Asp
        130                 135                 140

Thr Leu Glu Glu Ser Ala Phe Phe Leu Asp Ala Thr Val Asn Cys Arg
145                 150                 155                 160

Lys Pro Val Val Ile Val Gly Ala Met Arg Pro Ser Thr Ala Ile Ser
                165                 170                 175

Ala Asp Gly Pro Leu Asn Leu Leu Gln Ser Val Thr Val Ala Ala Ser
            180                 185                 190

Pro Lys Ala Arg Asp Arg Gly Ala Leu Ile Val Met Asn Asp Arg Ile
        195                 200                 205

Val Ser Ala Phe Tyr Ala Ser Lys Thr Asn Ala Asn Thr Val Asp Thr
    210                 215                 220

Phe Lys Ala Ile Glu Met Gly Asn Leu Gly Glu Val Val Ser Asn Lys
225                 230                 235                 240

Pro Tyr Phe Phe Tyr Pro Pro Val Lys Pro Thr Gly Lys Thr Glu Val
                245                 250                 255

Asp Ile Arg Asn Ile Thr Ser Ile Pro Arg Val Asp Ile Leu Tyr Ser
```

```
                260                 265                 270
Tyr Glu Asp Met His Asn Asp Thr Leu Tyr Ser Ala Ile Asp Asn Gly
                275                 280                 285
Ala Lys Gly Ile Val Ile Ala Gly Ser Gly Ser Val Ser Thr
        290                 295                 300
Pro Phe Ser Ala Ala Met Glu Asp Ile Thr Thr Lys His Asn Ile Pro
305                 310                 315                 320
Ile Val Ala Ser Thr Arg Thr Gly Asn Gly Glu Val Pro Ser Ser Ala
                325                 330                 335
Glu Ser Ser Gln Ile Ala Ser Gly Tyr Leu Asn Pro Ala Lys Ser Arg
            340                 345                 350
Val Leu Leu Gly Leu Leu Ala Gln Gly Lys Ser Ile Glu Glu Met
        355                 360                 365
Arg Ala Val Phe Glu Arg Ile Gly Val Ala
        370                 375

<210> SEQ ID NO 2
<211> LENGTH: 378
<212> TYPE: PRT
<213> ORGANISM: Aspergillus niger

<400> SEQUENCE: 2

Met Pro Leu Lys Pro Ile Leu Leu Ser Ala Leu Ala Ser Leu Ala Ser
1               5                   10                  15
Ala Ser Pro Leu Leu Tyr Ser Arg Thr Thr Asn Glu Thr Phe Val Phe
                20                  25                  30
Thr Asn Ala Asn Gly Leu Asn Phe Thr Gln Met Asn Thr Thr Leu Pro
            35                  40                  45
Asn Val Thr Ile Phe Ala Thr Gly Gly Thr Ile Ala Gly Ser Asp Ser
        50                  55                  60
Ser Ser Thr Ala Thr Thr Gly Tyr Thr Ser Gly Ala Val Gly Val Leu
65                  70                  75                  80
Ser Leu Ile Asp Ala Val Pro Ser Met Leu Asp Val Ala Asn Val Ala
                85                  90                  95
Gly Val Gln Val Ala Asn Val Gly Ser Glu Asp Ile Thr Ser Asp Ile
                100                 105                 110
Leu Ile Ser Met Ser Lys Lys Leu Asn Arg Val Val Cys Glu Asp Pro
            115                 120                 125
Thr Met Ala Gly Ala Val Ile Thr His Gly Thr Asp Thr Leu Glu Glu
        130                 135                 140
Thr Ala Phe Phe Leu Asp Ala Thr Val Asn Cys Gly Lys Pro Ile Val
145                 150                 155                 160
Ile Val Gly Ala Met Arg Pro Ser Thr Ala Ile Ser Ala Asp Gly Pro
                165                 170                 175
Phe Asn Leu Leu Glu Ala Val Thr Val Ala Ala Ser Thr Ser Ala Arg
            180                 185                 190
Asp Arg Gly Ala Met Val Val Met Asn Asp Arg Ile Ala Ser Ala Tyr
        195                 200                 205
Tyr Val Thr Lys Thr Asn Ala Asn Thr Met Asp Thr Phe Lys Ala Met
    210                 215                 220
Glu Met Gly Tyr Leu Gly Glu Met Ile Ser Asn Thr Pro Phe Phe Phe
225                 230                 235                 240
Tyr Pro Pro Val Lys Pro Thr Gly Lys Val Ala Phe Asp Ile Thr Asn
                245                 250                 255
```

```
Val Thr Glu Ile Pro Arg Val Asp Ile Leu Phe Ser Tyr Glu Asp Met
            260                 265                 270

His Asn Asp Thr Leu Tyr Asn Ala Ile Ser Ser Gly Ala Gln Gly Ile
        275                 280                 285

Val Ile Ala Gly Ala Gly Ala Gly Gly Val Thr Thr Ser Phe Asn Glu
    290                 295                 300

Ala Ile Glu Asp Val Ile Asn Arg Leu Glu Ile Pro Val Val Gln Ser
305                 310                 315                 320

Met Arg Thr Val Asn Gly Glu Val Pro Leu Ser Asp Val Ser Ser Asp
                325                 330                 335

Thr Ala Thr His Ile Ala Ser Gly Tyr Leu Asn Pro Gln Lys Ser Arg
            340                 345                 350

Ile Leu Leu Gly Leu Leu Leu Ser Gln Gly Lys Asn Ile Thr Glu Ile
        355                 360                 365

Ala Asp Val Phe Ala Leu Gly Thr Asp Ala
    370                 375

<210> SEQ ID NO 3
<211> LENGTH: 374
<212> TYPE: PRT
<213> ORGANISM: Aspergillus fumigatus

<400> SEQUENCE: 3

Met Thr Lys Leu Ser Phe Lys Ile Ile Thr Leu Ala Ala Met Ile Ala
1               5                   10                  15

Val Gly Asn Ala Ser Pro Phe Val Tyr Pro Arg Ala Thr Ser Pro Asn
            20                  25                  30

Ser Thr Tyr Val Phe Thr Asn Ser His Gly Leu Asn Phe Thr Gln Met
        35                  40                  45

Asn Thr Thr Leu Pro Asn Val Thr Ile Leu Ala Thr Gly Gly Thr Ile
    50                  55                  60

Ala Gly Ser Ser Asn Asp Asn Thr Ala Thr Thr Gly Tyr Thr Ala Gly
65                  70                  75                  80

Ala Ile Gly Ile Gln Gln Leu Met Asp Ala Val Pro Glu Met Leu Asp
                85                  90                  95

Val Ala Asn Val Ala Gly Ile Gln Val Ala Asn Val Gly Ser Pro Asp
            100                 105                 110

Val Thr Ser Ser Leu Leu Leu His Met Ala Arg Thr Ile Asn Glu Val
        115                 120                 125

Val Cys Asp Asp Pro Thr Met Ser Gly Ala Val Ile Thr His Gly Thr
    130                 135                 140

Asp Thr Leu Glu Glu Thr Ala Phe Phe Leu Asp Ala Thr Val Asn Cys
145                 150                 155                 160

Gly Lys Pro Ile Val Val Gly Ala Met Arg Pro Ala Thr Ala Ile
                165                 170                 175

Ser Ala Asp Gly Pro Phe Asn Leu Leu Gln Ala Val Thr Val Ala Ala
            180                 185                 190

His Pro Thr Ala Arg Asn Arg Gly Ala Leu Val Val Met Asn Asp Arg
        195                 200                 205

Ile Val Ser Ala Tyr Tyr Val Ser Lys Thr Asn Ala Asn Thr Met Asp
    210                 215                 220

Thr Phe Lys Ala Val Glu Met Gly Asn Leu Gly Ala Ile Ile Ser Asn
225                 230                 235                 240

Lys Pro Tyr Phe Phe Tyr Pro Pro Val Met Pro Thr Gly Lys Thr Thr
                245                 250                 255
```

```
Phe Asp Val Arg Asn Val Ala Ser Ile Pro Arg Val Asp Ile Leu Tyr
            260                 265                 270

Ser Tyr Gln Asp Met Gln Asn Asp Thr Leu Tyr Asp Ala Val Asp Asn
        275                 280                 285

Gly Ala Lys Gly Ile Val Arg Ser Val Ser Ser Gly Tyr Tyr Asp
290                 295                 300

Ala Ile Asp Asp Ile Ala Ser Thr His Ser Leu Pro Val Val Leu Ser
305                 310                 315                 320

Thr Arg Thr Gly Asn Gly Glu Val Ala Ile Thr Asp Ser Glu Thr Thr
                325                 330                 335

Ile Glu Ser Gly Phe Leu Asn Pro Gln Lys Ala Arg Ile Leu Leu Gly
            340                 345                 350

Leu Leu Leu Ala Glu Asp Lys Gly Phe Lys Glu Ile Lys Glu Ala Phe
        355                 360                 365

Ala Lys Asn Gly Val Ala
    370

<210> SEQ ID NO 4
<211> LENGTH: 378
<212> TYPE: PRT
<213> ORGANISM: Aspergillus nidulans

<400> SEQUENCE: 4

Met Gly Leu Arg Val Lys Ala Leu Ala Val Ala Ala Leu Ala Thr Leu
1               5                   10                  15

Ser Gln Ala Ser Pro Val Leu Tyr Thr Arg Glu Asp Thr Thr Ser Asn
            20                  25                  30

Thr Thr Tyr Ala Phe Thr Asn Ser Asn Gly Leu Asn Phe Thr Gln Met
        35                  40                  45

Asn Thr Thr Leu Pro Asn Val Thr Ile Phe Ala Thr Gly Gly Thr Ile
50                  55                  60

Ala Gly Ser Ala Ala Ser Asn Thr Ala Thr Thr Gly Tyr Gln Ala Gly
65                  70                  75                  80

Ala Leu Gly Ile Gln Thr Leu Ile Asp Ala Val Pro Glu Met Leu Ser
                85                  90                  95

Val Ala Asn Ile Ala Gly Val Gln Ile Ser Asn Val Gly Ser Pro Asp
            100                 105                 110

Val Thr Ser Thr Ile Leu Leu Glu Met Ala His Arg Leu Asn Lys Val
        115                 120                 125

Val Cys Glu Asp Pro Ser Met Ala Gly Ala Val Val Thr His Gly Thr
    130                 135                 140

Asp Thr Leu Glu Glu Thr Ala Phe Phe Leu Asp Ala Thr Val Asn Cys
145                 150                 155                 160

Gly Lys Pro Ile Val Ile Val Gly Ala Met Arg Pro Ala Thr Phe Ile
                165                 170                 175

Ser Ala Asp Gly Pro Tyr Asn Leu Leu Gln Ala Val Thr Val Ala Ser
            180                 185                 190

Thr Lys Glu Ala Arg Asn Arg Gly Ala Met Val Val Met Asn Asp Arg
        195                 200                 205

Ile Ala Ser Ala Tyr Tyr Val Ser Lys Thr Asn Ala Asn Thr Met Asp
    210                 215                 220

Thr Phe Lys Ala Val Glu Met Gly Tyr Leu Gly Ala Ile Ile Ser Asn
225                 230                 235                 240

Thr Pro Phe Phe Tyr Tyr Pro Ala Val Gln Pro Ser Gly Lys Thr Thr
```

```
                    245                 250                 255
Val Asp Val Ser Asn Val Thr Ser Ile Pro Arg Val Asp Ile Leu Tyr
            260                 265                 270

Ser Phe Gln Asp Met Thr Asn Asp Thr Leu Tyr Ser Ser Ile Glu Asn
            275                 280                 285

Gly Ala Lys Gly Val Val Ile Ala Gly Ser Gly Ala Gly Ser Val Asp
            290                 295                 300

Thr Ala Phe Ser Thr Ala Ile Asp Asp Ile Ile Ser Asn Gln Gly Val
305                 310                 315                 320

Pro Ile Val Gln Ser Thr Arg Thr Gly Asn Gly Glu Val Pro Tyr Ser
            325                 330                 335

Ala Glu Gly Gly Ile Ser Ser Gly Phe Leu Asn Pro Ala Lys Ser Arg
            340                 345                 350

Ile Leu Leu Gly Leu Leu Leu Ala Gln Gly Gly Lys Gly Thr Glu Glu
            355                 360                 365

Ile Arg Ala Val Phe Gly Lys Val Ala Val
370                 375

<210> SEQ ID NO 5
<211> LENGTH: 379
<212> TYPE: PRT
<213> ORGANISM: Penicillium citrinum
<220> FEATURE:
<221> NAME/KEY: misc_feature
<222> LOCATION: (110)..(110)
<223> OTHER INFORMATION: Xaa can be any naturally ocurring amino acid

<400> SEQUENCE: 5

Met Arg Leu Leu Phe Asn Thr Leu Ala Val Ser Ala Leu Ala Ala Thr
1               5                   10                  15

Ser Tyr Ala Ser Pro Ile Ile His Ser Arg Ala Ser Asn Thr Ser Tyr
            20                  25                  30

Thr Asn Ser Asn Gly Leu Lys Phe Asn His Phe Asp Ala Ser Leu Pro
        35                  40                  45

Asn Val Thr Leu Leu Ala Thr Gly Gly Thr Ile Ala Gly Thr Ser Asp
50                  55                  60

Asp Lys Thr Ala Thr Ala Gly Tyr Glu Ser Gly Ala Leu Gly Ile Asn
65                  70                  75                  80

Lys Ile Leu Ser Gly Ile Pro Glu Val Tyr Asp Ile Ala Asn Val Asn
            85                  90                  95

Ala Val Gln Phe Asp Asn Val Asn Ser Gly Asp Val Ser Xaa Ser Leu
            100                 105                 110

Leu Leu Asn Met Thr His Thr Leu Gln Lys Thr Val Cys Asp Asp Pro
        115                 120                 125

Thr Ile Ser Gly Ala Val Ile Thr His Gly Thr Asp Thr Leu Glu Glu
        130                 135                 140

Ser Ala Phe Phe Ile Asp Ala Thr Val Asn Cys Gly Lys Pro Ile Val
145                 150                 155                 160

Phe Val Gly Ser Met Arg Pro Ser Thr Ala Ile Ser Ala Asp Gly Pro
                165                 170                 175

Met Asn Leu Leu Gln Gly Val Thr Val Ala Ala Asp Lys Gln Ala Lys
            180                 185                 190

Asn Arg Gly Ala Leu Val Val Leu Asn Asp Arg Ile Val Ser Ala Phe
        195                 200                 205

Phe Ala Thr Lys Thr Asn Ala Asn Thr Met Asp Thr Phe Lys Ala Tyr
210                 215                 220
```

```
Glu Gln Gly Ser Leu Gly Met Ile Val Ser Asn Lys Pro Tyr Phe Tyr
225                 230                 235                 240

Tyr Pro Ala Val Glu Pro Asn Ala Lys His Val Val His Leu Asp Asp
                245                 250                 255

Val Asp Ala Ile Pro Arg Val Asp Ile Leu Tyr Ala Tyr Glu Asp Met
            260                 265                 270

His Ser Asp Ser Leu His Ser Ala Ile Lys Asn Gly Ala Lys Gly Ile
        275                 280                 285

Val Val Ala Gly Glu Gly Ala Gly Gly Ile Ser Thr Asp Phe Ser Asp
    290                 295                 300

Thr Ile Asp Glu Ile Ala Ser Lys His Gln Ile Pro Ile Ile Leu Ser
305                 310                 315                 320

His Arg Thr Val Asn Gly Glu Val Pro Thr Ala Asp Ile Thr Gly Asp
                325                 330                 335

Ser Ala Lys Thr Arg Ile Ala Ser Gly Met Tyr Asn Pro Gln Gln Ala
            340                 345                 350

Arg Val Leu Leu Gly Leu Leu Ala Glu Gly Lys Lys Phe Glu Asp
        355                 360                 365

Ile Arg Thr Ile Phe Gly Lys Ala Thr Val Ala
        370                 375

<210> SEQ ID NO 6
<211> LENGTH: 375
<212> TYPE: PRT
<213> ORGANISM: Aspergillus terreus

<400> SEQUENCE: 6

Met Gly Phe Asn Ile Lys Ala Leu Thr Val Ala Ala Leu Ala Ala Leu
1               5                   10                  15

Gly His Ala Ser Pro Leu Tyr Ser Arg Ala Asp Ala Asn Val Thr Tyr
            20                  25                  30

Val Phe Thr Asn Ala His Gly Leu Asn Phe Thr Gln Met Asn Thr Thr
        35                  40                  45

Leu Pro Asn Val Thr Ile Leu Ala Thr Gly Gly Thr Ile Ala Gly Ser
50                  55                  60

Ser Ala Asp Asn Thr Ala Thr Thr Gly Tyr Lys Ala Gly Ala Ile Gly
65                  70                  75                  80

Ile Gln Gln Leu Ile Asp Ala Val Pro Glu Met Leu Asn Val Ala Asn
                85                  90                  95

Val Ala Gly Val Gln Val Thr Asn Val Gly Ser Pro Val Thr Ser
            100                 105                 110

His Ile Leu Leu Asp Met Val Arg Met Leu Asp Glu Leu Val Cys Gln
        115                 120                 125

Asp Glu Thr Met Ala Gly Ala Val Ile Thr His Gly Thr Asp Thr Leu
130                 135                 140

Glu Glu Thr Ala Phe Phe Leu Asp Ala Thr Met Pro Cys Arg Lys Pro
145                 150                 155                 160

Val Val Val Val Gly Ala Met Arg Pro Ser Thr Ala Ile Ser Ala Asp
                165                 170                 175

Gly Pro Phe Asn Leu Leu Gln Ser Val Thr Val Ala Ala Thr Pro Ala
            180                 185                 190

Ala Arg Asp Arg Gly Ala Leu Val Val Leu Asn Asp Arg Val Leu Ser
        195                 200                 205

Ala Phe Tyr Thr Ser Lys Thr Asn Ala Asn Thr Met Asp Thr Phe Lys
```

```
              210                 215                 220
Ala Ile Glu Met Gly Ala Leu Ala Ala Ile Val Ser Asn Lys Pro Tyr
225                 230                 235                 240

Phe Tyr Tyr Pro Pro Val Arg Pro Thr Gly His Glu Phe Phe Asp Val
                245                 250                 255

Arg Asn Val Ser Ala Leu Pro Arg Val Asp Ile Leu Tyr Ser Tyr Gln
            260                 265                 270

Asp Met Gln Asn Asp Thr Leu Tyr Asp Ala Ala Lys Asn Gly Ala Lys
            275                 280                 285

Gly Ile Val Ile Ala Gly Ser Gly Ala Gly Ser Val Ser Ser Gly Phe
        290                 295                 300

Ser Ala Ala Ile Glu Asp Val Met Asp Thr Tyr His Ile Pro Val Val
305                 310                 315                 320

Ala Ser Thr Arg Thr Gly Asn Gly Glu Val Pro Pro Ser Asp Asp Gly
                325                 330                 335

Ala Ile Gly Ser Gly Phe Leu Asn Pro Gln Lys Ser Arg Ile Trp Leu
            340                 345                 350

Glu Leu Leu Leu Met Gln Lys Lys Thr Val Ala Glu Val Arg Glu Met
            355                 360                 365

Phe Ala Lys Val Ala Val Ala
370                 375

<210> SEQ ID NO 7
<211> LENGTH: 326
<212> TYPE: PRT
<213> ORGANISM: Pyrococcus furiosus

<400> SEQUENCE: 7

Met Lys Ile Leu Leu Ile Gly Met Gly Gly Thr Ile Ala Ser Val Lys
1               5                   10                  15

Gly Glu Asn Gly Tyr Glu Ala Ser Leu Ser Val Lys Glu Val Leu Asp
                20                  25                  30

Ile Ala Gly Ile Lys Asp Cys Glu Asp Cys Asp Phe Leu Asp Leu Lys
            35                  40                  45

Asn Val Asp Ser Thr Leu Ile Gln Pro Glu Asp Trp Val Asp Leu Ala
        50                  55                  60

Glu Thr Leu Tyr Lys Asn Val Lys Lys Tyr Asp Gly Ile Ile Val Thr
65                  70                  75                  80

His Gly Thr Asp Thr Leu Ala Tyr Thr Ser Ser Met Ile Ser Phe Met
                85                  90                  95

Leu Arg Asn Pro Pro Ile Pro Ile Val Phe Thr Gly Ser Met Ile Pro
            100                 105                 110

Ala Thr Glu Glu Asn Ser Asp Ala Pro Leu Asn Leu Gln Thr Ala Ile
        115                 120                 125

Lys Phe Ala Thr Ser Gly Ile Arg Gly Val Tyr Val Ala Phe Asn Gly
130                 135                 140

Lys Val Met Leu Gly Val Arg Thr Ser Lys Val Arg Thr Met Ser Arg
145                 150                 155                 160

Asp Ala Phe Glu Ser Ile Asn Tyr Pro Ile Ile Ala Glu Leu Arg Gly
                165                 170                 175

Glu Asp Leu Val Val Asn Phe Ile Pro Lys Phe Asn Asn Gly Glu Val
            180                 185                 190

Thr Leu Asp Leu Arg His Asp Pro Lys Val Leu Val Ile Lys Leu Ile
        195                 200                 205
```

```
Pro Gly Leu Ser Gly Asp Ile Phe Arg Ala Ala Val Glu Leu Gly Tyr
    210                 215                 220

Arg Gly Ile Val Ile Glu Gly Tyr Gly Ala Gly Gly Ile Pro Tyr Arg
225                 230                 235                 240

Gly Ser Asp Leu Leu Gln Thr Ile Glu Glu Leu Ser Lys Glu Ile Pro
                245                 250                 255

Ile Val Met Thr Thr Gln Ala Met Tyr Asp Gly Val Asp Leu Thr Arg
            260                 265                 270

Tyr Lys Val Gly Arg Leu Ala Leu Arg Ala Gly Val Ile Pro Ala Gly
        275                 280                 285

Asp Met Thr Lys Glu Ala Thr Val Thr Lys Leu Met Trp Ile Leu Gly
    290                 295                 300

His Thr Asn Asn Val Glu Glu Ile Lys Val Leu Met Arg Lys Asn Leu
305                 310                 315                 320

Val Gly Glu Leu Arg Asp
                325

<210> SEQ ID NO 8
<211> LENGTH: 119
<212> TYPE: PRT
<213> ORGANISM: Bothrops atrox
<400> SEQUENCE: 8

Ala Asp Asp Arg Asn Pro Leu Glu Glu Arg Lys Phe Asp Leu Gln Leu
1               5                   10                  15

Asn Arg Phe Ser Gln Glu Asn Glu Asn Ala Trp Tyr Phe Ile Lys Asn
            20                  25                  30

Arg Val Gly Glu Val Asn Lys Asp Pro Gly Val Leu Glu Tyr Pro Val
        35                  40                  45

Lys Pro Ser Glu Val Gly Lys Ser Ser Ala Gly Gln Leu Tyr Glu Glu
    50                  55                  60

Ser Leu Gln Lys Ala His Asp Asp Ile Phe Ala Tyr Glu Lys Ile Lys
65                  70                  75                  80

Phe Glu Pro Pro Leu Pro Pro Lys Lys Phe Trp Glu Asp Asp Gly Ile
                85                  90                  95

His Gly Gly Lys Ile Tyr Phe Ala Gly Glu Thr Ala Gln Ala His Gly
            100                 105                 110

Trp Ile Asp Ser Thr Ile Lys
        115

<210> SEQ ID NO 9
<211> LENGTH: 617
<212> TYPE: PRT
<213> ORGANISM: Trichoderma harzianum
<400> SEQUENCE: 9

Met Asp Asn Val Asp Phe Ala Glu Ser Val Arg Thr Arg Trp Ala Arg
1               5                   10                  15

Arg Leu Ile Arg Glu Lys Val Ala Lys Glu Leu Asn Ile Leu Thr Glu
            20                  25                  30

Arg Leu Gly Glu Val Pro Gly Ile Pro Pro Pro Asn Glu Gly Arg Phe
        35                  40                  45

Leu Gly Gly Gly Tyr Ser His Asp Asn Leu Pro Ser Asp Pro Leu Tyr
    50                  55                  60

Ser Ser Ile Lys Pro Ala Leu Leu Lys Glu Ala Pro Arg Ala Glu Glu
65                  70                  75                  80
```

```
Glu Leu Pro Pro Arg Lys Val Cys Ile Val Gly Ala Gly Val Ser Gly
                    85                  90                  95

Leu Tyr Ile Ala Met Ile Leu Asp Asp Leu Lys Ile Pro Asn Leu Thr
            100                 105                 110

Tyr Asp Ile Phe Glu Ser Ser Ser Arg Thr Gly Gly Arg Leu Tyr Thr
            115                 120                 125

His His Phe Thr Asp Ala Lys His Asp Tyr Tyr Asp Ile Gly Ala Met
        130                 135                 140

Arg Tyr Pro Asp Ile Pro Ser Met Lys Arg Thr Phe Asn Leu Phe Lys
145                 150                 155                 160

Arg Thr Lys Met Pro Leu Ile Lys Tyr Tyr Leu Asp Gly Glu Asn Thr
                165                 170                 175

Pro Gln Leu Tyr Asn Asn His Phe Phe Ala Lys Gly Val Ser Asp Pro
            180                 185                 190

Tyr Met Val Ser Val Ala Asn Gly Gly Thr Val Pro Asp Asp Val Val
            195                 200                 205

Asp Ser Val Gly Glu Lys Leu Gln Gln Ala Phe Gly Tyr Tyr Lys Glu
        210                 215                 220

Lys Leu Ala Glu Asp Phe Asp Lys Gly Phe Asp Glu Leu Met Leu Val
225                 230                 235                 240

Asp Asp Met Thr Thr Arg Glu Tyr Leu Lys Arg Gly Gly Pro Lys Gly
                245                 250                 255

Glu Ala Pro Lys Tyr Asp Phe Phe Ala Ile Gln Trp Met Glu Thr Gln
            260                 265                 270

Asn Thr Gly Thr Asn Leu Phe Asp Gln Ala Phe Ser Glu Ser Val Ile
            275                 280                 285

Asp Ser Phe Asp Phe Asp Asn Pro Thr Lys Pro Glu Trp Tyr Cys Ile
        290                 295                 300

Glu Gly Gly Thr Ser Leu Leu Val Asp Ala Met Glu Lys Thr Leu Val
305                 310                 315                 320

His Lys Val Gln Asn Asn Lys Arg Val Asp Ala Ile Ser Ile Asp Leu
                325                 330                 335

Asp Ala Pro Asp Asp Gly Asn Met Ser Val Arg Ile Gly Gly Lys Glu
            340                 345                 350

His Ser Gly Tyr Ser Thr Val Phe Asn Thr Thr Ala Leu Gly Cys Leu
        355                 360                 365

Asp Arg Met Asp Leu Arg Gly Leu Asn Leu His Pro Thr Gln Ala Asp
        370                 375                 380

Ala Ile Arg Cys Leu His Tyr Asp Asn Ser Thr Lys Val Ala Leu Lys
385                 390                 395                 400

Phe Ser Tyr Pro Trp Trp Ile Lys Asp Cys Gly Ile Thr Cys Gly Gly
                405                 410                 415

Ala Ala Ser Thr Asp Leu Pro Leu Arg Thr Cys Val Tyr Pro Ser Tyr
            420                 425                 430

Asn Leu Ala Asp Thr Gly Glu Ala Val Leu Leu Ala Ser Tyr Thr Trp
        435                 440                 445

Ser Gln Asp Ala Thr Arg Ile Gly Ser Leu Val Lys Glu Ala Pro Pro
        450                 455                 460

Gln Pro Pro Lys Glu Asp Glu Leu Val Glu Leu Ile Leu Gln Asn Leu
465                 470                 475                 480

Ala Arg Leu His Ala Glu His Met Thr Tyr Glu Lys Ile Lys Glu Ala
                485                 490                 495

Tyr Thr Gly Val Tyr His Ala Tyr Cys Trp Ala Asn Asp Pro Asn Val
```

```
            500             505             510
Gly Gly Ala Phe Ala Leu Phe Gly Pro Gly Gln Phe Ser Asn Leu Tyr
            515                 520                 525

Pro Tyr Leu Met Arg Pro Ala Gly Gly Lys Phe His Ile Val Gly
            530                 535                 540

Glu Ala Ser Ser Val His His Ala Trp Ile Ile Gly Ser Leu Glu Ser
545                 550                 555                 560

Ala Tyr Thr Ala Val Tyr Gln Phe Arg Tyr Lys Tyr Lys Met Trp Asp
                565                 570                 575

Tyr Leu Lys Leu Leu Leu Glu Arg Trp Gln Tyr Gly Leu Gln Glu Leu
            580                 585                 590

Glu Thr Gly Lys His Gly Thr Ala His Leu Gln Phe Ile Leu Gly Ser
                595                 600                 605

Leu Pro Lys Glu Tyr Gln Val Lys Ile
            610                 615

<210> SEQ ID NO 10
<211> LENGTH: 356
<212> TYPE: PRT
<213> ORGANISM: Trigonopsis variabilis

<400> SEQUENCE: 10

Met Ala Lys Ile Val Val Ile Gly Ala Gly Val Ala Gly Leu Thr Thr
1               5                   10                  15

Ala Leu Gln Leu Leu Arg Lys Gly His Glu Val Thr Ile Val Ser Glu
                20                  25                  30

Phe Thr Pro Gly Asp Leu Ser Ile Gly Tyr Thr Ser Pro Trp Ala Gly
            35                  40                  45

Ala Asn Trp Leu Thr Phe Tyr Asp Gly Gly Lys Leu Ala Asp Tyr Asp
50                  55                  60

Ala Val Ser Tyr Pro Ile Leu Arg Glu Leu Ala Arg Ser Ser Pro Glu
65                  70                  75                  80

Ala Gly Ile Arg Leu Ile Asn Gln Arg Ser His Val Leu Lys Arg Asp
                85                  90                  95

Leu Pro Lys Leu Glu Gly Ala Met Ser Ala Ile Cys Gln Arg Asn Pro
            100                 105                 110

Trp Phe Lys Asn Thr Val Asp Ser Phe Glu Ile Ile Glu Asp Arg Ser
            115                 120                 125

Arg Ile Val His Asp Asp Val Ala Tyr Leu Val Glu Phe Ala Ser Val
130                 135                 140

Cys Ile His Thr Gly Val Tyr Leu Asn Trp Leu Met Ser Gln Cys Leu
145                 150                 155                 160

Ser Leu Gly Ala Thr Val Val Lys Arg Arg Val Asn His Ile Lys Asp
                165                 170                 175

Ala Asn Phe Leu His Ser Ser Gly Ser Arg Pro Asp Val Ile Val Asn
            180                 185                 190

Cys Ser Gly Leu Phe Ala Arg Phe Leu Gly Gly Val Glu Asp Lys Lys
            195                 200                 205

Met Tyr Pro Ile Arg Gly Gln Val Val Leu Val Arg Asn Ser Leu Pro
210                 215                 220

Phe Met Ala Ser Phe Ser Ser Thr Pro Glu Lys Glu Asn Glu Asp Glu
225                 230                 235                 240

Ala Leu Tyr Ile Met Thr Arg Phe Asp Gly Thr Ser Ile Ile Gly Gly
                245                 250                 255
```

```
Cys Phe Gln Ser Asn Asn Trp Ser Ser Glu Pro Asp Pro Ser Leu Thr
                260                 265                 270

His Arg Ile Leu Ser Arg Ala Leu Asp Arg Phe Pro Glu Leu Thr Lys
            275                 280                 285

Asp Gly Pro Leu Asp Ile Val Arg Glu Cys Val Gly His Arg Pro Gly
290                 295                 300

Arg Glu Gly Gly Pro Arg Val Glu Leu Glu Lys Ile Pro Gly Val Gly
305                 310                 315                 320

Phe Val Val His Asn Tyr Gly Ala Ala Gly Ala Gly Tyr Gln Ser Ser
                325                 330                 335

Tyr Gly Met Ala Asp Glu Ala Val Ser Tyr Val Glu Arg Ala Leu Thr
            340                 345                 350

Arg Pro Asn Leu
            355

<210> SEQ ID NO 11
<211> LENGTH: 534
<212> TYPE: PRT
<213> ORGANISM: Rhodococcus opacus

<400> SEQUENCE: 11

Met Ala Phe Thr Arg Arg Ser Phe Met Lys Gly Leu Gly Ala Thr Gly
1               5                   10                  15

Gly Ala Gly Leu Ala Tyr Gly Ala Met Ser Thr Leu Gly Leu Ala Pro
            20                  25                  30

Ser Thr Ala Ala Pro Ala Arg Thr Phe Gln Pro Leu Ala Ala Gly Asp
        35                  40                  45

Leu Ile Gly Lys Val Lys Gly Ser His Ser Val Val Val Leu Gly Gly
50                  55                  60

Gly Pro Ala Gly Leu Cys Ser Ala Phe Glu Leu Gln Lys Ala Gly Tyr
65                  70                  75                  80

Lys Val Thr Val Leu Glu Ala Arg Thr Arg Pro Gly Gly Arg Val Trp
                85                  90                  95

Thr Ala Arg Gly Gly Ser Glu Glu Thr Asp Leu Ser Gly Glu Thr Gln
            100                 105                 110

Lys Cys Thr Phe Ser Glu Gly His Phe Tyr Asn Val Gly Ala Thr Arg
        115                 120                 125

Ile Pro Gln Ser His Ile Thr Leu Asp Tyr Cys Arg Glu Leu Gly Val
    130                 135                 140

Glu Ile Gln Gly Phe Gly Asn Gln Asn Ala Asn Thr Phe Val Asn Tyr
145                 150                 155                 160

Gln Ser Asp Thr Ser Leu Ser Gly Gln Ser Val Thr Tyr Arg Ala Ala
                165                 170                 175

Lys Ala Asp Thr Phe Gly Tyr Met Ser Glu Leu Leu Lys Lys Ala Thr
            180                 185                 190

Asp Gln Gly Ala Leu Asp Gln Val Leu Ser Arg Glu Asp Lys Asp Ala
        195                 200                 205

Leu Ser Glu Phe Leu Ser Asp Phe Gly Asp Leu Ser Asp Asp Gly Arg
    210                 215                 220

Tyr Leu Gly Ser Ser Arg Arg Gly Tyr Asp Ser Glu Pro Gly Ala Gly
225                 230                 235                 240

Leu Asn Phe Gly Thr Glu Lys Lys Pro Phe Ala Met Gln Glu Val Ile
                245                 250                 255

Arg Ser Gly Ile Gly Arg Asn Phe Ser Phe Asp Phe Gly Tyr Asp Gln
            260                 265                 270
```

Ala Met Met Met Phe Thr Pro Val Gly Gly Met Asp Arg Ile Tyr Tyr
            275                 280                 285

Ala Phe Gln Asp Arg Ile Gly Thr Asp Asn Ile Val Phe Gly Ala Glu
        290                 295                 300

Val Thr Ser Met Lys Asn Val Ser Glu Gly Val Thr Val Glu Tyr Thr
305                 310                 315                 320

Ala Gly Gly Ser Lys Lys Ser Ile Thr Ala Asp Tyr Ala Ile Cys Thr
                325                 330                 335

Ile Pro Pro His Leu Val Gly Arg Leu Gln Asn Asn Leu Pro Gly Asp
            340                 345                 350

Val Leu Thr Ala Leu Lys Ala Ala Lys Pro Ser Ser Gly Lys Leu
        355                 360                 365

Gly Ile Glu Tyr Ser Arg Arg Trp Trp Glu Thr Glu Asp Arg Ile Tyr
        370                 375                 380

Gly Gly Ala Ser Asn Thr Asp Lys Asp Ile Ser Gln Ile Met Phe Pro
385                 390                 395                 400

Tyr Asp His Tyr Asn Ser Asp Arg Gly Val Val Ala Tyr Tyr Ser
                405                 410                 415

Ser Gly Lys Arg Gln Glu Ala Phe Glu Ser Leu Thr His Arg Gln Arg
            420                 425                 430

Leu Ala Lys Ala Ile Ala Glu Gly Ser Glu Ile His Gly Glu Lys Tyr
        435                 440                 445

Thr Arg Asp Ile Ser Ser Ser Phe Ser Gly Ser Trp Arg Arg Thr Lys
    450                 455                 460

Tyr Ser Glu Ser Ala Trp Ala Asn Trp Ala Gly Ser Gly Gly Ser His
465                 470                 475                 480

Gly Gly Ala Ala Thr Pro Glu Tyr Glu Lys Leu Leu Glu Pro Val Asp
                485                 490                 495

Lys Ile Tyr Phe Ala Gly Asp His Leu Ser Asn Ala Ile Ala Trp Gln
            500                 505                 510

His Gly Ala Leu Thr Ser Ala Arg Asp Val Val Thr His Ile His Glu
        515                 520                 525

Arg Val Ala Gln Glu Ala
        530

<210> SEQ ID NO 12
<211> LENGTH: 685
<212> TYPE: PRT
<213> ORGANISM: Aspergillus nidulans

<400> SEQUENCE: 12

Met Arg Ser Phe Thr Phe Ser Leu Ser Leu Ser Leu Cys Leu Ala Leu
1               5                   10                  15

Ser Gln Ser Ala Val Ser Leu Thr Ile Asp Ser Gln Pro Ser Leu Leu
            20                  25                  30

Gln Phe Arg Thr Pro Lys Ile Thr Ala Asp Ser Leu His Asn Val Tyr
        35                  40                  45

Leu Asp Phe Ala Asp Ser Ser Phe Glu Gly Asp Leu His Ile Val Tyr
    50                  55                  60

Gly Asn Cys Glu Lys Ala Ser Val Asp Ser His His Ser Leu Gly
65                  70                  75                  80

Thr Leu Ser Ile Lys Arg Asp Ala Leu Pro Glu Arg Ile Val Trp Ile
                85                  90                  95

Thr Pro Pro Asp Ala Pro His Leu His Cys Leu His Ala Phe His Asn

```
              100                 105                 110
Glu Leu Gly Leu Ile Ala Arg Ser Glu Pro Ile Pro Val Thr Ser Pro
            115                 120                 125
Ile Val Arg Arg Glu Pro Leu Ala Ile Ala Asp Tyr Ala Asp Ala Met
            130                 135                 140
Gly Pro Trp Phe Asp Gly Val Ala Tyr Leu Ser Ala Gln Glu Pro Gly
145                 150                 155                 160
Lys Thr Ala Val Ala Ser Ala Lys Asn Ser Ser Ile Ala Ile Ile Gly
                165                 170                 175
Gly Gly Met Ser Gly Leu Met Thr Ser Leu Leu Ser Ser Val Gly
                180                 185                 190
Met His Asn Trp His Ile His Glu Ser Ser His Arg Ile Gly Gly Arg
        195                 200                 205
Ile Arg Thr Gln Tyr Leu Asn Asn Thr Arg Pro Asp Gln Tyr Gln Tyr
        210                 215                 220
Gln Glu Met Gly Pro Met Arg Phe Pro Val Ser Ile Thr Tyr Pro Glu
225                 230                 235                 240
Gln Asn Glu Thr Leu Glu Ile Gln Asp His Lys Met Val Phe Gln Leu
                245                 250                 255
Gly Arg Val Leu Thr Glu Met Asn Glu Lys Thr His Pro Glu Leu Arg
                260                 265                 270
Val Asp Phe Ile Pro Phe Ile Gln Asn Ser Asp Asn Val Pro Ala Ala
                275                 280                 285
Ala Gly Gly Asn Arg Leu Ser Asn Gly Arg Ile Pro Thr Ala Gly Glu
        290                 295                 300
Val Ala Ala Asp Pro Asp Leu Val Tyr Thr Ala Ala Gly Pro Asn Glu
305                 310                 315                 320
Thr Val Val Glu Glu Ala Glu Ala Ala Tyr Ser Ala Tyr Ile Asp His
                325                 330                 335
Asp Gly Leu Ser Ala Lys Lys Val Ala Asp Asn Ile Phe Arg Ala His
                340                 345                 350
Lys Thr Ala Val Glu His Gly Leu Phe His Trp Ser Glu Ala Gly Tyr
                355                 360                 365
Leu Arg Tyr Ala Leu Gly Tyr Ser Asp Asn Val Thr Asp Tyr Val Ala
        370                 375                 380
Gly Ser Gly Pro Glu Ser Pro Met Trp Gly Asp Ile Tyr Asp Asn Val
385                 390                 395                 400
Tyr Phe Ser Ala Thr Glu Phe Arg Thr Ile Asp Lys Gly Leu Glu Ser
                405                 410                 415
Phe Pro Arg Ala Phe Tyr Pro His Val Ala Asn Lys Thr Thr Phe Gly
                420                 425                 430
Arg Lys Ile Thr Gly Leu Lys Tyr Asn Gln Thr Thr Ser Lys Ile Ala
                435                 440                 445
Val Thr Trp Arg Asp Asp Pro Leu Ala Gln Val Pro Ser Ser Glu Asp
        450                 455                 460
Tyr Asp Tyr Ala Val Val Ala Ala Pro Phe Ser Lys Val Arg Leu Trp
465                 470                 475                 480
Asp Leu Pro Arg Tyr Ser Ser Leu Leu Ser Arg Ala Ile Asn Glu Met
                485                 490                 495
Asn Tyr Ser Pro Ser Cys Lys Leu Ser Leu Leu Tyr Glu Thr Arg Phe
                500                 505                 510
Trp Glu His Gln Ser Gln Asn Pro Ile Phe Gly Gly Cys Gly Ser Val
        515                 520                 525
```

```
Asp Val Pro Gly Val Gly Ser Val Cys Tyr Pro Ser Phe Asn Met Asn
    530                 535                 540

Gly Thr Gly Pro Gly Val Val Leu Ala Ser Tyr Ile Ser Gly Thr Gln
545                 550                 555                 560

Ala Arg Ser Val Gly Ala Leu Ser Asp Glu Asp Tyr Val Gly Ile Val
                565                 570                 575

Gln Arg Ala Met Val Glu Phe His Gly Pro Val Ala Ala Glu Gln Phe
            580                 585                 590

Thr Gly Ile Tyr Asn Arg Gln Cys Trp Glu Met Asp Glu His Gln Ala
        595                 600                 605

Gly Ala Trp Ala Ser Pro Leu Val Gly Gln Gln Asp Leu Phe Leu Pro
    610                 615                 620

Ala Tyr Tyr Asn Thr Glu Phe Lys Thr Ile Phe Ile Gly Glu His Thr
625                 630                 635                 640

Ser Tyr Thr His Ala Trp Ile Phe Ser Ala Leu Asp Ser Ala Val Arg
                645                 650                 655

Gly Thr Thr Gln Leu Leu Leu Asp Leu Gly Leu Val Asp Glu Ala Lys
            660                 665                 670

Gln Ile Val Glu Glu Trp Met Gly Arg Trp Ile Lys Leu
        675                 680                 685

<210> SEQ ID NO 13
<211> LENGTH: 391
<212> TYPE: PRT
<213> ORGANISM: Streptococcus oligofermentans

<400> SEQUENCE: 13

Met Asn His Phe Asp Thr Ile Ile Gly Gly Gly Pro Ala Gly Met
1               5                   10                  15

Met Ala Thr Ile Ser Ser Ser Phe Tyr Gly Gln Lys Thr Leu Leu Leu
                20                  25                  30

Glu Lys Asn Lys Arg Leu Gly Lys Lys Leu Ala Gly Thr Gly Gly Gly
            35                  40                  45

Arg Cys Asn Val Thr Asn Asn Gly Asn Leu Asp Asp Leu Met Ala Gly
50                  55                  60

Ile Pro Gly Asn Gly Arg Phe Leu Tyr Ser Val Phe Ser Gln Phe Asp
65                  70                  75                  80

Asn His Asp Ile Ile Asn Phe Phe Thr Glu Asn Gly Val Lys Leu Lys
                85                  90                  95

Val Glu Asp His Gly Arg Val Phe Pro Val Thr Asp Lys Ser Arg Thr
            100                 105                 110

Ile Ile Glu Ala Leu Glu Lys Lys Ile Ala Glu Leu Gly Gly Thr Val
        115                 120                 125

Ile Thr Asn Thr Glu Ile Val Ser Val Lys Lys Thr Asp Glu Leu Phe
    130                 135                 140

Thr Val Arg Ser Ser Asp Gln Ala Trp Thr Cys Gln Lys Leu Ile Val
145                 150                 155                 160

Thr Thr Gly Gly Lys Ser Tyr Pro Ser Thr Gly Ser Thr Gly Phe Gly
                165                 170                 175

His Asp Ile Ala Arg His Phe Lys His Thr Val Thr Asp Leu Glu Ala
            180                 185                 190

Ala Glu Ser Pro Leu Leu Thr Asp Phe Pro His Lys Ala Leu Gln Gly
        195                 200                 205

Ile Ser Leu Asp Asp Val Thr Leu Ser Tyr Gly Lys His Ile Ile Thr
```

```
            210                 215                 220
His Asp Leu Leu Phe Thr His Phe Gly Leu Ser Gly Pro Ala Ala Leu
225                 230                 235                 240

Arg Leu Ser Ser Phe Val Lys Gly Glu Thr Ile Tyr Leu Asp Val
                245                 250                 255

Leu Pro Gln Met Ser Gln Gln Asp Leu Ala Asp Phe Leu Glu His
                260                 265                 270

Arg Glu Lys Ser Leu Lys Asn Cys Leu Lys Ile Leu Leu Pro Glu Arg
                275                 280                 285

Ile Ala Asp Phe Phe Thr Gln Pro Phe Pro Glu Lys Val Lys Gln Leu
                290                 295                 300

Asn Leu Ser Glu Lys Glu Ala Leu Ile Lys Gln Ile Lys Glu Leu Pro
305                 310                 315                 320

Ile Ser Val Thr Gly Lys Met Ser Leu Ala Lys Ser Phe Val Thr Lys
                325                 330                 335

Gly Gly Val Ser Leu Lys Glu Ile Asn Pro Lys Thr Leu Glu Ser Lys
                340                 345                 350

Leu Val Pro Gly Leu His Phe Ala Gly Glu Val Leu Asp Ile Asn Ala
                355                 360                 365

His Thr Gly Gly Phe Asn Ile Thr Ser Ala Leu Cys Thr Gly Trp Val
                370                 375                 380

Ala Gly Ser Leu His Tyr Asp
385                 390

<210> SEQ ID NO 14
<211> LENGTH: 696
<212> TYPE: PRT
<213> ORGANISM: Neurospora crassa

<400> SEQUENCE: 14

Met Lys Trp Ser Ala Ala Gly Ala Ala Leu Leu Ala Leu Pro Ala
1               5                   10                  15

Asn Ser Ala Val Thr Ala Ser Leu Pro Leu Lys Leu Glu Thr Arg Ser
                20                  25                  30

Ser Leu Asn Ser Arg Leu Ser Asn Ile His Val Glu Arg Ser Ala Ser
                35                  40                  45

Val Glu Gly Ala Ile Ser Tyr Thr Tyr Gly Ser Cys Gln Ala Lys Arg
                50                  55                  60

Glu Glu Glu Ala His His Ser Ile Ser Gln Pro Thr Asp Ala His His
65                  70                  75                  80

Asp Arg Leu Val Trp Val Ile Pro Glu Asn Val Gln Ser Gly Gly Cys
                85                  90                  95

Ile Ser Ala Trp Ser Arg Ala Asn Gly Arg Leu Val Gly Arg Ser Arg
                100                 105                 110

Pro Gln Ser Phe Asp Phe Lys Ser Ile Lys Met Arg Arg Asp Leu Lys
                115                 120                 125

Ala Arg Ala Thr Lys Pro Ser Asp Ser Val Ala Ile His Met Thr Thr
                130                 135                 140

Asp Asn Gly Ile Asn Pro Trp Gly Pro Trp Phe Asp Gly Val Lys Leu
145                 150                 155                 160

Leu Glu Asp Lys Glu Ile Ser Thr Val Asp Val Glu Lys Ala Lys Ser
                165                 170                 175

Lys Asn Ile Ala Ile Val Gly Ala Gly Met Ser Gly Leu Met Thr Tyr
                180                 185                 190
```

-continued

```
Leu Cys Leu Thr Gln Ala Gly Met Thr Asn Val Ser Ile Glu Gly
            195                 200                 205
Gly Asn Arg Leu Gly Gly Arg Val His Thr Glu Tyr Leu Ser Gly Gly
210                 215                 220
Pro Phe Asp Tyr Ser Tyr Gln Glu Met Gly Pro Met Arg Phe Pro Asn
225                 230                 235                 240
Thr Ile Thr Leu Gly Asn Glu Thr Tyr Asn Val Ser Asp His Gln Leu
                245                 250                 255
Val Phe Gln Leu Ala Glu Glu Met Asn Ser Leu Asn Gly His Ser Lys
            260                 265                 270
Asn Leu Ser Val Asp Phe Ile Pro Trp Tyr Gln Ser Asn Ser Asn Gly
        275                 280                 285
Leu Tyr Tyr Tyr Asp Gly Ile Lys Asn Pro Glu Thr Gly Leu Pro Pro
    290                 295                 300
Thr Leu Ala Glu Leu Ala Ala Asn Ser Ser Leu Ala Leu Thr Arg Val
305                 310                 315                 320
Ser Asn Asn Ser Thr Lys Ser Leu Ser Gln Lys Val Asp Ala Phe Leu
                325                 330                 335
Pro Asp Thr Asp Lys Phe Phe Ala Glu Met Ala Gln Asn Met Phe Lys
            340                 345                 350
Ala His Ala Asp Trp Leu Ser Gly Gly Leu Ala Gly Leu Pro Gly Asp
        355                 360                 365
Gln Trp Ser Glu Phe Gly Phe Met Val Asn Tyr Leu Arg Gly Ser Leu
    370                 375                 380
Asn Asp Thr Ala Phe Leu Ser Ala Ser Ala His Ser Tyr Trp Asp Thr
385                 390                 395                 400
Leu Tyr Glu Gly Met Tyr Phe Ser Ala Ser Thr Trp Lys Thr Ile Asp
                405                 410                 415
Gly Gly Leu Asn Arg Leu Pro Leu Ser Phe His Pro Leu Val Asp Asn
            420                 425                 430
Ala Thr Thr Leu Asn Arg Arg Val Glu Arg Val Ala Phe Asp Ala Glu
        435                 440                 445
Thr Gln Lys Val Thr Leu His Ser Arg Asn Ser Tyr Lys Asp Ser Phe
    450                 455                 460
Glu Ser Ser Glu His Asp Tyr Ala Val Ile Ala Ala Pro Phe Ser Ile
465                 470                 475                 480
Val Lys Lys Trp Arg Phe Ser Pro Ala Leu Asp Leu Thr Ala Pro Thr
                485                 490                 495
Leu Ala Asn Ala Ile Gln Asn Leu Glu Tyr Thr Ser Ala Cys Lys Val
            500                 505                 510
Ala Leu Glu Phe Arg Thr Arg Phe Trp Glu His Leu Pro Gln Pro Ile
        515                 520                 525
Tyr Gly Ser Cys Ser Thr Thr Ser Asp Ile Pro Gly Ile Gly Ser Ile
    530                 535                 540
Cys Tyr Pro Ser Tyr Asn Ile Asn Gly Thr Asp Gly Pro Ala Ser Ile
545                 550                 555                 560
Leu Ala Ser Tyr Ile Ser Gly Ala Asp Trp Gly Asp Arg Trp Val Ser
                565                 570                 575
Thr Pro Glu Glu Glu His Val Gln Tyr Val Leu Asn Ala Met Ala Glu
            580                 585                 590
Ile His Gly Glu Glu Leu Val Lys Glu Gln Tyr Thr Gly Gln Phe Asn
        595                 600                 605
Arg Arg Cys Trp Ala Leu Asp Pro Leu Glu Ser Ala Ser Trp Ala Ser
```

```
    610                 615                 620

Pro Thr Val Gly Gln His Glu Leu Tyr Leu Pro Glu Tyr Phe Gln Thr
625                 630                 635                 640

Arg Asn Asn Leu Val Phe Val Gly Glu His Thr Ser Tyr Thr His Ala
                645                 650                 655

Trp Ile Ala Ser Ala Leu Glu Ser Gly Ile Arg Gly Ser Val Gln Leu
            660                 665                 670

Leu Leu Glu Leu Gly Leu Val Asp Glu Ala Lys Ala Thr Val Asp Lys
        675                 680                 685

Trp Met Ala Arg Trp Ile Asp Val
    690                 695

<210> SEQ ID NO 15
<211> LENGTH: 297
<212> TYPE: PRT
<213> ORGANISM: Bacillus cereus

<400> SEQUENCE: 15

Met Lys Lys Glu Ile Ser Val Ile Gly Val Pro Met Asp Leu Gly Gln
1               5                   10                  15

Met Arg Arg Gly Val Asp Met Gly Pro Ser Ala Ile Arg Tyr Ala Gly
            20                  25                  30

Val Ile Glu Arg Ile Glu Glu Ile Gly Tyr Asp Val Lys Asp Met Gly
        35                  40                  45

Asp Ile Cys Ile Glu Arg Glu Lys Glu Ile Asp Glu Asn Thr Lys Leu
    50                  55                  60

Arg Asn Leu Thr Gln Val Ala Thr Val Cys Asn Glu Leu Ala Ser Lys
65                  70                  75                  80

Val Asp His Ile Ile Glu Glu Gly Arg Phe Pro Leu Val Leu Gly Gly
                85                  90                  95

Asp His Ser Ile Ala Ile Gly Thr Leu Ala Gly Val Ala Lys His Tyr
            100                 105                 110

Lys Asn Leu Gly Val Ile Trp Tyr Asp Ala His Gly Asp Leu Asn Thr
        115                 120                 125

Glu Glu Thr Ser Pro Ser Gly Asn Ile His Gly Met Ser Leu Ala Ala
    130                 135                 140

Ser Leu Gly Tyr Gly His Ser Ser Leu Val Asp Leu Tyr Gly Ala Tyr
145                 150                 155                 160

Pro Lys Val Lys Lys Glu Asn Val Val Ile Ile Gly Ala Arg Ala Leu
                165                 170                 175

Asp Glu Gly Glu Lys Asp Phe Ile Arg Asn Glu Gly Ile Lys Val Phe
            180                 185                 190

Ser Met His Glu Ile Asp Arg Met Gly Met Thr Ala Val Met Glu Glu
        195                 200                 205

Thr Ile Ala Tyr Leu Ser His Thr Asp Gly Val His Leu Ser Leu Asp
    210                 215                 220

Leu Asp Gly Leu Asp Pro His Asp Ala Pro Gly Val Gly Thr Pro Val
225                 230                 235                 240

Ile Gly Gly Leu Ser Tyr Arg Glu Ser His Leu Ala Met Glu Met Leu
                245                 250                 255

Ala Glu Ala Asp Ile Ile Thr Ser Ala Glu Phe Val Glu Val Asn Thr
            260                 265                 270

Ile Leu Asp Glu Arg Asn Arg Thr Ala Thr Thr Ala Val Ala Leu Met
        275                 280                 285
```

```
Gly Ser Leu Phe Gly Glu Lys Leu Lys
    290                 295
```

```
<210> SEQ ID NO 16
<211> LENGTH: 338
<212> TYPE: PRT
<213> ORGANISM: Tomato

<400> SEQUENCE: 16
```

```
Met Arg Ser Ala Gly Arg Met Gly Ile His Tyr Met Gln Lys Leu His
1               5                   10                  15

Ala Ser Asn Val Pro Lys Glu Leu Val Glu Lys Gly Gln Asn Arg Val
            20                  25                  30

Ile Glu Ala Ser Leu Thr Leu Ile Arg Glu Arg Ala Lys Leu Lys Gly
        35                  40                  45

Glu Leu Val Arg Ala Leu Gly Gly Ala Val Ala Ser Thr Ser Leu Leu
    50                  55                  60

Gly Val Pro Leu Gly His Asn Ser Ser Phe Leu Gln Gly Pro Ala Phe
65                  70                  75                  80

Ala Pro Pro Arg Ile Arg Glu Ala Met Trp Cys Gly Ser Thr Asn Ser
                85                  90                  95

Thr Thr Glu Glu Gly Lys Glu Leu Asp Asp Pro Arg Ile Leu Thr Asp
            100                 105                 110

Val Gly Asp Val Pro Val Gln Glu Leu Arg Asp Ala Gly Val Asp Asp
        115                 120                 125

Asp Arg Leu Met Ser Ile Ile Ser Glu Ser Val Lys Leu Val Met Glu
    130                 135                 140

Glu Asn Pro Leu Arg Pro Leu Val Leu Gly Gly Asp His Ser Ile Ser
145                 150                 155                 160

Tyr Pro Val Val Arg Ala Val Ser Glu Lys Leu Gly Gly Pro Ile Asp
                165                 170                 175

Ile Leu His Leu Asp Ala His Pro Asp Ile Tyr His Ala Phe Glu Gly
            180                 185                 190

Asn Lys Tyr Ser His Ala Ser Ser Phe Ala Arg Ile Met Glu Gly Gly
    195                 200                 205

Tyr Ala Arg Arg Leu Leu Gln Val Gly Ile Arg Ser Ile Asn Lys Glu
210                 215                 220

Gly Arg Glu Gln Gly Lys Arg Phe Gly Val Glu Gln Tyr Glu Met Arg
225                 230                 235                 240

Thr Phe Ser Gln Asp Arg Gln Phe Leu Glu Asn Leu Lys Leu Gly Glu
                245                 250                 255

Gly Val Lys Gly Val Tyr Ile Ser Val Asp Val Asp Cys Met Asp Pro
            260                 265                 270

Ala Phe Ala Pro Gly Val Ser His Ile Glu Pro Gly Gly Leu Ser Phe
    275                 280                 285

Arg Asp Val Leu Asn Ile Leu His Asn Leu Gln Ala Asp Val Val Gly
290                 295                 300

Ala Asp Val Val Glu Phe Asn Pro Gln Arg Asp Thr Val Asp Gly Met
305                 310                 315                 320

Thr Ala Met Val Ala Ala Lys Leu Val Arg Glu Leu Thr Ala Lys Ile
                325                 330                 335

Ser Lys
```

```
<210> SEQ ID NO 17
<211> LENGTH: 311
```

<212> TYPE: PRT
<213> ORGANISM: Mushroom

<400> SEQUENCE: 17

```
Met Pro Ser Leu Gln Phe Leu Pro Gln Pro Leu Thr Ala Ala Ile Val
1               5                   10                  15

Gly Cys Pro Phe Ser Gly Gly Gln Arg Arg Thr Gly Val Asp Gln Gly
            20                  25                  30

Pro Ile Arg Leu Val Glu Ala Gly Leu Val Glu Gln Leu Lys Gly Leu
        35                  40                  45

Gly Trp Asn Val Val Phe Asp Gly His His Gln Phe Glu Glu Tyr Asn
    50                  55                  60

Asn Leu Asp Asp Ala Pro Ile Gly Ile Met Lys Asn Pro Arg Thr Val
65                  70                  75                  80

Ser Gln Val Asn Arg Ser Val Ala Gly Val Val Met Asn His Ala Lys
                85                  90                  95

Asn Gly Met Leu Pro Val Thr Leu Gly Gly Asp His Ser Leu Ala Met
            100                 105                 110

Gly Thr Ile Ser Gly Ser Leu Ala Val His Pro Asp Ala Cys Val Ile
        115                 120                 125

Trp Ile Asp Ala His Ala Asp Ile Asn Thr Ile Glu Thr Thr Asp Ser
    130                 135                 140

Gly Asn Met His Gly Met Pro Leu Ser Phe Leu Leu Gly Ile Gly Asp
145                 150                 155                 160

Lys Ile Gln Glu Phe Asp Trp Ile Lys Pro Val Leu Lys Pro Glu Arg
                165                 170                 175

Leu Val Tyr Ile Gly Leu Arg Asp Leu Asp Ala Gly Glu Lys Arg Leu
            180                 185                 190

Leu Arg Glu His Asn Ile Lys Ala Phe Ser Met His Glu Val Asp Lys
        195                 200                 205

Tyr Gly Ile Gly Lys Val Val Glu Met Ala Leu Asp Tyr Val Asn Pro
    210                 215                 220

Lys Arg Asp Leu Pro Ile His Leu Ser Phe Asp Val Asp Ala Leu Asp
225                 230                 235                 240

Pro Ser Val Ala Pro Ser Thr Gly Thr Pro Val Arg Gly Gly Leu Thr
                245                 250                 255

Phe Arg Glu Gly His Tyr Ile Cys Glu Ala Ile His Gly Thr Gly Leu
            260                 265                 270

Leu Val Ser Leu Asp Leu Met Glu Val Asn Pro Ser Leu Ala Glu Ala
        275                 280                 285

Ala Asp Ala Asp Lys Thr Val Ala Val Gly Cys Ser Leu Val Arg Ala
    290                 295                 300

Ala Leu Gly Glu Thr Leu Leu
305                 310
```

<210> SEQ ID NO 18
<211> LENGTH: 322
<212> TYPE: PRT
<213> ORGANISM: Pig

<400> SEQUENCE: 18

```
Met Ser Phe Lys Ser Gln Ser Ile Gly Ile Ile Gly Ala Pro Phe Ser
1               5                   10                  15

Lys Gly Gln Pro Arg Gly Val Glu Glu Gly Pro Thr Ala Leu Arg
            20                  25                  30
```

```
Lys Ala Gly Leu Leu Glu Lys Leu Glu Gln Glu Cys Asp Val Lys
            35                  40                  45
Asp Tyr Gly Asp Leu Cys Phe Ala Asp Val Pro Asn Asp Thr Pro Phe
 50                      55                  60
Gln Ile Val Lys Asn Pro Arg Ser Val Gly Lys Ala Asn Gln Gln Leu
 65                  70                  75                  80
Ala Asp Val Val Ala Glu Ile Lys Lys Asn Gly Arg Thr Ser Leu Val
                 85                  90                  95
Leu Gly Gly Asp His Ser Met Ala Ile Gly Ser Ile Ser Gly His Ala
                100                 105                 110
Arg Val His Pro Asp Leu Cys Val Ile Trp Val Asp Ala His Thr Asp
            115                 120                 125
Ile Asn Thr Pro Leu Thr Thr Thr Thr Gly Asn Leu His Gly Gln Pro
130                 135                 140
Val Ser Phe Leu Leu Lys Glu Leu Lys Glu Lys Ile Pro Glu Val Pro
145                 150                 155                 160
Gly Leu Ser Trp Val Thr Pro Cys Leu Ser Ala Lys Asp Ile Val Tyr
                165                 170                 175
Ile Gly Leu Arg Asp Val Asp Pro Ala Glu His Tyr Ile Leu Lys Thr
            180                 185                 190
Leu Gly Ile Lys Tyr Phe Ser Met Ile Glu Val Asp Lys Leu Gly Ile
            195                 200                 205
Gly Lys Val Met Glu Glu Ala Phe Ser Tyr Leu Leu Gly Arg Lys Lys
        210                 215                 220
Arg Pro Ile His Leu Ser Phe Asp Val Asp Gly Leu Asp Pro Phe Phe
225                 230                 235                 240
Thr Pro Ala Thr Gly Thr Pro Val His Gly Gly Leu Ser Tyr Arg Glu
                245                 250                 255
Gly Ile Tyr Ile Thr Glu Glu Ile Tyr Lys Thr Gly Leu Leu Ser Gly
            260                 265                 270
Leu Asp Ile Met Glu Val Asn Pro Ser Leu Gly Lys Thr Pro Glu Glu
            275                 280                 285
Val Thr Arg Thr Val Asn Thr Ala Val Ala Leu Val Leu Ala Cys Phe
290                 295                 300
Gly Val Ala Arg Glu Gly Asn His Lys Pro Ile Asp Tyr Leu Lys Pro
305                 310                 315                 320
Pro Lys

<210> SEQ ID NO 19
<211> LENGTH: 299
<212> TYPE: PRT
<213> ORGANISM: Unknown
<220> FEATURE:
<223> OTHER INFORMATION: Synthetic construct

<400> SEQUENCE: 19

Met Lys Pro Ile Ser Ile Ile Gly Val Pro Met Asp Leu Gly Gln Thr
 1               5                  10                  15
Arg Arg Gly Val Asp Met Gly Pro Ser Ala Met Arg Tyr Ala Gly Ile
                20                  25                  30
Ile Glu Arg Leu Glu Arg Leu His Tyr Asp Ile Glu Asp Leu Gly Asp
            35                  40                  45
Ile Pro Ile Gly Lys Ala Glu Arg Leu His Glu Gln Gly Asp Ser Arg
 50                  55                  60
Leu Arg Asn Leu Lys Ala Val Ala Glu Ala Asn Glu Lys Leu Ala Thr
```

-continued

```
            65                  70                  75                  80
Ala Val Asp Gln Val Val Gln Arg Gly Arg Phe Pro Leu Val Leu Gly
                85                      90                  95

Gly Asp His Ser Ile Ala Ile Gly Thr Ile Ala Gly Val Ala Lys His
                100                     105                 110

Tyr Glu Arg Leu Gly Val Ile Trp Tyr Asp Ala His Gly Asp Val Asn
            115                     120                 125

Thr Glu Glu Thr Ser Pro Ser Gly Asn Ile His Gly Met Pro Leu Ala
            130                     135                 140

Ala Ser Leu Gly Phe Gly His Pro Ala Leu Thr Gln Ile Gly Gly Tyr
145                     150                     155                 160

Ser Pro Lys Ile Lys Pro Glu His Val Val Leu Ile Gly Val Arg Ser
                165                     170                 175

Leu Asp Glu Gly Glu Lys Lys Phe Ile Arg Glu Lys Gly Ile Lys Ile
            180                     185                 190

Tyr Thr Met His Glu Val Asp Arg Leu Gly Met Thr Arg Val Met Glu
            195                     200                 205

Glu Thr Ile Thr Tyr Leu Lys Glu Arg Thr Asp Gly Val His Leu Ser
            210                     215                 220

Leu Asp Leu Asp Gly Leu Asp Pro Ser Asp Ala Pro Gly Val Gly Thr
225                     230                     235                 240

Pro Val Ile Gly Gly Leu Thr Tyr Arg Glu Ser His Leu Ala Met Glu
                245                     250                 255

Met Leu Ala Glu Ala Gln Ile Ile Thr Ser Ala Glu Phe Val Glu Val
                260                     265                 270

Asn Pro Ile Leu Asp Glu Arg Asn Lys Thr Ala Ser Val Ala Val Ala
            275                     280                 285

Leu Met Gly Ser Leu Phe Gly Glu Lys Leu Ile
            290                     295
```

PROCESSES OF PRODUCING A FERMENTATION PRODUCT

CROSS-REFERENCE TO RELATED APPLICATIONS

This application is a divisional of U.S. application Ser. No. 13/988,103 filed Aug. 27, 2013, now allowed, which is a 35 U.S.C. 371 national application of PCT/US2011/060696 filed Nov. 15, 2011, which claims priority or the benefit under 35 U.S.C. 119 of U.S. provisional application No. 61/415,572 filed Nov. 19, 2010, the contents of which are fully incorporated herein by reference.

FIELD OF THE INVENTION

The present invention relates to methods of producing a fermentation product from plant material using one or more fermenting organisms; compositions; transgenic plants; and modified fermenting organisms, that can be used in methods and/or processes of the invention.

BACKGROUND OF THE INVENTION

A vast number of commercial products that are difficult to produce synthetically are today produced by fermenting organisms. Such products include alcohols (e.g., butanol, ethanol, methanol, 1,3-propanediol); organic acids (e.g., acetic acid, citric acid, gluconate, gluconic acid, itaconic acid, lactic acid, succinic acid, 2,5-diketo-D-gluconic acid); ketones (e.g., acetone); amino acids (e.g., glutamic acid); gases (e.g., $H_2$ and $CO_2$), and more complex compounds, including, for example, antibiotics (e.g., penicillin and tetracycline); enzymes; vitamins (e.g., riboflavin, $B_{12}$, beta-carotene); and hormones. Fermentation is also commonly used in the consumable alcohol (e.g., beer and wine), dairy (e.g., in the production of yogurt and cheese), leather, and tobacco industries.

A vast number of processes of producing fermentation products, such as ethanol, by fermentation of sugars provided by degradation of starch-containing materials are known in the art.

However, production of fermentation products, such as ethanol, from such plant materials is still too costly. Therefore, there is a need for providing processes that can increase the yield of the fermentation product and thereby reduce the production costs.

It is an object of the present invention to provide an improved process for producing a fermentation product.

SUMMARY OF THE INVENTION

The present invention relates to a process of producing a fermentation product, comprising:
(a) liquefying a starch-containing material to a dextrin with an alpha-amylase in the presence of an amino acid oxidase, an arginase, and/or an asparaginase;
(b) saccharifying the dextrin to a sugar with a saccharifying enzyme; and
(c) fermenting the sugar using a fermenting organism to produce the fermentation product.

The present invention also relates to a process of producing a sugar, comprising:
(a) liquefying a starch-containing material to a dextrin with an alpha-amylase in the presence of an amino acid oxidase, an arginase, and/or an asparaginase; and
(b) saccharifying the dextrin to a sugar with a saccharifying enzyme.

The present invention also relates to a process of producing a fermentation product, comprising:
(a) treating a starch-containing material with an amino acid oxidase, an arginase, and/or an asparaginase;
(b) liquefying the treated starch-containing material to a dextrin with an alpha-amylase;
(c) saccharifying the dextrin to a sugar with a saccharifying enzyme; and
(d) fermenting the sugar using a fermenting organism to produce the fermentation product.

The present invention also relates to a process of producing a dextrin, comprising
(a) liquefying a starch-containing material to the dextrin with an alpha-amylase in the presence of an amino acid oxidase, an arginase, and/or an asparaginase; and
(b) recovering the dextrin.

The present invention also relates to a process of producing a fermentation product, comprising:
(a) treating a starch-containing material with an amino acid oxidase, an arginase, and/or an asparaginase;
(b) liquefying the treated starch-containing material to a dextrin with an alpha-amylase;
(c) saccharifying the dextrin to a sugar with a saccharifying enzyme; and
(d) fermenting the sugar using a fermenting organism to produce the fermentation product.

The present invention also relates to a process of producing a sugar, comprising:
(a) treating a starch-containing material with an amino acid oxidase, an arginase, and/or an asparaginase;
(b) liquefying the treated starch-containing material to a dextrin with an alpha-amylase; and
(c) saccharifying the dextrin to a sugar with a saccharifying enzyme.

The present invention also relates to a process of producing a dextrin, comprising:
(a) treating a starch-containing material with an amino acid oxidase, an arginase, and/or an asparaginase; and
(b) liquefying the treated starch-containing material to a dextrin with an alpha-amylase.

The present invention also relates to a process of producing a fermentation product, comprising converting a starch-containing material to a dextrin with an alpha-amylase; saccharifying the dextrin to a sugar with a glucoamylase; and fermenting the sugar using a fermenting organism in the presence of an amino acid oxidase, an arginase, and/or an asparaginase in a single step at a temperature below the initial gelatinization temperature of the starch-containing material.

The present invention also relates to a process of producing a fermentation product, comprising
(a) treating a plant extract containing amino acid(s) and soluble sugar(s) with an amino acid oxidase, an arginase, and/or an asparaginase;
(b) producing molasses from the plant extract;
(c) diluting the molasses; and
(d) fermenting the diluted molasses with a fermenting organism to produce ethanol.

The present invention also relates to a process of producing a fermentation product, comprising
(a) treating a plant extract containing amino acid(s) and soluble sugar(s) with an amino acid oxidase, an arginase, and/or an asparaginase; and
(b) fermenting the treated plant extract with a fermenting organism to produce the fermentation product.

The present invention also relates to a process of producing a sugar, comprising
(a) treating a plant extract containing amino acid(s) and soluble sugar(s) with an amino acid oxidase, an arginase, and/or an asparaginase; and
(b) recovering the sugar from the treated plant extract.

The present invention also relates to a process of producing sucrose, comprising:
(a) treating a plant extract containing amino acid(s) and soluble sugar(s) with an amino acid oxidase, an arginase, and/or an asparaginase;
(b) clarification of the plant extract;
(c) concentration of sugars found in the clarified plant extract (e.g., by evaporation) to form a syrup containing sucrose;
(d) crystallization of sucrose from the syrup; and
(e) recovering sucrose.

The present invention also relates to a composition comprising (a) an asparaginase, an arginase, and/or amino acid oxidase, (b) a glucoamylase and (c) an alpha-amylase.

DETAILED DESCRIPTION OF THE INVENTION

Definitions

Alpha-amylases (alpha-1,4-glucan-4-glucanohydrolases, EC 3.2.1.1) are a group of enzymes, which catalyze the hydrolysis of starch and other linear and branched 1,4-glucosidic oligo- and polysaccharides.

Amino acid oxidases (L-amino acid oxidase, EC 1.4.3.2 and D-amino acid oxidase, EC1.4.3.3) are a group of enzymes which catalyze the following reaction:

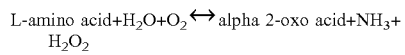
L-amino acid+$H_2O$+$O_2$ ↔ alpha 2-oxo acid+$NH_3$+ $H_2O_2$

Arginases (L-Arginine aminohydrolase, EC 3.5.3.1) are a group of enzymes which catalyze the following reaction:

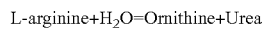
L-arginine+$H_2O$=Ornithine+Urea

Asparaginases are enzymes of EC 3.5.1.1 (asparaginase or L-asparagine amidohydrolase) and EC 3.5.1.38 (glutamin-asparaginase or glutaminase-asparaginase), which catalyze the following reaction:

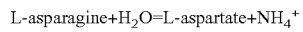
L-asparagine+$H_2O$=L-aspartate+$NH_4^+$

Fragment: The term "fragment" means a polypeptide having one or more (several) amino acids deleted from the amino and/or carboxyl terminus of a mature polypeptide; wherein the fragment has enzyme activity.

Glucoamylases (glucan 1,4-α-glucosidase, EC 3.2.1.3) are a group of enzymes, which catalyze the hydrolysis of terminal (1→4)-linked α-D-glucose residues successively from non-reducing ends of the chains with release of β-D-glucose.

Isolated: The terms "isolated" and "purified" mean a polypeptide or polynucleotide that is removed from at least one component with which it is naturally associated. For example, a polypeptide or variant may be at least 1% pure, e.g., at least 5% pure, at least 10% pure, at least 20% pure, at least 40% pure, at least 60% pure, at least 80% pure, and at least 90% pure, as determined by SDS-PAGE and a polynucleotide may be at least 1% pure, e.g., at least 5% pure, at least 10% pure, at least 20% pure, at least 40% pure, at least 60% pure, at least 80% pure, at least 90% pure, and at least 95% pure, as determined by agarose electrophoresis.

Mature polypeptide: The term "mature polypeptide" means a polypeptide in its final form following translation and any post-translational modifications, such as N-terminal processing, C-terminal truncation, glycosylation, phosphorylation, etc.

Parent Enzyme: The term "parent" means an enzyme to which an alteration is made to produce a variant. The parent may be a naturally occurring (wild-type) polypeptide or a variant thereof.

Sequence Identity: The relatedness between two amino acid sequences or between two nucleotide sequences is described by the parameter "sequence identity".

For purposes of the present invention, the degree of sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−Total Number of Gaps in Alignment)

For purposes of the present invention, the degree of sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of Alignment−Total Number of Gaps in Alignment)

Variant: The term "variant" means a polypeptide comprising an alteration, i.e., a substitution, insertion, and/or deletion, at one or more (several) positions. A substitution means a replacement of an amino acid occupying a position with a different amino acid; a deletion means removal of an amino acid occupying a position; and an insertion means adding 1-5 amino acids adjacent to an amino acid occupying a position.

Wild-Type Enzyme: The term "wild-type" enzyme means an enzyme expressed by a naturally occurring microorganism, such as a bacterium, yeast, or filamentous fungus found in nature.

Processes for Producing Fermentation Products, Dextrins, and Sugars from Starch-Containing Materials The present invention relates to a process of producing a fermentation product, comprising:
(a) liquefying a starch-containing material to a dextrin with an alpha-amylase in the presence of an amino acid oxidase, an arginase, and/or an asparaginase;
(b) saccharifying the dextrin to a sugar with a saccharifying enzyme; and
(c) fermenting the sugar using a fermenting organism to produce the fermentation product.

The present invention also relates to a process of producing a sugar, comprising:

(a) liquefying a starch-containing material to a dextrin with an alpha-amylase in the presence of an amino acid oxidase, an arginase, and/or an asparaginase; and (b) saccharifying the dextrin to a sugar with a saccharifying enzyme.

The present invention also relates to a process of producing a dextrin, comprising (a) liquefying a starch-containing material to the dextrin with an alpha-amylase in the presence of an amino acid oxidase, an arginase, and/or an asparaginase; and (b) recovering the dextrin.

The present invention also relates to a process of producing a fermentation product, comprising:

(a) treating a starch-containing material with an amino acid oxidase, an arginase, and/or an asparaginase;

(b) liquefying the treated starch-containing material to a dextrin with an alpha-amylase;

(c) saccharifying the dextrin to a sugar with a saccharifying enzyme; and (d) fermenting the sugar using a fermenting organism to produce the fermentation product.

The present invention also relates to a process of producing a sugar, comprising:

(a) treating a starch-containing material with an amino acid oxidase, an arginase, and/or an asparaginase;

(b) liquefying the treated starch-containing material to a dextrin with an alpha-amylase; and (c) saccharifying the dextrin to a sugar with a saccharifying enzyme.

The present invention also relates to a process of producing a dextrin, comprising:

(a) treating a starch-containing material with an amino acid oxidase, an arginase, and/or an asparaginase; and (b) liquefying the treated starch-containing material to a dextrin with an alpha-amylase.

Starch is formed within plant cells as tiny granules insoluble in water. When put in cold water, the starch granules may absorb a small amount of the liquid and swell. At temperatures up to 50° C. to 75° C. the swelling may be reversible. However, with higher temperatures an irreversible swelling called "gelatinization" begins. Granular starch to be processed may be a highly refined starch quality, preferably at least 90%, at least 95%, at least 97% or at least 99.5% pure or it may be a more crude starch-containing materials comprising (e.g., milled) whole grains including non-starch fractions such as germ residues and fibers. The raw material, such as whole grains, may be reduced in particle size, e.g., by milling, in order to open up the structure and allowing for further processing. Two processes are preferred according to the invention: wet and dry milling. In dry milling whole kernels are milled and used. Wet milling gives a good separation of germ and meal (starch granules and protein) and is often applied at locations where the starch hydrolyzate is used in the production of, e.g., syrups. Both dry and wet milling are well known in the art of starch processing and may be used in a process of the invention. In an embodiment the particle size is reduced to between 0.05-3.0 mm, preferably 0.1-0.5 mm, or so that at least 30%, preferably at least 50%, more preferably at least 70%, even more preferably at least 90% of the starch-containing material fits through a sieve with a 0.05-3.0 mm screen, preferably 0.1-0.5 mm screen.

The starch-containing material may be used to produce a sugar, a dextrin, or a fermentation product. Generally, the sugar-containing material is liquefied to a dextrin with an alpha-amylase, which is then followed by saccharification (a process which converts the dextrin to a sugar) and fermentation (a process which converts the sugar to a fermentation product).

In an embodiment, the starch-containing material is treated with an amino acid oxidase, an arginase, and/or an asparaginase prior to liquefaction. This treatment may be carried out at any pH and temperature suitable for enzyme activity for a period of time to allow for the enzymatic reaction to take place. In an embodiment, the temperature is in the range of 20-75° C., e.g., 20-65° C. or 40-60° C.; the pH is in the range of 4.5-6.5; and the period of time is in the range of 5 minutes-2 hours, e.g., 5 minutes-1 hour.

In an embodiment, an asparaginase is added to the starch-containing material prior to liquefaction. In another embodiment, an arginase is added to the starch-containing material prior to liquefaction. In another embodiment, an amino acid oxidase is added to the starch-containing material prior to liquefaction. In another embodiment, an asparaginase, an arginase, and an amino acid oxidase are added to the starch-containing material prior to liquefaction.

An asparaginase and/or an amino acid oxidase also may be added during liquefaction. In an embodiment, an asparaginase is added during liquefaction. In another embodiment, an arginase is added during liquefaction. In another embodiment, an amino acid oxidase is added during liquefaction. In another embodiment, an asparaginase, an arginase, and an amino acid oxidase are present during liquefaction.

Liquefaction is carried out in the presence of an alpha-amylase, preferably a bacterial alpha-amylase and/or acid fungal alpha-amylase. In an embodiment, a phytase is also present during liquefaction.

During a typical liquefaction, the long-chained starch is degraded into branched and linear shorter units (maltodextrins) by an alpha-amylase. Liquefaction may be carried out as a three-step hot slurry process. The slurry is heated to between 60-95° C. (e.g., 77-86° C., 80-85° C., or 83-85° C.) and an alpha-amylase(s) is (are) added to initiate liquefaction (thinning). The liquefaction process is carried out at 85° C. for 1-2 hours. The pH is generally between 5.5 and 6.2. In order to ensure optimal enzyme stability under these conditions, 1 mM of calcium is optionally added (to provide about 40 ppm free calcium ions). After such treatment, the liquefied starch will have a "dextrose equivalent" (DE) of 10-15.

The slurry may be subsequently jet-cooked at between 95-140° C., e.g., 105-125° C., for about 1-15 minutes, e.g., about 3-10 minutes, especially around 5 minutes. The slurry is then cooled to 60-95° C. and more alpha-amylase(s) is (are) added to obtain the final hydrolysis (secondary liquefaction). The jet-cooking process is carried out at pH 4.5-6.5, typically at a pH between 5 and 6. The alpha-amylase may be added as a single dose, e.g., before jet cooking.

Saccharification may be carried out using conditions well known in the art with a glucoamylase or a beta-amylase and optionally a debranching enzyme, such as an isoamylase or a pullulanase. For instance, a full saccharification step may last from about 24 to about 72 hours, however, it is also common to do a pre-saccharification of typically 40-90 minutes at a temperature between 30-65° C., typically about 60° C., followed by complete saccharification during fermentation in a simultaneous saccharification and fermentation (SSF) process. Saccharification is typically carried out at a temperature in the range of 20-75° C., e.g., 25-65° C. and 40-70° C., typically around 60° C., and at a pH between about 4 and 5, normally at about pH 4.5.

The saccharification and fermentation steps may be carried out either sequentially or simultaneously. In an embodiment, saccharification and fermentation are performed simultaneously (SSF), in which there is no holding stage for the saccharification, meaning that a fermenting organism, such as yeast, and enzyme(s) are added together. SSF is typically carried out at a temperature of 20-40° C., e.g., 26-34° C., preferably around 32° C., when the fermentation organism is yeast, such as a strain of *Saccharomyces cerevisiae*, and the fermentation product is ethanol.

Other fermentation products may be fermented at conditions and temperatures well known to persons skilled in the art, suitable for the fermenting organism in question. The temperature may be adjusted up or down during fermentation.

The dextrin may be recovered by methods well known in the art.

The sugar may be recovered by methods well known in the art.

The fermentation product may be recovered by methods well known in the art, e.g., by distillation.

In a particular embodiment, the process of the invention further comprises, prior to the conversion of a starch-containing material to dextrins and/or the treatment of the starch-containing material with an amino acid oxidase, an arginase, and/or an asparaginase, the steps of:

(x) reducing the particle size of the starch-containing material; and (y) forming a slurry comprising the starch-containing material and water.

Methods for reducing the particle size of the starch containing material are known to those skilled in the art. In an embodiment, the starch-containing material is milled to reduce the particle size.

The aqueous slurry may contain from 10-55 wt. % dry solids (DS), preferably 25-45 wt. % dry solids (DS), more preferably 30-40 wt. % dry solids (DS) of starch-containing material.

Processes for Producing Fermentation Products from Ungelatinized Starch-Containing Materials The present invention also relates to a process for producing a fermentation product from a starch-containing material without gelatinization (often referred to as "without cooking") of the starch-containing material. In an embodiment, the process includes saccharifying the (e.g., milled) starch-containing material below the initial gelatinization temperature, preferably in the presence of an alpha-amylase and/or a carbohydrate-source generating enzyme(s) (saccharifying enzyme(s)) to produce sugars that can be fermented into the fermentation product by a fermenting organism.

Accordingly, this aspect of the invention relates to a process of producing a fermentation product, comprising converting a starch-containing material to a dextrin with an alpha-amylase; saccharifying the dextrin to a sugar with a glucoamylase; and fermenting the sugar using a fermenting organism in the presence of an amino acid oxidase, an arginase, and/or an asparaginase in a single step at a temperature below the initial gelatinization temperature of the starch-containing material.

The term "initial gelatinization temperature" means the lowest temperature at which starch gelatinization commences. In general, starch heated in water begins to gelatinize between about 50° C. and 75° C.; the exact temperature of gelatinization depends on the specific starch and can readily be determined by the skilled artisan. Thus, the initial gelatinization temperature may vary according to the plant species, to the particular variety of the plant species as well as with the growth conditions. The initial gelatinization temperature of a given starch-containing material may be determined as the temperature at which birefringence is lost in 5% of the starch granules using the method described by Gorinstein and Lii, 1992, *Starch/Stärke* 44(12): 461-466.

The process of the present invention may further comprise recovering the fermentation product, e.g., by distillation.

The starch-containing material may be a slurry, such as granular starch, having 10-55 wt. % dry solids (DS), preferably 25-45 wt. % dry solids, more preferably 30-40 wt. % dry solids of starch-containing material may be prepared. The slurry may include water and/or process waters, such as stillage (backset), scrubber water, evaporator condensate or distillate, side-stripper water from distillation, or process water from other fermentation product plants. Because the process is carried out below the initial gelatinization temperature and thus no significant viscosity increase takes place, high levels of stillage may be used if desired. In an embodiment the aqueous slurry contains from about 1 to about 70 vol. %, preferably 15-60 vol. %, especially from about 30 to 50 vol. % water and/or process waters, such as stillage (backset), scrubber water, evaporator condensate or distillate, side-stripper water from distillation, or process water from other fermentation product plants, or combinations thereof, or the like.

The starch-containing material may be prepared by reducing the particle size, preferably by dry or wet milling, to 0.05-3.0 mm, preferably 0.1-0.5 mm. After being subjected to a method or process of the invention at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% of the dry solids in the starch-containing material is converted into a soluble starch hydrolyzate.

The process of this aspect of the invention is conducted at a temperature below the initial gelatinization temperature, e.g., a temperature in the range between 25-40° C., such as 25-40° C., 29-35° C., 30-34° C., such as around 32° C. One skilled in the art can easily determine suitable process conditions.

The process of the invention may be carried out at a pH from about 3 and 7, e.g., 3.5 to 6 or 4 to 5.

In an embodiment fermentation is carried out so that the sugar level, such as glucose level, is kept at a low level, such as below 6 wt. %, below about 3 wt. %, below about 2 wt. %, below about 1 wt. %., below about 0.5 wt. %, below 0.25% wt. %, or below about 0.1 wt. %. Such low levels of sugar can be accomplished by simply employing adjusted quantities of enzyme and fermenting organism. A skilled person in the art can easily determine which doses/quantities of enzyme and fermenting organism to use. The employed quantities of enzyme and fermenting organism may also be selected to maintain low concentrations of maltose in the fermentation broth. For instance, the maltose level may be kept below about 0.5 wt. %, such as below about 0.2 wt. %.

Starch-Containing Materials

Any suitable starch-containing starting material may be used in a process of the present invention. The starting material is generally selected based on the desired fermentation product. Examples of starch-containing starting materials, suitable for use in the processes of the present invention, include barley, beans, cassava, cereals, corn, milo, peas, potatoes, rice, rye, sago, sorghum, sweet potatoes, tapioca, wheat, and whole grains, or any mixture thereof. The starch-containing material may also be a waxy or non-waxy type of corn and barley.

Production of Fermentation Products and Sugars from a Plant Extract

The present invention also relates to a process of producing a sugar and/or a fermentation product such as ethanol, from a plant extract containing amino acid(s) and soluble sugar(s) (e.g., fructose, galactose, glucose, maltose, sucrose, and/or oligomers thereof), e.g., sugarcane, comprising applying an asparaginase and/or an amino acid oxidase to the plant extract.

In particular, the present invention relates to a process of producing a fermentation product, comprising
(a) treating a plant extract containing amino acid(s) and soluble sugar(s) with an amino acid oxidase, an arginase, and/or an asparaginase;
(b) producing molasses from the plant extract;
(c) diluting the molasses; and
(d) fermenting the diluted molasses with a fermenting organism to produce ethanol.

The present invention also relates to a process of producing a fermentation product, comprising
(a) treating a plant extract containing amino acid(s) and soluble sugar(s) with an amino acid oxidase, an arginase, and/or an asparaginase; and
(b) fermenting the treated plant extract with a fermenting organism to produce the fermentation product.

The present invention also relates to a process of producing a sugar, comprising
(a) treating a plant extract containing amino acid(s) and soluble sugar(s) with an amino acid oxidase, an arginase, and/or an asparaginase; and
(b) recovering the sugar from the treated plant extract.

The present invention also relates to a process of producing sucrose, comprising:
(a) treating a plant extract containing amino acid(s) and soluble sugar(s) with an amino acid oxidase, an arginase, and/or an asparaginase;
(b) clarification of the plant extract;
(c) concentration of sugars found in the clarified plant extract (e.g., by evaporation) to form a syrup containing sucrose;
(d) crystallization of sucrose from the syrup; and
(e) recovering sucrose.

The sugar may be any sugar including but not limited to fructose, galactose, glucose, maltose, or sucrose.

Sugarcane is any of 6 to 37 species of tall perennial grasses of the genus *Saccharum* (family Poaceae, tribe Andropogoneae). Traditionally, sugarcane processing requires two stages. Mills extract raw sugar from freshly harvested cane, and sometimes bleach the sugar to make "mill white" sugar for local consumption. Refineries then produce refined white sugar, which is 99% sucrose.

The mill washes, chops, and uses revolving knives to shred the cane. Shredded cane is repeatedly mixed with water and crushed between rollers called crushers or diffusers to produce raw sugarcane juice. The raw sugarcane juice contains 10-15% sucrose, and the remaining fibrous solids, called bagasse, are burned for fuel. The cane juice is next mixed with lime to adjust its pH to 7. This mixing arrests sucrose's decay into glucose and fructose, and precipitates some impurities. The mixture then sits, allowing the lime and other suspended solids to settle, resulting in clarified juice. Other methods for clarifying sugarcane juice such as sulfitation and carbonation are known in the art. The clarified juice is concentrated in a multiple-effect evaporator to make a syrup containing about 60 wt. % sucrose. This syrup is further concentrated under vacuum until it becomes supersaturated, and then seeded with crystalline sugar. On cooling, more sugar crystallizes from the syrup. A centrifuge separates sucrose from the molasses. Additional crystallizations extract more sucrose; the final residue is called blackstrap.

After clarification, water is removed from the sugarcane juice by a multistep evaporation process. The leftover from this process, not viable for sucrose extraction, is called molasses and is commonly used as a substrate for fuel ethanol production.

In a process of the present invention, the plant extract is treated with an amino acid oxidase, an arginase, and/or an asparaginase, and molasses is produced from the treated plant extract. Molasses is produced by clarification of the plant extract; concentration of sugars found in the clarified plant extract (e.g., by evaporation) to form a syrup; and crystallization of sucrose from the syrup to form the molasses. The molasses is then diluted, e.g., with water or plant extract juice (e.g., sugarcane juice), and the diluted molasses is fermented to produce a fermentation product.

The plant extract may be treated with an amino acid oxidase, an arginase, and/or an asparaginase in any step prior to evaporation. For example, the plant extract may be treated with an amino acid oxidase, an arginase, and/or an asparaginase during juice extraction, crushing, juice recovery, and/or juice clarification. Thus, the amino acid oxidase, the arginase, and/or the asparaginase may be added during the milling process and/or in the clarification steps.

The process of the present invention may further comprise recovering the fermentation product.

The process of the present invention may further comprise recovering the sugar. The sugar may be recovered by any process known in the art. For example, sucrose may be recovered by a process comprising
(x) clarification of the plant extract;
(y) concentration of sugars found in the clarified plant extract (e.g., by evaporation) to form a syrup; and
(z) crystallization of sucrose from the syrup.

As explained above, typically, mills run the raw juice clarification for sugar and/or ethanol at a pH of around 7 to minimize Maillard product formation. Another benefit of the process of the present invention is that the raw juice may be clarified for sugar and/or ethanol production at a more alkaline pH such as a pH of 7.5-9, e.g., 8-9. By using an amino acid oxidase, an arginase, and/or an asparaginase to avoid Maillard product formation, a higher pH can be used, which improves the clarification performance in terms of quality (sugar brightness and/or juice lighter), yield (decreases the amount of sugar which is lost in the refinery process) and productivity (decreases the clarification hold time).

The plant extract may be sweet sorghum, sugar beets, sugar cane, or any mixture thereof. In particular, the plant extract may be raw sugarcane juice or clarified sugarcane juice.

Fermentation Products

The term "fermentation product" means a product produced by a method or process including fermenting using a fermenting organism. Fermentation products include alcohols (e.g., ethanol, methanol, butanol); organic acids (e.g., citric acid, acetic acid, itaconic acid, lactic acid, succinic acid, gluconic acid); ketones (e.g., acetone); amino acids (e.g., glutamic acid); gases (e.g., $H_2$ and $CO_2$); antibiotics (e.g., penicillin and tetracycline); enzymes; vitamins (e.g., riboflavin, $B_{12}$, beta-carotene); and hormones. In a preferred embodiment the fermentation product is ethanol, e.g., fuel ethanol; drinking ethanol, i.e., potable neutral spirits; or industrial ethanol or products used in the consumable alcohol industry (e.g., beer and wine), dairy industry (e.g., fermented dairy products), leather industry and tobacco industry. Preferred beer types comprise ales, stouts, porters, lagers, bitters, malt liquors, happoushu, high-alcohol beer, low-alcohol beer, low-calorie beer or light beer.

Fermenting Organisms

The term "fermenting organism" refers to any organism, including bacterial and fungal organisms, such as yeast and filamentous fungi, suitable for producing a desired fermentation product. Suitable fermenting organisms according to the invention are able to ferment, i.e., convert, fermentable sugars, such as arabinose, fructose, glucose, maltose, mannose, or xylose, directly or indirectly into the desired fermentation product.

Examples of fermenting organisms include fungal organisms such as yeast. Preferred yeast include strains of *Saccharomyces*, in particular *Saccharomyces cerevisiae* or *Saccharomyces uvarum*; strains of *Pichia*, in particular *Pichia stipitis* such as *Pichia stipitis* CBS 5773 or *Pichia pastoris*; strains of *Candida*, in particular *Candida arabinofermentans*, *Candida boidinii*, *Candida diddensii*, *Candida shehatae*, *Candida sonorensis*, *Candida tropicalis*, or *Candida utilis*. Other fermenting organisms include strains of *Hansenula*, in particular *Hansenula anomala* or *Hansenula polymorpha*; strains of *Kluyveromyces*, in particular *Kluyveromyces fragilis* or *Kluyveromyces marxianus*; and strains of *Schizosaccharomyces*, in particular *Schizosaccharomyces pombe*.

Preferred bacterial fermenting organisms include strains of *Escherichia*, in particular *Escherichia coli*, strains of *Zymomonas*, in particular *Zymomonas mobilis*, strains of *Zymobacter*, in particular *Zymobactor palmae*, strains of *Klebsiella* in particular *Klebsiella oxytoca*, strains of *Leuconostoc*, in particular *Leuconostoc mesenteroides*, strains of *Clostridium*, in particular *Clostridium butyricum*, strains of *Enterobacter*, in particular *Enterobacter aerogenes*, and strains of *Thermoanaerobacter*, in particular *Thermoanaerobacter* BG1L1 (*Appl. Microbiol. Biotech.* 77: 61-86), *Thermoanarobacter ethanolicus*, *Thermoanaerobacter mathranii*, or *Thermoanaerobacter thermosaccharolyticum*. Strains of *Lactobacillus* are also envisioned as are strains of *Corynebacterium glutamicum R*, *Bacillus thermoglucosidaisus*, and *Geobacillus thermoglucosidasius*.

In an embodiment the fermenting organism is a C6 sugar fermenting organism, such as a strain of, e.g., *Saccharomyces cerevisiae*.

In one embodiment the fermenting organism is added to the fermentation medium so that the viable fermenting organism, such as yeast, count per mL of fermentation medium is in the range from $10^5$ to $10^{12}$, preferably from $10^7$ to $10^{10}$, especially about $5\times10^7$.

Yeast is the preferred fermenting organism for ethanol fermentation. Preferred are strains of *Saccharomyces*, especially strains of the species *Saccharomyces cerevisiae*, preferably strains which are resistant towards high levels of ethanol, i.e., up to, e.g., about 10, 12, 15 or 20 vol. % or more ethanol.

Commercially available yeast include LNF SA-1, LNF BG-1, LNF PE-2, and LNF CAT-1 (available from LNF Brazil), RED STAR™ and ETHANOL RED™ yeast (available from Fermentis/Lesaffre, USA), FALI (available from Fleischmann's Yeast, USA), SUPERSTART and THERMOSACC™ fresh yeast (available from Ethanol Technology, WI, USA), BIOFERM AFT and XR (available from NABC—North American Bioproducts Corporation, GA, USA), GERT STRAND (available from Gert Strand AB, Sweden), and FERMIOL (available from DSM Specialties).

According to the invention the fermenting organism capable of producing a desired fermentation product from fermentable sugars is preferably grown under precise conditions at a particular growth rate. When the fermenting organism is introduced into/added to the fermentation medium the inoculated fermenting organism pass through a number of stages. Initially growth does not occur. This period is referred to as the "lag phase" and may be considered a period of adaptation. During the next phase referred to as the "exponential phase" the growth rate gradually increases. After a period of maximum growth the rate ceases and the fermenting organism enters "stationary phase". After a further period of time the fermenting organism enters the "death phase" where the number of viable cells declines.

Fermentation

The fermentation conditions are determined based on, e.g., the kind of plant material, the available fermentable sugars, the fermenting organism(s) and/or the desired fermentation product. One skilled in the art can easily determine suitable fermentation conditions. The fermentation may according to the invention be carried out at conventionally used conditions. Preferred fermentation processes are anaerobic processes.

For example, fermentations may be carried out at temperatures as high as 75° C., e.g., between 40-70° C., such as between 50-60° C. However, bacteria with a significantly lower temperature optimum down to around room temperature (around 20° C.) are also known. Examples of suitable fermenting organisms can be found in the "Fermenting Organisms" section above.

For ethanol production using yeast, the fermentation may go on for 24 to 96 hours, in particular for 35 to 60 hours. In an embodiment the fermentation is carried out at a temperature between 20 to 40° C., preferably 26 to 34° C., in particular around 32° C. In an embodiment the pH is from pH 3 to 6, preferably around pH 4 to 5.

Other fermentation products may be fermented at temperatures known to the skilled person in the art to be suitable for the fermenting organism in question.

Fermentation is typically carried out at a pH in the range between 3 and 7, preferably from pH 3.5 to 6, such as around pH 5. Fermentations are typically ongoing for 6-96 hours.

The processes of the invention may be performed as a batch or as a continuous process. Fermentations may be conducted in an ultrafiltration system wherein the retentate is held under recirculation in the presence of solids, water, and the fermenting organism, and wherein the permeate is the desired fermentation product containing liquid. Equally contemplated are methods/processes conducted in continuous membrane reactors with ultrafiltration membranes and where the retentate is held under recirculation in presence of solids, water, and the fermenting organism(s) and where the permeate is the fermentation product containing liquid.

After fermentation the fermenting organism may be separated from the fermented slurry and recycled.

Fermentation Medium

The phrase "fermentation media" or "fermentation medium" refers to the environment in which fermentation is carried out and comprises the fermentation substrate, that is, the carbohydrate source that is metabolized by the fermenting organism(s).

The fermentation medium may comprise other nutrients and growth stimulator(s) for the fermenting organism(s). Nutrient and growth stimulators are widely used in the art of fermentation and include nitrogen sources, such as ammonia; vitamins and minerals, or combinations thereof.

Recovery

Subsequent to fermentation, the fermentation product may be separated from the fermentation medium. The fermentation medium may be distilled to extract the desired fermentation product or the desired fermentation product may be extracted from the fermentation medium by micro or membrane filtration techniques. Alternatively, the fermentation product may be recovered by stripping. Methods for recovery are well known in the art.

Enzymes

The enzyme(s) described below are to be used in an "effective amount" in the processes of the present invention.

Asparaginases

The asparaginase may be an enzyme of EC 3.5.1.1 (asparaginase or L-asparagine amidohydrolase) or EC 3.5.1.38 (glutamin-asparaginase or glutaminase-asparaginase).

The asparaginase may be a microbial asparaginase, e.g., an asparaginase derived from a bacterium, an archaeon or a fungus. For example, the asparaginase may be derived from Archaea, *Aspergillus, Candida, Erwinia, Fusarium*, or *Saccharomyces*. In particular, the asparaginase may be derived from *Aspergillus fumigatus, Aspergillus nidulans, Aspergillus niger, Aspergillus oryzae, Candida utilis, Erwinia chrysanthemii, Escherichia coli, Fusarium graminearum, Penicillium citrinum*, or *Saccharomyces cerevisiae*.

In an embodiment, the asparaginase has at least 70% sequence identity to SEQ ID NO: 1 (an *Aspergillus oryzae* asparaginase), e.g., at least 75%, at least 80%, at least 85%, at least 90%, at least 91%, at least 92%, at least 93%, at least 94%, at least 95%, at least 96%, at least 97%, at least 98%, or at least 99% sequence identity. In another embodiment, the asparaginase comprises or consists of the sequence of SEQ ID NO: 1; or is a fragment of SEQ ID NO: 1 which has asparaginase activity. Fragments of SEQ ID NO: 1 include the sequences of amino acids 27-378, 30-378, 75-378 and 80-378.

In another embodiment, the asparaginase has at least 70% sequence identity to SEQ ID NO: 2 (an *Aspergillus niger* asparaginase), e.g., at least 75%, at least 80%, at least 85%, at least 90%, at least 91%, at least 92%, at least 93%, at least 94%, at least 95%, at least 96%, at least 97%, at least 98%, or at least 99% sequence identity. In another embodiment, the asparaginase comprises or consists of the sequence of SEQ ID NO: 2; or is a fragment of SEQ ID NO: 2 which has asparaginase activity. Fragments of SEQ ID NO: 2 include the sequence of amino acids 80-378.

In another embodiment, the asparaginase has at least 70% sequence identity to SEQ ID NO: 3 (an *Aspergillus fumigatus* asparaginase), e.g., at least 75%, at least 80%, at least 85%, at least 90%, at least 91%, at least 92%, at least 93%, at least 94%, at least 95%, at least 96%, at least 97%, at least 98%, or at least 99% sequence identity. In another embodiment, the asparaginase comprises or consists of the sequence of SEQ ID NO: 3; or is a fragment of SEQ ID NO: 3 which has asparaginase activity. Fragments of SEQ ID NO: 3 include the sequence of amino acids 80-374.

In another embodiment, the asparaginase has at least 70% sequence identity to SEQ ID NO: 4 (an *Aspergillus nidulans* asparaginase), e.g., at least 75%, at least 80%, at least 85%, at least 90%, at least 91%, at least 92%, at least 93%, at least 94%, at least 95%, at least 96%, at least 97%, at least 98%, or at least 99% sequence identity. In another embodiment, the asparaginase comprises or consists of the sequence of SEQ ID NO: 4; or is a fragment of SEQ ID NO: 4 which has asparaginase activity. Fragments of SEQ ID NO: 4 include the sequence of amino acids 80-378.

In another embodiment, the asparaginase has at least 70% sequence identity to SEQ ID NO: 5 (a *Penicillium citrinum* asparaginase), e.g., at least 75%, at least 80%, at least 85%, at least 90%, at least 91%, at least 92%, at least 93%, at least 94%, at least 95%, at least 96%, at least 97%, at least 98%, or at least 99% sequence identity. In another embodiment, the asparaginase comprises or consists of the sequence of SEQ ID NO: 5; or is a fragment of SEQ ID NO: 5 which has asparaginase activity. Fragments of SEQ ID NO: 5 include the sequence of amino acids 80-379.

In another embodiment, the asparaginase has at least 70% sequence identity to SEQ ID NO: 6 (an *Aspergillus terreus* asparaginase), e.g., at least 75%, at least 80%, at least 85%, at least 90%, at least 91%, at least 92%, at least 93%, at least 94%, at least 95%, at least 96%, at least 97%, at least 98%, or at least 99% sequence identity. In another embodiment, the asparaginase comprises or consists of the sequence of SEQ ID NO: 6; or is a fragment of SEQ ID NO: 6 which has asparaginase activity. Fragments of SEQ ID NO: 6 include the sequence of amino acids 80-375.

In another embodiment, the asparaginase has at least 70% sequence identity to SEQ ID NO: 7 (a *Pyrococcus furiosus* asparaginase), e.g., at least 75%, at least 80%, at least 85%, at least 90%, at least 91%, at least 92%, at least 93%, at least 94%, at least 95%, at least 96%, at least 97%, at least 98%, or at least 99% sequence identity. In another embodiment, the asparaginase comprises or consists of the sequence of SEQ ID NO: 7; or is a fragment of SEQ ID NO: 7 which has asparaginase activity. Fragments of SEQ ID NO: 7 include the sequence of amino acids 80-375.

An asparaginase useful according to the present invention may have the amino acid sequence disclosed in WO 2004/026043, WO 2004/030468, WO 2004/032648, WO 2008/110513, WO 2008/128974, WO 2008/128975, and WO 2008/151807, or an amino acid sequence having at least 50%, at least 60%, at least 70%, at least 80%, at least 85%, at least 90%, at least 91%, at least 92%, at least 93%, at least 94%, at least 95%, at least 96%, at least 97%, at least 98% or at least 99% identity to an asparaginase disclosed therein. Such an asparaginase is preferably derived from *Aspergillus niger* or *Aspergillus oryzae*.

Examples of asparaginases include variants of the above-listed asparaginases, e.g., variants, which have one or more conservative amino acid substitutions.

The asparaginase may be partly or completely post-translationally processed. For instance, they may be N-terminally truncated at different positions, so that different N-terminal sequences will be found. The wild-type *Aspergillus oryzae* asparaginase (SEQ ID NO: 1), when produced in *Aspergillus oryzae*, has been found to be heterogeneously processed such that at least four N-terminal sequences were found in a purified sample, corresponding to polypeptides being truncated to amino acids 27-378, 30-378, 75-378 or 80-378. Other asparaginases may be truncated at corresponding positions, or at other positions. For example, an asparaginase may be truncated immediately before the position corresponding to any of positions 27, 30, 75 or 80 of SEQ ID NO: 1. The term 'immediately before' means that the truncation takes place at the N-terminal side of the position mentioned.

The asparaginase may show a high thermotolerance, e.g., a high thermostability or a high relative asparaginase activity at a high temperature.

In one aspect, the asparaginase may be thermostable or have a high thermostability. The thermostability may be determined as the residual asparaginase activity after heat treatment divided by the asparaginase activity without heat treatment. Heat treatment may be incubation at pH 6 or around pH 6 at a high temperature for, e.g., 10, 20, 30 or 40 minutes. The asparaginase activity without heat treatment may be determined as the asparaginase activity of a sample which has been incubated at 4° C. in the same buffer and for the same time as the sample which is heat treated, or it may be the asparaginase activity before heat treatment.

The asparaginase may be thermostable and show a residual asparaginase activity of at least 90%, such as at least 80%, at least 70%, at least 60%, at least 50% or at least 40%, after incubation at pH 6 at a high temperature for a period of time, e.g., 20 minutes, compared to the asparaginase activity without heat treatment.

A high temperature in the context of the present invention may mean, e.g., 55° C., 58° C., 60° C., 61° C., 62° C., 63° C., 64° C., 65° C., 66° C., 67° C., 68° C., 69° C., 70° C., 72° C. or 75° C.

Asparaginase activity may be determined by any method known in the art. For example, asparaginase activity may be determined by incubating the enzyme with L-asparagine and hydroxylamine in a potassium phosphate buffer at pH 6 for 20 minutes followed by the coupling reaction with $FeCl_2$ and measuring A490, as described in Example 4 of WO 2008/135547. Incubation may be at any suitable temperature, e.g., 55° C.

In another aspect, the asparaginase may have a high relative activity at a high temperature compared to a reference temperature, e.g., 37° C., 40° C., 45° C. or 50° C. The asparaginase activity at a high temperature and, e.g., 37° C. may be determined as described above, where the incubation with asparagine is performed at a high temperature and 37° C., respectively. The asparaginase activity at a high temperature divided by the activity at 37° C. may be at least 110%, preferably at least 120%, such as at least 125%, 130%, 140%, 150%, 170% or 200%, more preferably at least 250%, such as at least 300%, and even more preferably at least 500% or at least 700%.

The asparaginase may be a variant, which comprises an amino acid difference in at least one of the following regions: positions 68-74, positions 279-288, positions 309-319, positions 329-342, and/or positions 356-363; wherein each position corresponds to a position of amino acids 1 to 378 of SEQ ID NO: 1.

Thus, the asparaginase may comprise a difference in the amino acid sequence at one or more positions selected from the group consisting of 68, 69, 70, 71, 72, 73, 74, 279, 280, 281, 282, 283, 284, 285, 286, 287, 288, 309, 310, 311, 312, 313, 314, 315, 316, 317, 318, 319, 329, 330, 331, 332, 333, 334, 335, 336, 337, 338, 339, 340, 341, 342, 356, 357, 358, 359, 360, 361, 362, and/or 363, wherein each position corresponds to a position in SEQ ID NO: 1. In a preferred embodiment, the amino acid difference is a substitution.

In another embodiment, the asparaginase comprises an amino acid difference at one or more positions selected from the group consisting of D88, D111, K194, R196, D206, E235, E255, R266, D275, K290, E311, and E331; wherein each position corresponds to a position of amino acids 1 to 378 of SEQ ID NO: 1. Preferably, the amino acid difference is a substitution. Therefore, in a preferred aspect, the asparaginase comprises one or more substitutions selected from the group consisting of D88N, D111N, K194E, R196E, D206N, E235Q, E255Q, R266L, D275N, K290E, E311K, and E331Q.

In another embodiment, the asparaginase comprises an amino acid difference in at least one of the following positions selected from the group consisting of N70, G82, I83, Q84, T85, T113, D115, A137, V164, L201, N278, T280, F306, I365, and E366, wherein each position corresponds to a position of amino acids 1 to 378 of SEQ ID NO: 1. Preferably, the amino acid difference is a substitution. Therefore, in a preferred aspect, the asparaginase comprises at least one of the following amino acid substitutions selected from the group consisting of N70P, G82P, I83P, Q84P, T85P, T113P, D115P, A137P, V164P, L201P, N278P, T280P, F306P, I365P, and E366P.

In another embodiment, the asparaginase comprises an amino acid difference in one or more of positions selected from the group consisting of S176, D223, G231, P246, Y271, S283, G328 (substitution to C will potentially result in formation of one or more disulfide bridges); D223, K249, and D286 (based on hydrophobic or electrostatic contacts), wherein each position corresponds to a position of amino acids 1 to 378 of SEQ ID NO: 1. Preferably, the amino acid difference is a substitution. Therefore, in a preferred aspect, the asparaginase comprises one or more substitutions selected from the group consisting of S176C; D223C; D223N/L; G231C; P246C; K249V/I/L; Y271C; S283C; D286R/N/L; and G328C.

In another embodiment, the asparaginase comprises an amino acid difference in one or more positions D69; N70; A72; N278; D279; T280; L281; S283; D286; K290; S307; E311; D312; H317; A336; E337; Q361; and K363, wherein each position corresponds to a position of amino acids 1 to 378 of SEQ ID NO: 1. Preferably, the amino acid difference is a substitution. Therefore, in a preferred aspect, the asparaginase comprises one or more substitutions selected from the group consisting of D69R/K; N70P/R/K; A72R/K; N278H/Q/R/K; D279N/V/R; T280D/E; L281 D/E; D286N/V/R; K290E/L; S307A/D/E; E311Q/I/R; D312Y/N/V/R; H317D/E; A336P; E337Q/R/K/I; Q361K/R; and K363P/Q/E/L.

In another embodiment, the asparaginase comprises an amino acid difference in one or more positions selected from the group consisting of 54, 57, 70, 83, 84, 86, 93-96, 102, 107, 137, 139, 165, 172, 184-186, 209, 212, 214, 215, 219, 220, 224, 260, 262, 264, 266, 299, 318, 320, 321, 323, 325, 327, 349, 351, 353 and 356, wherein each position corresponds to a position of amino acids 1 to 378 of SEQ ID NO: 1. Preferably, the amino acid difference is a substitution. Therefore, in a preferred aspect, the asparaginase comprises one or more substitutions selected from the group consisting of V54I, F57L, N70K, I83V, Q84D, L86P, M93L, L94K, N95D, V96L, V102D, V107I, A137I, V139I, I165L, S172A, L184Y, Q185N, S186A, V209G, F212R, A214V, S215T, A219T, N220T, T224A, N260K, T262D, I264L, R266K, S299N, N318G, P320V, I321V, A323R, T325S, T327V, A349Q, S351A, V353I and G356M.

In a more preferred aspect, the asparaginase comprises one or more substitutions selected from the group consisting of V54I, F57L, N70K, I83V, Q84D, L86P, V102D, N260K, T262D, A323R, T327V, A349Q, S351A and V353I, wherein each position corresponds to a position in SEQ ID NO: 1.

In an even more preferred aspect, the asparaginase comprises one or more substitutions selected from the group consisting of N70K, A323R, T327V, A349Q, S351A and V353I, wherein each position corresponds to a position in SEQ ID NO: 1.

In another embodiment, the asparaginase comprises an amino acid difference in at least one of the following positions: 54, 57, 68-74, 82-86, 88, 93-96, 102, 107, 111, 113, 115, 137, 139, 164, 165, 172, 176, 184-186, 194, 196, 201, 206, 209, 212, 214, 215, 219, 220, 223, 224, 226, 228, 231, 235, 246, 249, 255, 260, 262, 264, 266, 271, 275, 278-288, 290, 299, 306, 307, 309-321, 323, 325, 327-342, 349, 351, 353, 356-363, 365, 366 and 375, wherein each position corresponds to a position in SEQ ID NO: 1.

Preferably, the asparaginase comprises an amino acid difference in at least one of the following positions: 54, 57, 70, 83, 84, 86, 102, 137, 164, 196, 201, 228, 260, 262, 278, 283, 290, 307, 312, 323, 327, 334, 336, 337, 349, 351, 353, 366 and/or 375, wherein each position corresponds to a position in SEQ ID NO: 1.

The asparaginase may comprise an amino acid substitution. Preferably, the asparaginase comprises at least one of the following substitutions: 54I, 57L, 69K/R, 70H/K/P/R/S, 72K/R, 82P, 83P/V, 84P/D, 85P, 86P, 88N, 93L, 94K, 95D, 96L, 102D, 107I, 111N, 113P, 115P, 137P/S/I, 139I, 164D/P, 165L, 172A, 176C, 184Y, 185N, 186A, 194E, 196E/I, 201P/Q, 206N, 209G, 212R, 214V, 215T, 219T, 220T, 223C/L/N, 224A, 228V, 231C, 235Q, 246C, 249I/L/V, 255Q, 260K, 262D, 264L, 266L/K, 271O, 275N, 278H/K/P/Q/R, 279N/R/V, 280D/E/P, 281D/E, 283C, 286L/N/R/V, 290E/L/V, 299N, 306P, 307A/D/E, 311I/K/Q/R, 312N/R/V/Y, 317D/E, 318G, 320V, 321V, 323R, 325S, 327V, 328C, 331Q, 334F, 336C/G/L/P, 337F/I/K/Q/R, 349Q, 351A, 353I, 356M, 361K/R, 363E/L/P/Q, 365P, 366P and/or 375T. More preferably, the asparaginase comprises at least one of the following substitutions: 54I, 57L, 70H/K/S, 83V, 84D, 86P, 102D, 137S, 164D, 196I, 201Q, 228V, 260K, 262D, 278H/Q, 283C, 290V, 307A, 312Y, 323R, 327V, 334F, 336C/G/L, 337F/I, 349Q, 351A, 353I, 366P and/or 375T. Even more preferably, the asparaginase comprises at least one, such as at least two, at least three, at least four or at least five, of the following substitutions: 70K, 323R, 327V, 349Q, 351A and/or 353I. Even more preferably, the asparaginase comprises the following substitutions: 70K, 323R, 327V, 349Q, 351A and 353I. Most preferably, the asparaginase has the same sequence as SEQ ID NO: 1, or a homologous sequence, except for the following substitutions: 70K, 323R, 327V, 349Q, 351A and 353I. The asparaginase may be a variant of a parent enzyme having the sequence of SEQ ID NO: 1 or a homologous sequence.

In one aspect, the asparaginase comprises an amino acid difference at a position corresponding to any of positions 70, 137, 164, 196, 201, 228, 278, 290, 366 and/or 375 in SEQ ID NO: 1. Preferably, the asparaginase comprises at least one of the following substitutions: 70H/K/S, 137S, 164D, 196I, 201Q, 228V, 278H/Q, 290V, 366P and/or 375T. The asparaginase may have a high relative asparaginase activity at high temperature.

Particularly preferred asparaginases comprise the following substitutions or sets of substitutions: 70H, 70K, 70K+278H, 70K+278H+196I, 70K+278H+201Q, 70K+283C, 70S, 137S, 137S+228V, 164D, 196I, 201Q, 278H, 278Q, 290V, 366P, and/or 366P+375T.

In another preferred aspect, the asparaginase comprises an amino acid difference in at least one of the following positions: 70, 283, 307, 312, 334, 336 and/or 337. Preferably, the asparaginase comprises at least one of the following substitutions: 70K, 283C, 307A, 312Y, 334F, 336C/G/L and/or 337F/I, wherein each position corresponds to a position of amino acids 1 to 378 of SEQ ID NO: 1.

Particularly preferred asparaginases comprise the following substitutions or sets of substitutions: 70K, 70K+283C, 70K+283C+307A+312Y, 70K+283C+307A+312Y+336L+337F, 70K+307A, 70K+307A+312Y, 70K+307A+312Y+334F, 70K+307A+312Y+336G+337I, 70K+307A+312Y+336L+337F, 70K+312Y, and/or 70K+336C+337F.

In another preferred aspect of the present invention, the asparaginase comprises an amino acid difference at a position corresponding to any of positions 54, 57, 70, 83, 84, 86, 93-96, 102, 107, 137, 139, 165, 172, 184-186, 209, 212, 214, 215, 219, 220, 224, 260, 262, 264, 266, 299, 318, 320, 321, 323, 325, 327, 349, 351, 353 and/or 356 in SEQ ID NO: 1. Preferably, the asparaginase comprises at least one of the following substitutions: V54I, F57L, N70K, I83V, Q84D, L86P, M93L, L94K, N95D, V96L, V102D, V107I, A137I, V139I, I165L, S172A, L184Y, Q185N, S186A, V209G, F212R, A214V, S215T, A219T, N220T, T224A, N260K, T262D, I264L, R266K, S299N, N318G, P320V, I321V, A323R, T325S, T327V, A349Q, S351A, V353I and/or G356M. More preferably, the asparaginase comprises at least one of the following substitutions: V54I, F57L, N70K, I83V, Q84D, L86P, V102D, N260K, T262D, A323R, T327V, A349Q, S351A and/or V353I. Most preferably, the asparaginase comprises at least one, such as at least two, at least three, at least four or at least five, of the following substitutions: N70K, A323R, T327V, A349Q, S351A and/or V353I. The asparaginase may have a high relative asparaginase activity at a high temperature.

Particularly preferred asparaginases comprise the following sets of substitutions: N70K+V54I+F57L, N70K+I83V+Q84D+A323R+T327V, N70K+I83V+Q84D+A323R+T327V+A349Q+S351A+V353I, N70K+L86P+V102D+A323R+T327V, N70K+V102D+A323R+T327V+A349Q+S351A+V353I, N70K+N260K+T262D, N70K+A323R+T327V, N70K+A323R+T327V+A349Q+S351A+V353I, and/or N70K+A349Q+S351A+V353I.

In an embodiment, an asparaginase variant has at least 70% sequence identity e.g., at least 75%, at least 80%, at least 85%, at least 90%, at least 91%, at least 92%, at least 93%, at least 94%, at least 95%, at least 96%, at least 97%, at least 98%, or at least 99%, but less than 100% sequence identity to SEQ ID NO: 1.

In an embodiment, an asparaginase variant has at least 70% sequence identity e.g., at least 75%, at least 80%, at least 85%, at least 90%, at least 91%, at least 92%, at least 93%, at least 94%, at least 95%, at least 96%, at least 97%, at least 98%, or at least 99%, but less than 100% sequence identity to SEQ ID NO: 2.

In an embodiment, an asparaginase variant has at least 70% sequence identity e.g., at least 75%, at least 80%, at least 85%, at least 90%, at least 91%, at least 92%, at least 93%, at least 94%, at least 95%, at least 96%, at least 97%, at least 98%, or at least 99%, but less than 100% sequence identity to SEQ ID NO: 3.

In an embodiment, an asparaginase variant has at least 70% sequence identity e.g., at least 75%, at least 80%, at least 85%, at least 90%, at least 91%, at least 92%, at least 93%, at least 94%, at least 95%, at least 96%, at least 97%, at least 98%, or at least 99%, but less than 100% sequence identity to SEQ ID NO: 4.

In an embodiment, an asparaginase variant has at least 70% sequence identity e.g., at least 75%, at least 80%, at least 85%, at least 90%, at least 91%, at least 92%, at least 93%, at least 94%, at least 95%, at least 96%, at least 97%, at least 98%, or at least 99%, but less than 100% sequence identity to SEQ ID NO: 5.

In an embodiment, an asparaginase variant has at least 70% sequence identity e.g., at least 75%, at least 80%, at least 85%, at least 90%, at least 91%, at least 92%, at least 93%, at least 94%, at least 95%, at least 96%, at least 97%, at least 98%, or at least 99%, but less than 100% sequence identity to SEQ ID NO: 6.

In an embodiment, an asparaginase variant has at least 70% sequence identity e.g., at least 75%, at least 80%, at least 85%, at least 90%, at least 91%, at least 92%, at least 93%, at least 94%, at least 95%, at least 96%, at least 97%, at least 98%, or at least 99%, but less than 100% sequence identity to SEQ ID NO: 7.

An asparaginase may be a tetramer in its most active form.

In one embodiment, the asparaginase is provided in an amount of about 100-10,000 ASNU per kg dry matter, more preferably about 250-8,000 ASNU per kg dry matter, more preferably about 500-7,500 ASNU per kg dry matter and most preferably about 1,000-5,000 ASNU per kg dry matter.

An asparaginase unit (ASNU) is defined as the amount of enzyme needed to generate 1.0 micromole of ammonia from hydrolyzing asparagine in 1 minute at 37° C. and pH 7.0. The concentration of asparagine when determining the activity may be 9.6 mg/ml.

Amino Acid Oxidases

Amino acid oxidases, belonging to enzyme classes EC1.4.3.2 and EC1.4.3.3, are oxidoreductases which catalyze the deamination of amino acids found in nature to the corresponding oxo-acids. An amino acid oxidase from fungal, bacterial, or plant sources may be used. The amino acid oxidase may, e.g., be derived from *Bothrops atrox, Rhodococcus opacus, Trichoderma harzianum, Trigonopsis variabilis*, or another organism.

In another embodiment, the amino acid oxidase has at least 70% sequence identity to SEQ ID NO: 8, a *Bothrops atrox* amino acid oxidase, e.g., at least 75%, at least 80%, at least 85%, at least 90%, at least 91%, at least 92%, at least 93%, at least 94%, at least 95%, at least 96%, at least 97%, at least 98%, or at least 99% sequence identity. In another embodiment, the amino acid oxidase comprises or consists of the sequence of SEQ ID NO: 8; or is a fragment of SEQ ID NO: 8 which has amino acid oxidase activity.

In another embodiment, the amino acid oxidase has at least 70% sequence identity to SEQ ID NO: 9, a *Trichoderma harzianum* amino acid oxidase, e.g., at least 75%, at least 80%, at least 85%, at least 90%, at least 91%, at least 92%, at least 93%, at least 94%, at least 95%, at least 96%, at least 97%, at least 98%, or at least 99% sequence identity. In another embodiment, the amino acid oxidase comprises or consists of the sequence of SEQ ID NO: 9; or is a fragment of SEQ ID NO: 9 which has amino acid oxidase activity.

In another embodiment, the amino acid oxidase has at least 70% sequence identity to SEQ ID NO: 10, a *Trigonopsis variabilis* amino acid oxidase, e.g., at least 75%, at least 80%, at least 85%, at least 90%, at least 91%, at least 92%, at least 93%, at least 94%, at least 95%, at least 96%, at least 97%, at least 98%, or at least 99% sequence identity. In another embodiment, the amino acid oxidase comprises or consists of the sequence of SEQ ID NO: 10; or is a fragment of SEQ ID NO: 10 which has amino acid oxidase activity.

In another embodiment, the amino acid oxidase has at least 70% sequence identity to SEQ ID NO: 11, a *Rhodococcus opacus* amino acid oxidase, e.g., at least 75%, at least 80%, at least 85%, at least 90%, at least 91%, at least 92%, at least 93%, at least 94%, at least 95%, at least 96%, at least 97%, at least 98%, or at least 99% sequence identity. In another embodiment, the amino acid oxidase comprises or consists of the sequence of SEQ ID NO: 11; or is a fragment of SEQ ID NO: 11 which has amino acid oxidase activity.

In another embodiment, the amino acid oxidase has at least 70% sequence identity to SEQ ID NO: 12, an *Aspergillus nidulans* amino acid oxidase, e.g., at least 75%, at least 80%, at least 85%, at least 90%, at least 91%, at least 92%, at least 93%, at least 94%, at least 95%, at least 96%, at least 97%, at least 98%, or at least 99% sequence identity. In another embodiment, the amino acid oxidase comprises or consists of the sequence of SEQ ID NO: 12; or is a fragment of SEQ ID NO: 12 which has amino acid oxidase activity.

In another embodiment, the amino acid oxidase has at least 70% sequence identity to SEQ ID NO: 13, a *Streptococcus oligofermentans* amino acid oxidase, e.g., at least 75%, at least 80%, at least 85%, at least 90%, at least 91%, at least 92%, at least 93%, at least 94%, at least 95%, at least 96%, at least 97%, at least 98%, or at least 99% sequence identity. In another embodiment, the amino acid oxidase comprises or consists of the sequence of SEQ ID NO: 13; or is a fragment of SEQ ID NO: 13 which has amino acid oxidase activity.

In another embodiment, the amino acid oxidase has at least 70% sequence identity to SEQ ID NO: 14, a *Neurospora crassa* amino acid oxidase, e.g., at least 75%, at least 80%, at least 85%, at least 90%, at least 91%, at least 92%, at least 93%, at least 94%, at least 95%, at least 96%, at least 97%, at least 98%, or at least 99% sequence identity. In another embodiment, the amino acid oxidase comprises or consists of the sequence of SEQ ID NO: 14; or is a fragment of SEQ ID NO: 14 which has amino acid oxidase activity.

An amino acid oxidase useful according to the present invention may have the amino acid sequence disclosed in WO 94/25574; WO 2005/098000; EP 1205542; Alves et al., 2008, UniProt Database, Accession No. P0CC17; Davis et al., 2005, *Appl. Environ. Microbiol.* 71(7): 3551-3555; Tong et al., 2008, *J. Bacteriol.* 190(13): 4716-4721; Niedermann et al., 1990, *J. Biol. Chem.* 265(28): 17246-17251; or an amino acid sequence having at least 50%, at least 60%, at least 70%, at least 80%, at least 85%, at least 90%, at least 91%, at least 92%, at least 93%, at least 94%, at least 95%, at least 96%, at least 97%, at least 98% or at least 99% identity to an amino acid oxidase disclosed therein.

Arginases

Arginases (L-Arginine aminohydrolase, EC 3.5.3.1) are a group of enzymes which catalyze the hydrolysis of arginine to ornithine and urea. An arginase from fungal, bacterial, plant, or animal sources may be used.

In an embodiment, the arginase has at least 70% sequence identity to SEQ ID NO: 15, a *Bacillus cereus* arginase, e.g., at least 75%, at least 80%, at least 85%, at least 90%, at least 91%, at least 92%, at least 93%, at least 94%, at least 95%, at least 96%, at least 97%, at least 98%, or at least 99% sequence identity. In another embodiment, the arginase comprises or consists of the sequence of SEQ ID NO: 15; or is a fragment of SEQ ID NO: 15 which has arginase activity.

In another embodiment, the arginase has at least 70% sequence identity to SEQ ID NO: 16, an arginase obtained from tomato, e.g., at least 75%, at least 80%, at least 85%, at least 90%, at least 91%, at least 92%, at least 93%, at least 94%, at least 95%, at least 96%, at least 97%, at least 98%, or at least 99% sequence identity. In another embodiment, the arginase comprises or consists of the sequence of SEQ ID NO: 16; or is a fragment of SEQ ID NO: 16 which has arginase activity.

In another embodiment, the arginase has at least 70% sequence identity to SEQ ID NO: 17, an arginase obtained from mushroom, e.g., at least 75%, at least 80%, at least 85%, at least 90%, at least 91%, at least 92%, at least 93%, at least 94%, at least 95%, at least 96%, at least 97%, at least 98%, or at least 99% sequence identity. In another embodiment, the arginase comprises or consists of the sequence of SEQ ID NO: 17; or is a fragment of SEQ ID NO: 17 which has arginase activity.

In another embodiment, the arginase has at least 70% sequence identity to SEQ ID NO: 18, an arginase from pig, e.g., at least 75%, at least 80%, at least 85%, at least 90%, at least 91%, at least 92%, at least 93%, at least 94%, at least 95%, at least 96%, at least 97%, at least 98%, or at least 99% sequence identity. In another embodiment, the arginase comprises or consists of the sequence of SEQ ID NO: 18; or is a fragment of SEQ ID NO: 18 which has arginase activity.

In another embodiment, the arginase has at least 70% sequence identity to SEQ ID NO: 19, e.g., at least 75%, at least 80%, at least 85%, at least 90%, at least 91%, at least 92%, at least 93%, at least 94%, at least 95%, at least 96%, at least 97%, at least 98%, or at least 99% sequence identity. In another embodiment, the arginase comprises or consists of the sequence of SEQ ID NO: 19; or is a fragment of SEQ ID NO: 19 which has arginase activity.

According to the invention arginase and asparginase are equivalent enzymes due to the similar mode of action. Both enzymes (i.e., arginase and asparginase) act on the nitrogen-containing side chains of similar amino acids and release nitrogen-containing compounds, i.e., release urea ($CO(NH_2)_2$) and amonia ($NH_3$), respectively.

Alpha-Amylases

According to the invention any alpha-amylase may be used, such as of fungal, bacterial or plant origin. In a preferred embodiment the alpha-amylase is an acid alpha-amylase, e.g., acid fungal or acid bacterial alpha-amylase. The term "acid alpha-amylase" means an alpha-amylase (EC 3.2.1.1) which added in an effective amount has activity optimum at a pH in the range of 3 to 7, preferably from 3.5 to 6, or more preferably from 4-5.

Bacterial Alpha-Amylases

An alpha-amylase for use in the present invention may be a bacterial alpha-amylase, e.g., derived from *Bacillus*. In a preferred embodiment the *Bacillus* alpha-amylase is derived from a strain of *Bacillus amyloliquefaciens, Bacillus licheniformis, Bacillus stearothermophilus*, or *Bacillus subtilis*, but may also be derived from other *Bacillus* sp.

Specific examples of alpha-amylases include the *Bacillus amyloliquefaciens* alpha-amylase of SEQ ID NO: 5 in WO 99/19467, the *Bacillus licheniformis* alpha-amylase of SEQ ID NO: 4 in WO 99/19467, and the *Bacillus stearothermophilus* alpha-amylase of SEQ ID NO: 3 in WO 99/19467 (all sequences are hereby incorporated by reference). In an embodiment the alpha-amylase may be an enzyme having a degree of identity of at least 60%, e.g., at least 70%, at least 80%, at least 90%, at least 95%, at least 96%, at least 97%, at least 98% or at least 99% to any of the sequences shown in SEQ ID NOS: 3, 4 or 5, respectively, in WO 99/19467.

The *Bacillus* alpha-amylase may also be a variant and/or hybrid, especially one described in any of WO 96/23873, WO 96/23874, WO 97/41213, WO 99/19467, WO 00/60059, and WO 02/10355 (all documents are hereby incorporated by reference). Specific alpha-amylase variants are disclosed in U.S. Pat. Nos. 6,093,562, 6,187,576, and 6,297,038 (hereby incorporated by reference) and include *Bacillus stearothermophilus* alpha-amylase (BSG alpha-amylase) variants having a deletion of one or two amino acids at positions R179 to G182, preferably a double deletion disclosed in WO 96/23873—see, e.g., page 20, lines 1-10 (hereby incorporated by reference), preferably corresponding to delta (181-182) compared to the amino acid sequence of *Bacillus stearothermophilus* alpha-amylase set forth in SEQ ID NO: 3 disclosed in WO 99/19467 or the deletion of amino acids R179 and G180 using SEQ ID NO: 3 in WO 99/19467 for numbering (which reference is hereby incorporated by reference). Even more preferred are *Bacillus* alpha-amylases, especially *Bacillus stearothermophilus* alpha-amylases, which have a double deletion corresponding to delta (181-182) and further comprise a N193F substitution (also denoted I181*+G182*+N193F) compared to the wild-type BSG alpha-amylase amino acid sequence set forth in SEQ ID NO: 3 disclosed in WO 99/19467.

Bacterial Hybrid Alpha-Amylases

The alpha-amylase may be a hybrid alpha-amylase, e.g., an alpha-amylase comprising 445 C-terminal amino acid residues of the *Bacillus licheniformis* alpha-amylase (shown in SEQ ID NO: 4 of WO 99/19467) and the 37 N-terminal amino acid residues of the alpha-amylase derived from *Bacillus amyloliquefaciens* (shown in SEQ ID NO: 5 of WO 99/19467), with one or more, especially all, of the following substitutions: G48A+T49I+G107A+H156Y+A181T+N190F+I201F+A209V+Q264S (using the *Bacillus licheniformis* numbering in SEQ ID NO: 4 of WO 99/19467). Also preferred are variants having one or more of the following mutations (or corresponding mutations in other *Bacillus* alpha-amylases): H154Y, A181T, N190F, A209V and Q264S and/or the deletion of two residues between positions 176 and 179, preferably the deletion of E178 and G179 (using SEQ ID NO: 5 of WO 99/19467 for position numbering).

In an embodiment, the bacterial alpha-amylase is dosed in an amount of 0.0005-5 KNU per g DS (dry solids), preferably 0.001-1 KNU per g DS, such as around 0.050 KNU per g DS.

Fungal Alpha-Amylases

Fungal alpha-amylases include alpha-amylases derived from a strain of *Aspergillus*, such as, *Aspergillus kawachii, Aspergillus niger* and *Aspergillus oryzae* alpha-amylases.

A preferred acidic fungal alpha-amylase is an alpha-amylase which exhibits a high identity, i.e., at least 70%, at least 75%, at least 80%, at least 85%, at least 90%, at least 95%, at least 96%, at least 97%, at least 98%, at least 99% or even 100% identity to the mature part of the amino acid sequence shown in SEQ ID NO: 10 in WO 96/23874.

Another preferred acid alpha-amylase is derived from a strain of *Aspergillus niger*. In a preferred embodiment the acid fungal alpha-amylase is an *Aspergillus niger* alpha-amylase disclosed as "AMYA_ASPNG" in the Swiss-prot/TeEMBL database under the primary accession no. P56271 and described in WO 89/01969 (Example 3—incorporated by reference). A commercially available acid fungal alpha-amylase derived from *Aspergillus niger* is SP288 (available from Novozymes A/S, Denmark).

Other wild-type alpha-amylases include those derived from a strain of *Meripilus* and *Rhizomucor*, preferably a strain of *Meripilus giganteus* or *Rhizomucor pusillus* (WO 2004/055178 which is incorporated herein by reference).

In a preferred embodiment the alpha-amylase is derived from *Aspergillus kawachii* (Kaneko et al., 1996, *J. Ferment. Bioeng.* 81: 292-298, "Molecular-cloning and determination of the nucleotide-sequence of a gene encoding an acid-stable alpha-amylase from *Aspergillus kawachii*"; and further as EMBL: #AB008370).

The fungal alpha-amylase may also be a wild-type enzyme comprising a starch-binding domain (SBD) and an alpha-amylase catalytic domain, or a variant thereof.

Fungal Hybrid Alpha-Amylases

In a preferred embodiment the fungal acid alpha-amylase is a hybrid alpha-amylase. Examples of fungal hybrid alpha-amylases include the ones disclosed in WO 2005/003311, U.S. Patent Application Publication No. 2005/0054071 (Novozymes), and WO 2006/069290 (Novozymes), which are hereby incorporated by reference. A hybrid alpha-amylase may comprise an alpha-amylase catalytic domain (CD) and a carbohydrate-binding domain/module (CBM), such as a starch binding domain (SBD), and optionally a linker.

Examples of hybrid alpha-amylases include those disclosed in Tables 1 to 5 of the examples in WO 2006/069290 including the variant with the catalytic domain JA118 and *Athelia rolfsii* SBD (SEQ ID NO: 100 in WO 2006/069290), *Rhizomucor pusillus* alpha-amylase with *Athelia rolfsii* AMG linker and SBD (SEQ ID NO: 101 in WO 2006/069290), *Rhizomucor pusillus* alpha-amylase with *Aspergillus niger* glucoamylase linker and SBD (which is disclosed in Table 5 as a combination of amino acid sequences SEQ ID NO: 20, SEQ ID NO: 72 and SEQ ID NO: 96 in U.S. application Ser. No. 11/316,535) or as V039 in Table 5 in WO 2006/069290, and *Meripilus giganteus* alpha-amylase with *Athelia rolfsii* glucoamylase linker and SBD (SEQ ID NO: 102 in WO 2006/069290). Other hybrid alpha-amylases are listed in Tables 3, 4, 5, and 6 in Example 4 in U.S. application Ser. No. 11/316,535 and WO 2006/069290 (which are hereby incorporated by reference).

Other examples of hybrid alpha-amylases include those disclosed in U.S. Patent Application Publication No. 2005/0054071, including those disclosed in Table 3 on page 15, such as *Aspergillus niger* alpha-amylase with *Aspergillus kawachii* linker and starch binding domain.

Other alpha-amylases exhibit a high degree of sequence identity to any of above mentioned alpha-amylases, i.e., at least 70%, at least 75%, at least 80%, at least 85%, at least 90%, at least 95%, at least 96%, at least 97%, at least 98%, at least 99% or even 100% identity to the mature enzyme sequences disclosed above.

An acid alpha-amylase may according to the invention be added in an amount of 0.001 to 10 AFAU/g DS, preferably from 0.01 to 5 AFAU/g DS, especially 0.3 to 2 AFAU/g DS or 0.001 to 1 FAU-F/g DS, preferably 0.01 to 1 FAU-F/g DS.

Commercial Alpha-Amylase Products

Preferred commercial compositions comprising alpha-amylase include MYCOLASE™ (DSM), BAN™, TERMAMYL™ SC, FUNGAMYL™, LIQUOZYME™ X, LIQUOZYME™ SC and SAN™ SUPER, SAN™ EXTRA L (Novozymes A/S) and CLARASE™ L-40,000, DEXLO™, SPEZYME™ FRED, SPEZYME™ AA, SPEZYME™ ALPHA, SPEZYME™ DELTA AA, GC358, GC980, SPEZYME™ CL and SPEZYME™ RSL (Danisco A/S), and the acid fungal alpha-amylase from *Aspergillus niger* referred to as SP288 (available from Novozymes A/S, Denmark).

Carbohydrate-Source Generating Enzymes (Saccharifying Enzymes)

The term "carbohydrate-source generating enzyme" includes glucoamylase (a glucose generator), beta-amylase and maltogenic amylase (both maltose generators) and also alpha-glucosidase, isoamylase and pullulanase. A carbohydrate-source generating enzyme is capable of producing a carbohydrate that can be used as an energy-source by the fermenting organism(s) in question, for instance, when used in a process of the invention for producing a fermentation product, such as ethanol. The generated carbohydrate may be converted directly or indirectly to the desired fermentation product, preferably ethanol. According to the invention a mixture of carbohydrate-source generating enzymes may be used. Blends include mixtures comprising at least a glucoamylase and an alpha-amylase, especially an acid amylase, even more preferred an acid fungal alpha-amylase.

The ratio between glucoamylase activity (AGU) and acid fungal alpha-amylase activity (FAU-F) (i.e., AGU per FAU-F) may in a preferred embodiment of the invention be between 0.1 and 100 AGU/FAU-F, in particular between 2 and 50 AGU/FAU-F, such as in the range from 10-40 AGU/FAU-F, especially when performing a one-step fermentation (raw starch hydrolysis—RSH), i.e., when saccharification and fermentation are carried out simultaneously (i.e., without a liquefaction step).

In a conventional starch-to-ethanol process (i.e., including a liquefaction step) the ratio may preferably be as defined in EP 140410, especially when saccharification and fermentation are carried out simultaneously.

Glucoamylases

A glucoamylase may be derived from any suitable source, e.g., derived from a microorganism or a plant. Preferred glucoamylases are of fungal or bacterial origin, selected from the group consisting of *Aspergillus* glucoamylases, in particular *Aspergillus niger* G1 or G2 glucoamylase (Boel et al., 1984, *EMBO J.* 3(5): 1097-1102), or variants thereof, such as those disclosed in WO 92/00381, WO 00/04136 and WO 01/04273 (from Novozymes, Denmark); the *A. awamori* glucoamylase disclosed in WO 84/02921, *Aspergillus oryzae* glucoamylase (Hata et al., 1991, *Agric. Biol. Chem.* 55(4): 941-949), or variants or fragments thereof. Other *Aspergillus* glucoamylase variants include variants with enhanced thermal stability: G137A and G139A (Chen et al., 1996, *Prot. Eng.* 9: 499-505); D257E and D293E/Q (Chen et al., 1995, *Prot. Eng.* 8: 575-582); N182 (Chen et al., 1994, *Biochem. J.* 301: 275-281); disulphide bonds, A246C (Fierobe et al., 1996, *Biochemistry* 35: 8698-8704; and introduction of Pro residues in positions A435 and S436 (Li et al., 1997, *Protein Eng.* 10: 1199-1204.

Other glucoamylases include *Athelia rolfsii* (previously denoted *Corticium rolfsii*) glucoamylase (see U.S. Pat. No. 4,727,026 and Nagasaka et al., 1998, *Appl. Microbiol. Biotechnol.* 50: 323-330), *Talaromyces* glucoamylases, in particular derived from *Talaromyces duponti, Talaromyces emersonii* (WO 99/28448), *Talaromyces leycettanus* (U.S. Pat. No. Re. 32,153), and *Talaromyces thermophilus* (U.S. Pat. No. 4,587,215).

Bacterial glucoamylases include glucoamylases from *Clostridium*, in particular *C. thermoamylolyticum* (EP 135138) and *C. thermohydrosulfuricum* (WO 86/01831), *Trametes cingulata, Pachykytospora papyracea*, and *Leucopaxillus giganteus*, all disclosed in WO 2006/069289; or *Peniophora rufomarginata* disclosed in PCT/US2007/066618; or a mixture thereof. A hybrid glucoamylase may be used in the present invention. Examples of hybrid glucoamylases are disclosed in WO 2005/045018. Specific examples include the hybrid glucoamylase disclosed in Tables 1 and 4 of Example 1 (which hybrids are hereby incorporated by reference).

The glucoamylase may have a high degree of sequence identity to any of above mentioned glucoamylases, i.e., at least 70%, at least 75%, at least 80%, at least 85%, at least 90%, at least 95%, at least 96%, at least 97%, at least 98%, at least 99% or even 100% identity to the mature enzymes sequences mentioned above.

Commercially available glucoamylase compositions include AMG 200L; AMG 300L; SAN™ SUPER, SAN™ EXTRA L, SPIRIZYME™ PLUS, SPIRIZYME™ FUEL, SPIRIZYME™ B4U, SPIRIZYME ULTRA™ and AMG™ E (from Novozymes A/S, Denmark); OPTIDEX™ 300, GC480™ and GC147™ (from Genencor Int., USA); AMIGASE™ and AMIGASE™ PLUS (from DSM); G-ZYME™ G900, G-ZYME™ and G990 ZR (from Genencor Int.).

Glucoamylases may be added in an amount of 0.02-20 AGU/g DS, preferably 0.1-10 AGU/g DS, especially between 1-5 AGU/g DS, such as 0.1-2 AGU/g DS, such as 0.5 AGU/g DS or in an amount of 0.0001-20 AGU/g DS, preferably 0.001-10 AGU/g DS, especially between 0.01-5 AGU/g DS, such as 0.1-2 AGU/g DS.

Beta-amylases

A beta-amylase (E.C 3.2.1.2) is the name traditionally given to exo-acting maltogenic amylases, which catalyze the hydrolysis of 1,4-alpha-glucosidic linkages in amylose, amylopectin and related glucose polymers. Maltose units are successively removed from the non-reducing chain ends in a step-wise manner until the molecule is degraded or, in the case of amylopectin, until a branch point is reached. The maltose released has the beta anomeric configuration, hence the name beta-amylase.

Beta-amylases have been isolated from various plants and microorganisms (Fogarty and Kelly, 1979, *Progress in Industrial Microbiology* 15: 112-115). These beta-amylases are characterized by having a temperature optimum in the range from 40° C. to 65° C. and a pH optimum in the range from 4.5 to 7. A commercially available beta-amylase from barley is NOVOZYM™ WBA from Novozymes A/S, Denmark and SPEZYME™ BBA 1500 from Genencor Int., USA.

Maltogenic Amylases

The amylase may also be a maltogenic alpha-amylase (glucan 1,4-alpha-maltohydrolase, EC 3.2.1.133), which catalyzes the hydrolysis of amylose and amylopectin to maltose in the alpha-configuration. A maltogenic amylase from *Bacillus stearothermophilus* strain NCIB 11837 is commercially available from Novozymes A/S. Maltogenic alpha-amylases are described in U.S. Pat. Nos. 4,598,048, 4,604,355 and 6,162,628, which are hereby incorporated by reference.

The maltogenic amylase may be added in an amount of 0.05-5 mg total protein/gram DS or 0.05-5 MANU/g DS.

Phytases

Any phytase may be used in a process of the present invention. Phytases are enzymes that degrade phytates and/or phytic acid by specifically hydrolyzing the ester link between inositol and phosphorus. Phytase activity is credited with phosphorus and ion availability in many ingredients. In some embodiments, the phytase is capable of liberating at least one inorganic phosphate from an inositol hexaphosphate (e.g., phytic acid). Phytases can be grouped according to their preference for a specific position of the phosphate ester group on the phytate molecule at which hydrolysis is initiated (e.g., 3-phytase (EC 3.1.3.8) or 6-phytase (EC 3.1.3.26)). An example of phytase is myo-inositol-hexakiphosphate-3-phosphohydrolase.

Phytases can be obtained from microorganisms such as fungal and bacterial organisms. For example, the phytase may be obtained from filamentous fungi such as *Aspergillus* (e.g., *A. ficuum, A. fumigatus, A. niger*, and *A. terreus*), *Cladospirum, Mucor* (e.g., *Mucor piriformis*), *Myceliophthora* (e.g., *M. thermophila*), *Penicillium* (e.g., *P. hordei* (ATCC No. 22053)), *P. piceum* (ATCC No. 10519), or *P. brevi-compactum* (ATCC No. 48944), *Talaromyces* (e.g., *T. thermophilus*), *Thermomyces* (WO 99/49740), and *Trichoderma* spp. (e.g., *T. reesei*).

In an embodiment, the phytate-degrading enzyme is obtained from yeast (e.g., *Arxula adeninivorans, Pichia anomala, Schwanniomyces occidentalis*), gram-negative bacteria (e.g., *Escherichia coli, Klebsiella* spp., *Pseudomonas* spp.), and gram-positive bacteria (e.g., *Bacillus* spp. such as *Bacillus subtilis*).

The phytase also may be obtained from *Citrobacter, Enterbacter*, or *Peniophora*.

In an embodiment, the phytase is derived from *Buttiauxiella* spp. such as *B. agrestis, B. brennerae, B. ferragutiase, B. gaviniae, B. izardii, B. noackiae*, and *B. warmboldiae*. In some embodiments, the phytase is a phytase disclosed in WO 2006/043178 or U.S. application Ser. No. 11/714,487.

In one preferred embodiment, the phytase has at least 75%, at least 80%, at least 85%, at least 88%, at least 90%, at least 93%, at least 95%, at least 96%, at least 97%, at least 98% and at least 99% sequence identity to the amino acid sequence set forth in SEQ ID NO: 31 of U.S. application Ser. No. 12/263,886.

Commercially-available phytases are NATUPHOS (BASF), RONOZYME P (Novozymes A/S), PHZYME (Danisco A/S, Diverse) and FINASE (AB Enzymes). The method for determining microbial phytase activity and the definition of a phytase unit is disclosed in Engelen et al., 1994, *Journal of AOAC International* 77: 760-764. The phytase may be a wild-type phytase, an active variant or active fragment thereof.

Pullulanases

Any pullulanase may be used in a process of the present invention. In an embodiment, the pullulanase is a GH57 pullulanase, e.g., a pullulanase obtained from a strain of *Thermococcus*, including *Thermococcus* sp. AM4, *Thermococcus* sp. HJ21, *Thermococcus barophilus, Thermococcus gammatolerans, Thermococcus hydrothermalis; Thermococcus kodakarensis, Thermococcus litoralis*, and *Thermococcus onnurineus*; or from a strain of *Pyrococcus*, such as *Pyrococcus abyssi* and *Pyrococcus furiosus*.

Proteases

A protease may be added during saccharification, fermentation, simultaneous saccharification and fermentation. The protease may be any protease. In a preferred embodiment the protease is an acid protease of microbial origin, preferably of fungal or bacterial origin. An acid fungal protease is preferred, but also other proteases can be used.

Suitable proteases include microbial proteases, such as fungal and bacterial proteases. Preferred proteases are acidic proteases, i.e., proteases characterized by the ability to hydrolyze proteins under acidic conditions below pH 7.

The acid fungal protease may be derived from *Aspergillus, Candida, Coriolus, Endothia, Enthomophtra, Irpex, Mucor, Penicillium, Rhizopus, Sclerotium*, and *Torulopsis*. In particular, the protease may be derived from *Aspergillus aculeatus* (WO 95/02044), *Aspergillus awamori* (Hayashida et al., 1977, *Agric. Biol. Chem.* 42(5), 927-933), *Aspergillus niger* (see, e.g., Koaze et al., 1964, *Agr. Biol. Chem. Japan* 28: 216), *Aspergillus saitoi* (see, e.g., Yoshida, 1954, *J. Agr. Chem. Soc. Japan* 28: 66), or *Aspergillus oryzae*, such as the pepA protease; and acidic proteases from *Mucor miehei* or *Mucor pusiflus*.

The protease may be a neutral or alkaline protease, such as a protease derived from a strain of *Bacillus*. A particular protease is derived from *Bacillus amyloliquefaciens* and has the sequence obtainable at Swissprot as Accession No. P06832. The proteases may have at least 90% sequence identity to the amino acid sequence disclosed in the Swissprot Database, Accession No. P06832 such as at least 92%, at least 95%, at least 96%, at least 97%, at least 98%, or particularly at least 99% identity.

The protease may have at least 90% sequence identity to the amino acid sequence disclosed as SEQ ID NO: 1 in WO 2003/048353 such as at 92%, at least 95%, at least 96%, at least 97%, at least 98%, or particularly at least 99% identity.

The protease may be a papain-like protease selected from the group consisting of proteases within EC 3.4.22.* (cysteine protease), such as EC 3.4.22.2 (papain), EC 3.4.22.6

(chymopapain), EC 3.4.22.7 (asclepain), EC 3.4.22.14 (actinidain), EC 3.4.22.15 (cathepsin L), EC 3.4.22.25 (glycyl endopeptidase) and EC 3.4.22.30 (caricain).

In an embodiment, the protease is a protease preparation derived from a strain of *Aspergillus*, such as *Aspergillus oryzae*. In another embodiment the protease is derived from a strain of *Rhizomucor*, preferably *Rhizomucor miehei*. In another embodiment the protease is a protease preparation, preferably a mixture of a proteolytic preparation derived from a strain of *Aspergillus*, such as *Aspergillus oryzae*, and a protease derived from a strain of *Rhizomucor*, preferably *Rhizomucor miehei*.

Aspartic acid proteases are described in, for example, Handbook of Proteolytic Enzymes, Edited by A. J. Barrett, N. D. Rawlings and J. F. Woessner, Academic Press, San Diego, 1998, Chapter 270. Examples of aspartic acid proteases include, e.g., those disclosed in Berka et al., 1990, *Gene* 96: 313; Berka et al., 1993, *Gene* 125: 195-198; and Gomi et al., 1993, *Biosci. Biotech. Biochem.* 57: 1095-1100, which are hereby incorporated by reference.

The protease also may be a metalloprotease, which is defined as a protease selected from the group consisting of:

(a) proteases belonging to EC 3.4.24 (metalloendopeptidases); preferably EC 3.4.24.39 (acid metallo proteinases);

(b) metalloproteases belonging to the M group of the above Handbook;

(c) metalloproteases not yet assigned to clans (designation: Clan MX), or belonging to either one of clans MA, MB, MC, MD, ME, MF, MG, MH (as defined at pp. 989-991 of the above Handbook);

(d) other families of metalloproteases (as defined at pp. 1448-1452 of the above Handbook);

(e) metalloproteases with a HEXXH motif;

(f) metalloproteases with an HEFTH motif;

(g) metalloproteases belonging to either one of families M3, M26, M27, M32, M34, M35, M36, M41, M43, or M47 (as defined at pp. 1448-1452 of the above Handbook);

(h) metalloproteases belonging to the M28E family; and (i) metalloproteases belonging to family M35 (as defined at pp. 1492-1495 of the above Handbook).

In other particular embodiments, metalloproteases are hydrolases in which the nucleophilic attack on a peptide bond is mediated by a water molecule, which is activated by a divalent metal cation. Examples of divalent cations are zinc, cobalt or manganese. The metal ion may be held in place by amino acid ligands. The number of ligands may be five, four, three, two, one or zero. In a particular embodiment the number is two or three, preferably three.

There are no limitations on the origin of the metalloprotease used in a process of the invention. In an embodiment the metalloprotease is classified as EC 3.4.24, preferably EC 3.4.24.39. In one embodiment, the metalloprotease is an acid-stable metalloprotease, e.g., a fungal acid-stable metalloprotease, such as a metalloprotease derived from a strain of the genus *Thermoascus*, preferably a strain of *Thermoascus aurantiacus*, especially *Thermoascus aurantiacus* CGMCC No. 0670 (classified as EC 3.4.24.39). In another embodiment, the metalloprotease is derived from a strain of the genus *Aspergillus*, preferably a strain of *Aspergillus oryzae*.

In one embodiment the metalloprotease has a degree of sequence identity to amino acids −178 to 177, −159 to 177, or preferably amino acids 1 to 177 (the mature polypeptide) of SEQ ID NO: 1 of WO 2010/008841 (a *Thermoascus aurantiacus* metalloprotease) of at least 80%, at least 82%, at least 85%, at least 90%, at least 95%, or at least 97%; and which have metalloprotease activity. In particular embodiments, the metalloprotease consists of an amino acid sequence with a degree of identity to SEQ ID NO: 1 as mentioned above.

The *Thermoascus aurantiacus* metalloprotease is a preferred example of a metalloprotease suitable for use in a process of the invention. Another metalloprotease is derived from *Aspergillus oryzae* and comprises the sequence of SEQ ID NO: 11 disclosed in WO 2003/048353, or amino acids −23-353; −23-374; −23-397; 1-353; 1-374; 1-397; 177-353; 177-374; or 177-397 thereof, and SEQ ID NO: 10 disclosed in WO 2003/048353.

Another metalloprotease suitable for use in a process of the invention is the *Aspergillus oryzae* metalloprotease comprising SEQ ID NO: 5 of WO 2010/008841, or a metalloprotease is an isolated polypeptide which has a degree of identity to SEQ ID NO: 5 of at least about 80%, at least 82%, at least 85%, at least 90%, at least 95%, or at least 97%; and which have metalloprotease activity. In particular embodiments, the metalloprotease consists of the amino acid sequence of SEQ ID NO: 5.

In a particular embodiment, a metalloprotease has an amino acid sequence that differs by forty, thirty-five, thirty, twenty-five, twenty, or by fifteen amino acids from amino acids −178 to 177, −159 to 177, or +1 to 177 of the amino acid sequences of the *Thermoascus aurantiacus* or *Aspergillus oryzae* metalloprotease.

In another embodiment, a metalloprotease has an amino acid sequence that differs by ten, or by nine, or by eight, or by seven, or by six, or by five amino acids from amino acids −178 to 177, −159 to 177, or +1 to 177 of the amino acid sequences of these metalloproteases, e.g., by four, by three, by two, or by one amino acid.

In particular embodiments, the metalloprotease a) comprises or b) consists of i) the amino acid sequence of amino acids −178 to 177, −159 to 177, or +1 to 177 of SEQ ID NO:1 of WO 2010/008841;

ii) the amino acid sequence of amino acids −23-353, −23-374, −23-397, 1-353, 1-374, 1-397, 177-353, 177-374, or 177-397 of SEQ ID NO: 3 of WO 2010/008841;

iii) the amino acid sequence of SEQ ID NO: 5 of WO 2010/008841; or allelic variants, or fragments, of the sequences of i), ii), and iii) that have protease activity.

A fragment of amino acids −178 to 177, −159 to 177, or +1 to 177 of SEQ ID NO: 1 of WO 2010/008841 or of amino acids −23-353, −23-374, −23-397, 1-353, 1-374, 1-397, 177-353, 177-374, or 177-397 of SEQ ID NO: 3 of WO 2010/008841; is a polypeptide having one or more amino acids deleted from the amino and/or carboxyl terminus of these amino acid sequences. In one embodiment a fragment contains at least 75 amino acid residues, or at least 100 amino acid residues, or at least 125 amino acid residues, or at least 150 amino acid residues, or at least 160 amino acid residues, or at least 165 amino acid residues, or at least 170 amino acid residues, or at least 175 amino acid residues.

In another embodiment, the metalloprotease is combined with another protease, such as a fungal protease, preferably an acid fungal protease.

Commercially available products include ALCALASE®, ESPERASE™ FLAVOURZYME™, NEUTRASE®, RENNILASE®, NOVOZYM™ FM 2.0L, and iZyme BA (available from Novozymes A/S, Denmark) and GC106™ and SPEZYME™ FAN from Genencor International, Inc., USA.

The protease may be present in an amount of 0.0001-1 mg enzyme protein per g DS, preferably 0.001 to 0.1 mg enzyme protein per g DS. Alternatively, the protease may be present in an amount of 0.0001 to 1 LAPU/g DS, preferably 0.001 to 0.1 LAPU/g DS and/or 0.0001 to 1 mAU-RH/g DS, preferably 0.001 to 0.1 mAU-RH/g DS.

Compositions

In this aspect the invention relates to a composition comprising (a) an asparaginase and/or amino acid oxidase, (b) a glucoamylase and (c) an alpha-amylase.

In an embodiment the composition further comprises one or more other carbohydrases, such as alpha-amylases. In a preferred embodiment the alpha-amylase is an acid alpha-amylase or a fungal alpha-amylase, preferably an acid fungal alpha-amylase.

The composition may comprise one or more carbohydrate-source generating enzymes, such as especially glucoamylases, beta-amylases, maltogenic amylases, pullulanases, alpha-glucosidases, or a mixture thereof.

In another preferred embodiment the composition comprises one or more asparaginases and/or amino acid oxidases and one or more fermenting organisms, such as yeast and/or bacteria. Examples of fermenting organisms can be found in the "Fermenting Organism" section above.

Uses

The invention also relates to the use of asparaginase and/or amino acid oxidase in a fermentation process. In an embodiment an asparaginase and/or amino acid oxidase is used for improving the fermentation product yield. In another embodiment, an asparaginase and/or amino acid oxidase is used for increasing growth of the fermenting organism(s).

Modified Fermenting Organism

The invention also relates to a modified fermenting organism transformed with a polynucleotide encoding an asparaginase and/or amino acid oxidase, wherein the fermenting organism is capable of expressing the asparaginase and/or amino acid oxidase at fermentation conditions.

In a preferred embodiment the fermenting organism is a microbial organism, such as yeast or filamentous fungus, or a bacterium. Examples of other fermenting organisms can be found in the "Fermenting Organisms" section.

A fermenting organism may be transformed with a gene encoding an asparaginase and/or an amino acid oxidase using techniques well known in the art.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure, including definitions will be controlling.

Various references are cited herein, the disclosures of which are incorporated by reference in their entireties.

Materials & Methods

Glucoamylase Activity (AGU)

Glucoamylase activity may be measured in Glucoamylase Units (AGU). The Novo Glucoamylase Unit (AGU) is defined as the amount of enzyme, which hydrolyzes 1 micromole maltose per minute under the standard conditions 37° C., pH 4.3, substrate: maltose 23.2 mM, buffer: acetate 0.1 M, reaction time 5 minutes.

An autoanalyzer system may be used. Mutarotase is added to the glucose dehydrogenase reagent so that any alpha-D-glucose present is turned into beta-D-glucose. Glucose dehydrogenase reacts specifically with beta-D-glucose in the reaction mentioned above, forming NADH which is determined using a photometer at 340 nm as a measure of the original glucose concentration.

| AMG incubation: | |
|---|---|
| Substrate: | maltose 23.2 mM |
| Buffer: | acetate 0.1M |
| pH: | 4.30 ± 0.05 |
| Incubation temperature: | 37° C. ± 1 |
| Reaction time: | 5 minutes |
| Enzyme working range: | 0.5-4.0 AGU/mL |
| Color reaction: | |
| GlucDH: | 430 U/L |
| Mutarotase: | 9 U/L |
| NAD: | 0.21 mM |
| Buffer: | phosphate 0.12M; 0.15M NaCl |
| pH: | 7.60 ± 0.05 |
| Incubation temperature: | 37° C. ± 1 |
| Reaction time: | 5 minutes |
| Wavelength: | 340 nm |

Alpha-amylase Activity (KNU)

Alpha-amylase activity may be determined using potato starch as substrate. This method is based on the break-down of modified potato starch by the enzyme, and the reaction is followed by mixing samples of the starch/enzyme solution with an iodine solution. Initially, a blackish-blue color is formed, but during the break-down of the starch the blue color gets weaker and gradually turns into a reddish-brown, which is compared to a colored glass standard.

One Kilo Novo alpha amylase Unit (KNU) is defined as the amount of enzyme which, under standard conditions (i.e., at 37° C.+/−0.05; 0.0003 M $Ca^{2+}$; and pH 5.6) dextrinizes 5260 mg starch dry substance Merck Amylum solubile.

Acid Alpha-amylase Activity (AFAU)

The activity of an acid alpha-amylase may be measured in AFAU (Acid Fungal Alpha-amylase Units) or FAU-F. Acid alpha-amylase activity may be measured in AFAU (Acid Fungal Alpha-amylase Units), which are determined relative to an enzyme standard. 1 AFAU is defined as the amount of enzyme which degrades 5.260 mg starch dry matter per hour under the below mentioned standard conditions.

Acid alpha-amylase, an endo-alpha-amylase (1,4-alpha-D-glucan-glucanohydrolase, EC 3.2.1.1) hydrolyzes alpha-1,4-glucosidic bonds in the inner regions of the starch molecule to form dextrins and oligosaccharides with different chain lengths. The intensity of color formed with iodine is directly proportional to the concentration of starch. Amylase activity is determined using reverse colorimetry as a reduction in the concentration of starch under the specified analytical conditions.

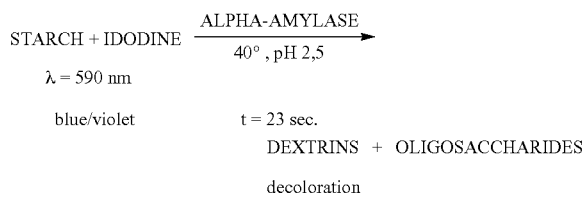

| Standard conditions/reaction conditions: | |
| --- | --- |
| Substrate: | Soluble starch, approx. 0.17 g/L |
| Buffer: | Citrate, approx. 0.03M |
| Iodine ($I_2$): | 0.03 g/L |
| $CaCl_2$: | 1.85 mM |
| pH: | 2.50 ± 0.05 |
| Incubation temperature: | 40° C. |
| Reaction time: | 23 seconds |
| Wavelength: | 590 nm |
| Enzyme concentration: | 0.025 AFAU/mL |
| Enzyme working range: | 0.01-0.04 AFAU/mL |

Determination of FAU-F

FAU-F Fungal Alpha-Amylase Units (Fungamyl) is measured relative to an enzyme standard of a declared strength.

| Reaction conditions | |
| --- | --- |
| Temperature | 37° C. |
| pH | 7.15 |
| Wavelength | 405 nm |
| Reaction time | 5 min |
| Measuring time | 2 min |

Protease Assay Method—AU(RH)

Proteolytic activity may be determined with denatured hemoglobin as substrate. In the Anson-Hemoglobin method for the determination of proteolytic activity denatured hemoglobin is digested, and the undigested hemoglobin is precipitated with trichloroacetic acid (TCA). The amount of TCA soluble product is determined with phenol reagent, which gives a blue color with tyrosine and tryptophan.

One Anson Unit (AU-RH) is defined as the amount of enzyme which under standard conditions (i.e., 25° C., pH 5.5 and 10 minutes reaction time) digests hemoglobin at an initial rate such that there is liberated per minute an amount of TCA soluble product which gives the same color with phenol reagent as one milliequivalent of tyrosine.

The AU(RH) method is described in EAL-SM-0350 and is available from Novozymes A/S Denmark on request.

Protease Assay Method (LAPU)

One Leucine Amino Peptidase Unit (LAPU) is the amount of enzyme which decomposes 1 microM substrate per minute at the following conditions: 26 mM of L-leucine-p-nitroanilide as substrate, 0.1 M Tris buffer (pH 8.0), 37° C., 10 minutes reaction time.

LAPU is described in EB-SM-0298.02/01 available from Novozymes A/S Denmark on request.

Maltogenic Amylase Activity (MANU)

One MANU (Maltogenic Amylase Novo Unit) is the amount of enzyme required to release one micromole of maltose per minute at a concentration of 10 mg of maltotriose (Sigma M 8378) substrate per ml of 0.1 M citrate buffer, pH 5.0 at 37° C. for 30 minutes.

Asparaginase Activity

Stock Solutions 50 mM Tris buffer, pH 8.6

189 mM L-Asparagine solution 1.5 M Trichloroacetic Acid (TCA)

Nessler's reagent, Aldrich Stock No. 34,514-8 (Sigma-Aldrich, St. Louis, Mo. USA)

Asparaginase, Sigma Stock No. A4887 (Sigma-Aldrich, St. Louis, Mo. USA)

Assay

Enzyme Reaction:

500 microliters buffer 100 microliters L-asparagine solution 350 microliters water are mixed and equilibrated to 37° C.

100 microliters of enzyme solution is added and the reactions are incubated at 37° C. for 30 minutes.

The reactions are stopped by placing on ice and adding 50 microliters of 1.5 M TCA.

The samples are mixed and centrifuged for 2 minutes at 20,000×g

Measurement of Free Ammonium:

50 microliters of the enzyme reaction is mixed with 100 microliters of water and 50 microliters of Nessler's reagent. The reaction is mixed and absorbance at 436 nm is measured after 1 minute.

EXAMPLES

Example 1

Use of Asparaginase or Amino Acid Oxidase in a Simultaneous Saccharification and Fermentation Process Corn flour was mixed with tap water in a water bath to achieve a total solids concentration between 30 and 32%. The corn slurry was mixed well to avoid formation of dough balls while raising the temperature to 50° C. Once the corn slurry was heated to 50° C., an asparaginase (500 ppm ACRYLAWAY®/gram dry solids) or a *Bothrops atrox* amino acid oxidase (Sigma A-3016, 12 micromoles/min/mg protein/g) and an alpha-amylase (0.02% LIQUOZYME SODS® (Novozymes)) was added to the corn mash prior to liquefaction. A control was run with alpha-amylase only. The corn mashes were incubated at 50° C. for one hour with continuous mixing. The temperature was elevated to 85° C. and maintained for two hours to allow for optimal starch liquefaction. The liquefied mashes were then cooled to room temperature.

Detection of Maillard Products

To detect the effectiveness of the asparaginase and the amino acid oxidase to reduce Maillard products, samples were collected at the end of liquefaction. These samples were centrifuged at 1942×g for 20 minutes. The supernatants were transferred to microcentrifuge tubes and further centrifuged at 14560×g for 10 minutes. The supernatants were filtered through a 0.45 micron filter, and 200 microliters of the filtered supernatants were pipetted into a microtiter plate well. The fluorescence intensity was measured by exciting the samples with 360 nm wavelength and setting the emissions detection at 460 nm. Fluorescence intensity (FI) measurement was carried out using a Safire model microtiter plate reader with the software XFLUOR4 Version V4.50 (Tecan Co.). The samples were diluted with distilled water to obtain absorption of 0.05 to 0.1 at 460 nm prior to measuring emission.

The fluorescence intensity measured for each sample is provided in Table 1:

| Fluorescence Intensity | | |
| --- | --- | --- |
| Control | Asparaginase | Amino Acid Oxidase |
| 12,250 | 3,750 | 1,125 |

The results show that the use of an asparaginase or amino acid oxidase significantly reduced the amount of Maillard product produced.

Sample Preparation and HLPC Quantification of Ethanol in Corn Fermentations

The cooled, liquefied corn slurries were transferred to fermentation vessels and appropriate amounts of a glucoamylase (SPIRIZYME FUEL®), urea (500 to 1000 ppm) and yeast were added to saccharify the dextrans and ferment the reducing sugars. The simultaneous saccharification and fermentation was carried out at 32° C. to completion 66 hours.

Samples were removed from the fermentations with a wide mouth pipette, and each sample was acidified with 10 microliters of 40% sulfuric acid solution/5 grams of sample to stop the fermentation. The samples were centrifuged for 10 minutes at 1942×g to separate the supernatant and solids. The samples were filtered through a 0.45 micron filter, and ten microliters of the filtered supernatants were analyzed by HPLC using an HPX-787H column (Bio-Rad) heated to 65° C. with a mobile phase of 5 mM sulfuric acid at a flow rate of 0.6 ml/min, with refractive index detection at 50° C.

The amount of ethanol obtained in each fermentation process is provided in Table 2:

TABLE 2

| Control (LIQUOZYME SCDS ®) | LIQUOZYME SODS ® plus ACRYLAWAY ® | LIQUOZYME SODS ® plus amino acid oxidase |
|---|---|---|
| 12.80 +/− 0.05% w/v | 13.50 +/− 0.01% w/v | 13.20 +/− 0.03% w/v |

The results show that that a greater amount of ethanol was produced in a simultaneous saccharification and fermentation process of corn pre-liquefied with Liquozyme SODS® and ACRYLAWAY® or LIQUOZYME SODS® and amino acid oxidase compared to LIQUOZYME SODS® alone.

Example 2

Use of Asparaginase (ACRYLAWAY®) for Ethanol Production from Raw or Clarified Sugarcane Juice Sugarcane juice was incubated for 1 hour at 50° C. with or without 50 ppm ACRYLAWAAY® (v/v).

Detection of Maillard Products

Molasses samples were diluted to 20 Brix with distilled water. The diluted molasses samples were filtered through a 0.45 micron filter, and 200 microliters of the filtered molasses were pipetted into a microtiter plate well. The fluorescence intensity was measured by exciting samples with 360 nm wavelength and set emissions detection at 460 nm. Fluorescence intensity (FI) measurement was carried out using a TECAN Safire model microtiter plate reader with the software XFLUOR4 Version V4.50. The samples were diluted with distilled water to obtain absorption of 0.05 to 0.1 at 460 nm prior to measuring emission.

High levels of Maillard products were detected in all molasses samples screened.

Sugarcane Juice Fermentations

Sugarcane juices obtained from different steps in the industrial process (raw juice, juice clarified for sugar production, and juice clarified for ethanol production) were treated with 50 ppm ACRYLAWAY® at 50° C. for 1 hour and subsequently submitted to an evaporation step in a boiling bath prior to fermentation. Five ml of evaporated samples were transferred in replicates for fermentation to 15 ml flip-cap Nunc centrifuge tubes with holes drilled to release $CO_2$. A 6° Brix solution was prepared from molasses to propagate Red Star yeast: 12 grams of yeast per 80 grams of 6° Brix diluted molasses. Penicillin was added to the solution at 3 mg/L, and the solution was stirred for approximately 16 hours at room temperature. The following morning each fermentation tube containing 5 ml of sample was dosed with 2 ml of yeast propagate and vortexed. Fermentation was carried out at 32° C. for 8 hours. The samples were acidified with 75 microliters of 40% $H_2SO_4$ to stop the fermentation, and subjected to HPLC analysis.

The amount of ethanol obtained in each fermentation process is provided in Table 3:

TABLE 3

| Raw Juice | | Juice Clarified for Sugar Production | | Juice Clarified for Ethanol Production | |
|---|---|---|---|---|---|
| With Asparaginase | Without Asparaginase | With Asparaginase | Without Asparaginase | With Asparaginase | Without Asparaginase |
| 74.5 +/− 0.47 g/l | 72.2 +/− 0.09 g/l | 73.8 +/− 0.25 g/l | 71.7 +/− 0.1 g/l | 75.0 +/− 0.73 g/l | 73.7 +/− 0.58 g/l |

HPLC analysis showed an increased ethanol yield was achieved in each sample treated with an asparaginase.

The present invention is further described in the following numbered paragraphs:

[1]. A process of producing a fermentation product, comprising:
(a) liquefying a starch-containing material to a dextrin with an alpha-amylase in the presence of an amino acid oxidase, an arginase, and/or an asparaginase;
(b) saccharifying the dextrin to a sugar with a saccharifying enzyme; and
(c) fermenting the sugar using a fermenting organism to produce the fermentation product.

[2]. The process of paragraph [1], wherein the starch-containing material is liquefied to the dextrin in the presence of an asparaginase.

[3]. The process of paragraph [2], wherein the asparaginase is an enzyme of EC 3.5.1.1.

[4]. The process of paragraph [2], wherein the asparaginase is an enzyme of EC 3.5.1.38.

[5]. The process of any of paragraphs [1]-[4], wherein the starch-containing material is liquefied to the dextrin in the presence of an arginase.

[6]. The process of any of paragraphs [1]-[5], wherein the starch-containing material is liquefied to the dextrin in the presence of an amino acid oxidase.

[7]. The process of paragraph [6], wherein the amino acid oxidase is an enzyme of EC 1.4.3.2.
[8]. The process of paragraph [6], wherein the amino acid oxidase is an enzyme of EC 1.4.3.3.
[9]. A process of producing a fermentation product, comprising:
(a) treating a starch-containing material with an amino acid oxidase, an arginase, and/or an asparaginase;
(b) liquefying the treated starch-containing material to a dextrin with an alpha-amylase;
(c) saccharifying the dextrin to a sugar with a saccharifying enzyme; and
(d) fermenting the sugar using a fermenting organism to produce the fermentation product.
[10]. The process of paragraph [9], wherein the starch-containing material is treated with an asparaginase at a temperature of 20-75° C., e.g., 25-65° C. or 40-60° C.
[11]. The process of paragraph [10], wherein the asparaginase is an enzyme of EC 3.5.1.1.
[12]. The process of paragraph [10], wherein the asparaginase is an enzyme of EC 3.5.1.38.
[13]. The process of any of paragraphs [9]-[12], wherein the starch-containing material is treated with an arginase at a temperature of 20-75° C., e.g., 25-65° C. or 40-60° C.
[14]. The process of any of paragraphs [9]-[13], wherein the starch-containing material is treated with an amino acid oxidase at a temperature of 20-75° C., e.g., 25-65° C. or 40-60° C.
[15]. The process of paragraph [14], wherein the amino acid oxidase is an enzyme of EC 1.4.3.2.
[16]. The process of paragraph [14], wherein the amino acid oxidase is an enzyme of EC 1.4.3.3.
[17]. The process of any of paragraphs [1]-[16], further comprising recovering the fermentation product.
[18]. A process of producing a sugar, comprising:
(a) liquefying a starch-containing material to a dextrin with an alpha-amylase in the presence of an amino acid oxidase, an arginase, and/or an asparaginase; and
(b) saccharifying the dextrin to a sugar with a saccharifying enzyme.
[19]. The process of paragraph [18], wherein the sugar is maltose.
[20]. The process of paragraph [18], wherein the sugar is glucose.
[21]. The process of paragraph [20], further comprising converting glucose to fructose.
[22]. The process of any of paragraphs [18]-[21], wherein the starch-containing material is liquefied to the dextrin in the presence of an asparaginase.
[23]. The process of paragraph [22], wherein the asparaginase is an enzyme of EC 3.5.1.1.
[24]. The process of paragraph [22], wherein the asparaginase is an enzyme of EC 3.5.1.38.
[25]. The process of any of paragraphs [18]-[24], wherein the starch-containing material is liquefied to the dextrin in the presence of an arginase.
[26]. The process of any of paragraphs [18]-[25], wherein the starch-containing material is liquefied to the dextrin in the presence of an amino acid oxidase.
[27]. The process of paragraph [26], wherein the amino acid oxidase is an enzyme of EC 1.4.3.2.
[28]. The process of paragraph [26], wherein the amino acid oxidase is an enzyme of EC 1.4.3.3.
[29]. A process of producing a sugar, comprising:
(a) treating a starch-containing material with an amino acid oxidase, an arginase, and/or an asparaginase;
(b) liquefying the treated starch-containing material to a dextrin with an alpha-amylase; and
(c) saccharifying the dextrin to a sugar with a saccharifying enzyme.
[30]. The process of paragraph [29], wherein the sugar is maltose.
[31]. The process of paragraph [29], wherein the sugar is glucose.
[32]. The process of paragraph [31], further comprising converting glucose to fructose.
[33]. The process of any of paragraphs [29]-[32], wherein the starch-containing material is treated with an asparaginase at a temperature of 20-75° C., e.g., 25-65° C. or 40-60° C.
[34]. The process of paragraph [33], wherein the asparaginase is an enzyme of EC 3.5.1.1.
[35]. The process of paragraph [33], wherein the asparaginase is an enzyme of EC 3.5.1.38.
[36]. The process of any of paragraphs [29]-[35], wherein the starch-containing material is treated with an arginase at a temperature of 20-75° C., e.g., 25-65° C. or 40-60° C.
[37]. The process of any of paragraphs [29]-[36], wherein the starch-containing material is treated with an amino acid oxidase at a temperature of 20-75° C., e.g., 25-65° C. or 40-60° C.
[38]. The process of paragraph [37], wherein the amino acid oxidase is an enzyme of EC 1.4.3.2.
[39]. The process of paragraph [37], wherein the amino acid oxidase is an enzyme of EC 1.4.3.3.
[40]. The process of any of paragraphs [18]-[39], further comprising recovering the sugar.
[41]. The process of any of paragraphs [21]-[28] and [32]-[40], further comprising recovering the fructose.
[42]. A process of producing a dextrin, comprising
(a) liquefying a starch-containing material to the dextrin with an alpha-amylase in the presence of an amino acid oxidase, an arginase, and/or an asparaginase.
[43]. The process of paragraph [42], wherein the starch-containing material is liquefied to the dextrin in the presence of an asparaginase.
[44]. The process of paragraph [43], wherein the asparaginase is an enzyme of EC 3.5.1.1.
[45]. The process of paragraph [43], wherein the asparaginase is an enzyme of EC 3.5.1.38.
[46]. The process of any of paragraphs [42]-[45], wherein the starch-containing material is liquefied to the dextrin in the presence of an arginase.
[47]. The process of any of paragraphs [42]-[46], wherein the starch-containing material is liquefied to the dextrin in the presence of an amino acid oxidase.
[48]. The process of paragraph [47], wherein the amino acid oxidase is an enzyme of EC 1.4.3.2.
[49]. The process of paragraph [47], wherein the amino acid oxidase is an enzyme of EC 1.4.3.3.
[50]. A process of producing a dextrin, comprising:
(a) treating a starch-containing material with an amino acid oxidase, an arginase, and/or an asparaginase; and
(b) liquefying the treated starch-containing material to a dextrin with an alpha-amylase.
[51]. The process of paragraph [50], wherein the starch-containing material is treated with an asparaginase at a temperature of 20-75° C., e.g., 25-65° C. or 40-60° C.
[52]. The process of paragraph [51], wherein the asparaginase is an enzyme of EC 3.5.1.1.
[53]. The process of paragraph [51], wherein the asparaginase is an enzyme of EC 3.5.1.38.

[54]. The process of any of paragraphs [50]-[53], wherein the starch-containing material is treated with an arginase at a temperature of 20-75° C., e.g., 25-65° C. or 40-60° C.

[55]. The process of any of paragraphs [50]-[54], wherein the starch-containing material is treated with an amino acid oxidase at a temperature of 20-75° C., e.g., 25-65° C. or 40-60° C.

[56]. The process of paragraph [55], wherein the amino acid oxidase is an enzyme of EC 1.4.3.2.

[57]. The process of paragraph [55], wherein the amino acid oxidase is an enzyme of EC 1.4.3.3.

[58]. The process of any of paragraphs [42]-[57], further comprising recovering the dextrin.

[59]. The process of any of paragraphs [1]-[58], wherein the starch-containing material is liquefied to a dextrin at a temperature of 65-110° C., e.g., 80-100° C. or 80-90° C.

[60]. The process of any of paragraphs [1]-[59], wherein the liquefaction comprises jet-cooking at a temperature between 95-140° C.

[61]. The process of any of paragraphs [1]-[41] and 59-60, further comprising pre-saccharification of typically 40-90 minutes at a temperature between 20-75° C., preferably 25-65° C.

[62]. The process of any of paragraphs [1]-[41] and [59]-[61], wherein the saccharification is carried out at a temperature in the range of 20-75° C., preferably 25-65° C.

[63]. The process of any of paragraphs [1]-[41] and [59]-[62], wherein the saccharifying enzyme is a beta-amylase, glucoamylase, or maltogenic alpha-amylase.

[64]. The process of any of paragraphs [1]-[41] and [59]-[63], wherein the dextrin is saccharified to the sugar with a saccharifying enzyme and a pullulanase and/or isoamylase.

[65]. The process of any of paragraphs [1]-[41] and [59]-[64], wherein the saccharification and/or the fermentation are carried out in the presence of a protease.

[66]. The process of any of paragraphs [1]-[41] and [59]-[65], wherein the saccharification and fermentation are performed simultaneously.

[67]. The process of paragraph [66], wherein the saccharification and fermentation are carried out at a temperature of 20-40° C.

[68]. The process of any of paragraphs [1]-[67], wherein the starch-containing material is selected from the group consisting of barley, beans, cassava, cereals, corn, milo, peas, potatoes, rice, rye, sago, sorghum, sweet potatoes, tapioca, wheat, and whole grains, or any mixture thereof.

[69]. A process of producing a fermentation product, comprising converting a starch-containing material to a dextrin with an alpha-amylase; saccharifying the dextrin to a sugar with a glucoamylase; and fermenting the sugar using a fermenting organism in the presence of an amino acid oxidase, an arginase, and/or an asparaginase in a single step at a temperature below the initial gelatinization temperature of the starch-containing material.

[70]. The process of any of paragraphs [1]-[17] and [59]-[69], wherein the fermentation product is selected from the group consisting of alcohols (e.g., butanol, ethanol, methanol, 1,3-propanediol); organic acids (e.g., acetic acid, citric acid, itaconic acid, gluconic acid, gluconate, lactic acid, succinic acid, 2,5-diketo-D-gluconic acid); ketones (e.g., acetone); amino acids (e.g., glutamic acid); gases (e.g., $H_2$ and $CO_2$), and more complex compounds, including, for example, antibiotics (e.g., penicillin and tetracycline); enzymes; vitamins (e.g., riboflavin, $B_{12}$, beta-carotene); and hormones.

[71]. The process of paragraph [70], wherein the fermentation product is ethanol.

[72]. The process of any of paragraphs [1]-[17] and [59]-[71], wherein the fermenting organism is a yeast.

[73]. A process of producing a fermentation product, comprising
(a) treating a plant extract containing amino acid(s) and soluble sugar(s) with an amino acid oxidase, an arginase, and/or an asparaginase;
(b) producing molasses from the treated plant extract;
(c) diluting the molasses; and
(d) fermenting the diluted molasses with a fermenting organism to produce the fermentation product.

[74]. The process of paragraph [73], wherein the plant extract is treated with an asparaginase.

[75]. The process of paragraph [74], wherein the asparaginase is an enzyme of EC 3.5.1.1.

[76]. The process of paragraph [74], wherein the asparaginase is an enzyme of EC 3.5.1.38.

[77]. The process of any of paragraphs [73]-[76], wherein the plant extract is treated with an arginase.

[78]. The process of any of paragraphs [73]-[77], wherein the plant extract is treated with an amino acid oxidase.

[79]. The process of paragraph [78], wherein the amino acid oxidase is an enzyme of EC 1.4.3.2.

[80]. The process of paragraph [78], wherein the amino acid oxidase is an enzyme of EC 1.4.3.3.

[81]. The process of any of paragraphs [73]-[80], wherein the plant extract is raw sugarcane juice or clarified sugarcane juice.

[82]. The process of any of paragraphs [73]-[81], wherein the production of molasses comprises
(x) clarification of the plant extract;
(y) concentration of sugars found in the clarified plant extract (e.g., by evaporation) to form a syrup; and
(z) crystallization of sucrose from the syrup to form the molasses.

[83]. The process of any of paragraphs [73]-[82], wherein step (a) occurs at any time prior to evaporation.

[84]. The process of paragraph [83], wherein step (a) occurs during juice extraction, crushing, juice recovery, and/or juice clarification.

[85]. A process of producing a fermentation product, comprising:
(a) treating a plant extract containing amino acid(s) and soluble sugar(s) with an amino acid oxidase, an arginase, and/or an asparaginase; and
(b) fermenting the treated plant extract with a fermenting organism to produce the fermentation product.

[86]. The process of paragraph [85], wherein the plant extract is treated with an asparaginase.

[87]. The process of paragraph [86], wherein the asparaginase is an enzyme of EC 3.5.1.1.

[88]. The process of paragraph [86], wherein the asparaginase is an enzyme of EC 3.5.1.38.

[89]. The process of any of paragraphs [85]-[88], wherein the plant extract is treated with an arginase.

[90]. The process of any of paragraphs [85]-[89], wherein the plant extract is treated with an amino acid oxidase.

[91]. The process of paragraph [90], wherein the amino acid oxidase is an enzyme of EC 1.4.3.2.

[92]. The process of paragraph [90], wherein the amino acid oxidase is an enzyme of EC 1.4.3.3.

[93]. The process of any of paragraphs [85]-[92], wherein the plant extract is raw sugarcane juice or clarified sugarcane juice.

[94]. The process of any of paragraphs [73]-[93], further comprising recovering the fermentation product.

[95]. The process of any of paragraphs [73]-[94], wherein the fermentation product is selected from the group consisting of alcohols (e.g., butanol, ethanol, methanol, 1,3-propanediol); organic acids (e.g., acetic acid, citric acid, itaconic acid, gluconic acid, gluconate, lactic acid, succinic acid, 2,5-diketo-D-gluconic acid); ketones (e.g., acetone); amino acids (e.g., glutamic acid); gases (e.g., $H_2$ and $CO_2$), and more complex compounds, including, for example, antibiotics (e.g., penicillin and tetracycline); enzymes; vitamins (e.g., riboflavin, $B_{12}$, beta-carotene); and hormones.

[96]. The process of paragraph [95], wherein the fermentation product is ethanol.

[97]. The process of any of paragraphs [73]-[96], wherein the fermenting organism is a yeast.

[98]. A process of producing a sugar, comprising:
(a) treating a plant extract containing amino acid(s) and soluble sugar(s) with an amino acid oxidase, an arginase, and/or an asparaginase; and
(b) recovering the sugar from the plant extract.

[99]. The process of paragraph [98], wherein the sugar is fructose, galactose, glucose, maltose, or sucrose.

[100]. A process of producing sucrose, comprising:
(a) treating a plant extract containing amino acid(s) and soluble sugar(s) with an amino acid oxidase, an arginase, and/or an asparaginase;
(b) clarification of the plant extract;
(c) concentration of sugars found in the clarified plant extract (e.g., by evaporation) to form a syrup containing sucrose;
(d) crystallization of sucrose from the syrup; and
(e) recovering sucrose.

[101]. The process of any of paragraphs [98]-[100], wherein the plant extract is treated with an asparaginase.

[102]. The process of paragraph [101], wherein the asparaginase is an enzyme of EC 3.5.1.1.

[103]. The process of paragraph [101], wherein the asparaginase is an enzyme of EC 3.5.1.38.

[104]. The process of any of paragraphs [98]-[103], wherein the plant extract is treated with an arginase.

[105]. The process of any of paragraphs [98]-[104], wherein the plant extract is treated with an amino acid oxidase.

[106]. The process of paragraph [105], wherein the amino acid oxidase is an enzyme of EC 1.4.3.2.

[107]. The process of paragraph [105], wherein the amino acid oxidase is an enzyme of EC 1.4.3.3.

[108]. The process of any of paragraphs [98]-[107], wherein the plant extract is raw sugarcane juice or clarified sugarcane juice.

[109]. The process of any of paragraphs [98]-[108], wherein step (a) occurs at any time prior to evaporation.

[110]. The process of paragraph [109], wherein step (a) occurs during juice extraction, crushing, juice recovery, and/or juice clarification.

[111]. The process of any of paragraphs [98]-[110], wherein raw sugarcane juice is treated with an asparaginase.

[112]. The process of any of paragraphs [98]-[111], wherein raw sugarcane juice is treated with an arginase.

[113]. The process of any of paragraphs [98]-[112], wherein raw sugarcane juice is treated with an amino acid oxidase.

[114]. The process of any of paragraphs [98]-[113], wherein sugarcane juice clarified for sugar production is treated with an asparaginase.

[115]. The process of any of paragraphs [98]-[114], wherein sugarcane juice clarified for sugar production is treated with an arginase.

[116]. The process of any of paragraphs [98]-[115], wherein sugarcane juice clarified for sugar production is treated with an amino acid oxidase.

[117]. The process of any of paragraphs [98]-[116], wherein sugarcane juice clarified for ethanol production is treated with an asparaginase.

[118]. The process of any of paragraphs [98]-[117], wherein sugarcane juice clarified for ethanol production is treated with an arginase.

[119]. The process of any of paragraphs [98]-[118], wherein sugarcane juice clarified for ethanol production is treated with an amino acid oxidase.

[120]. The process of any of paragraphs [73]-[119], wherein the plant extract is selected from the group consisting of sweet sorghum, sugar beets, sugar cane, or any mixture thereof.

[121]. The process of any of paragraphs [73]-[120], wherein the raw juice is clarified for sugar and/or ethanol production at a pH of 7.5-9, e.g., 8-9.

[122]. The process of any of paragraphs [1]-[121], wherein the asparaginase
(a) has at least 70% sequence identity to SEQ ID NO: 1, e.g., at least 75%, at least 80%, at least 85%, at least 90%, at least 91%, at least 92%, at least 93%, at least 94%, at least 95%, at least 96%, at least 97%, at least 98%, or at least 99% sequence identity; or
(b) is a fragment of SEQ ID NO: 1 that has asparaginase activity.

[123]. The process of any of paragraphs [1]-[121], wherein the asparaginase
(a) has at least 70% sequence identity to SEQ ID NO: 2, e.g., at least 75%, at least 80%, at least 85%, at least 90%, at least 91%, at least 92%, at least 93%, at least 94%, at least 95%, at least 96%, at least 97%, at least 98%, or at least 99% sequence identity; or
(b) is a fragment of SEQ ID NO: 2 that has asparaginase activity.

[124]. The process of any of paragraphs [1]-[121], wherein the asparaginase
(a) has at least 70% sequence identity to SEQ ID NO: 3, e.g., at least 75%, at least 80%, at least 85%, at least 90%, at least 91%, at least 92%, at least 93%, at least 94%, at least 95%, at least 96%, at least 97%, at least 98%, or at least 99% sequence identity; or
(b) is a fragment of SEQ ID NO: 3 that has asparaginase activity.

[125]. The process of any of paragraphs [1]-[121], wherein the asparaginase
(a) has at least 70% sequence identity to SEQ ID NO: 4, e.g., at least 75%, at least 80%, at least 85%, at least 90%, at least 91%, at least 92%, at least 93%, at least 94%, at least 95%, at least 96%, at least 97%, at least 98%, or at least 99% sequence identity; or
(b) is a fragment of SEQ ID NO: 4 that has asparaginase activity.

[126]. The process of any of paragraphs [1]-[121], wherein the asparaginase
(a) has at least 70% sequence identity to SEQ ID NO: 5, e.g., at least 75%, at least 80%, at least 85%, at least 90%, at least 91%, at least 92%, at least 93%, at least 94%, at least 95%, at least 96%, at least 97%, at least 98%, or at least 99% sequence identity; or
(b) is a fragment of SEQ ID NO: 5 that has asparaginase activity.

[127]. The process of any of paragraphs [1]-[121], wherein the asparaginase
(a) has at least 70% sequence identity to SEQ ID NO: 6, e.g., at least 75%, at least 80%, at least 85%, at least 90%, at least 91%, at least 92%, at least 93%, at least 94%, at least 95%, at least 96%, at least 97%, at least 98%, or at least 99% sequence identity; or
(b) is a fragment of SEQ ID NO: 6 that has asparaginase activity.

[128]. The process of any of paragraphs [1]-[121], wherein the asparaginase
(a) has at least 70% sequence identity to SEQ ID NO: 7, e.g., at least 75%, at least 80%, at least 85%, at least 90%, at least 91%, at least 92%, at least 93%, at least 94%, at least 95%, at least 96%, at least 97%, at least 98%, or at least 99% sequence identity; or
(b) is a fragment of SEQ ID NO: 7 that has asparaginase activity.

[129]. The process of any of paragraphs [1]-[121], wherein the asparaginase is a thermostable asparaginase.

[130]. The process of any of paragraphs [1]-[129], wherein the amino acid oxidase
(a) has at least 70% sequence identity to SEQ ID NO: 8, e.g., at least 75%, at least 80%, at least 85%, at least 90%, at least 91%, at least 92%, at least 93%, at least 94%, at least 95%, at least 96%, at least 97%, at least 98%, or at least 99% sequence identity; or
(b) is a fragment of SEQ ID NO: 8 that has amino acid oxidase activity.

[131]. The process of any of paragraphs [1]-[129], wherein the amino acid oxidase
(a) has at least 70% sequence identity to SEQ ID NO: 9, e.g., at least 75%, at least 80%, at least 85%, at least 90%, at least 91%, at least 92%, at least 93%, at least 94%, at least 95%, at least 96%, at least 97%, at least 98%, or at least 99% sequence identity; or
(b) is a fragment of SEQ ID NO: 9 that has amino acid oxidase activity.

[132]. The process of any of paragraphs [1]-[129], wherein the amino acid oxidase
(a) has at least 70% sequence identity to SEQ ID NO: 10, e.g., at least 75%, at least 80%, at least 85%, at least 90%, at least 91%, at least 92%, at least 93%, at least 94%, at least 95%, at least 96%, at least 97%, at least 98%, or at least 99% sequence identity; or
(b) is a fragment of SEQ ID NO: 10 that has amino acid oxidase activity.

[133]. The process of any of paragraphs [1]-[129], wherein the amino acid oxidase
(a) has at least 70% sequence identity to SEQ ID NO: 11, e.g., at least 75%, at least 80%, at least 85%, at least 90%, at least 91%, at least 92%, at least 93%, at least 94%, at least 95%, at least 96%, at least 97%, at least 98%, or at least 99% sequence identity; or
(b) is a fragment of SEQ ID NO: 11 that has amino acid oxidase activity.

[134]. The process of any of paragraphs [1]-[129], wherein the amino acid oxidase
(a) has at least 70% sequence identity to SEQ ID NO: 12, e.g., at least 75%, at least 80%, at least 85%, at least 90%, at least 91%, at least 92%, at least 93%, at least 94%, at least 95%, at least 96%, at least 97%, at least 98%, or at least 99% sequence identity; or
(b) is a fragment of SEQ ID NO: 12 that has amino acid oxidase activity.

[135]. The process of any of paragraphs [1]-[129], wherein the amino acid oxidase
(a) has at least 70% sequence identity to SEQ ID NO: 13, e.g., at least 75%, at least 80%, at least 85%, at least 90%, at least 91%, at least 92%, at least 93%, at least 94%, at least 95%, at least 96%, at least 97%, at least 98%, or at least 99% sequence identity; or
(b) is a fragment of SEQ ID NO: 13 that has amino acid oxidase activity.

[136]. The process of any of paragraphs [1]-[129], wherein the amino acid oxidase
(a) has at least 70% sequence identity to SEQ ID NO: 14, e.g., at least 75%, at least 80%, at least 85%, at least 90%, at least 91%, at least 92%, at least 93%, at least 94%, at least 95%, at least 96%, at least 97%, at least 98%, or at least 99% sequence identity; or
(b) is a fragment of SEQ ID NO: 14 that has amino acid oxidase activity.

[137]. The process of any of paragraphs [1]-[129], wherein the amino acid oxidase is a thermostable amino acid oxidase.

[138]. The process of any of paragraphs [1]-[137], wherein the arginase
(a) has at least 70% sequence identity to SEQ ID NO: 15, e.g., at least 75%, at least 80%, at least 85%, at least 90%, at least 91%, at least 92%, at least 93%, at least 94%, at least 95%, at least 96%, at least 97%, at least 98%, or at least 99% sequence identity; or
(b) is a fragment of SEQ ID NO: 15 that has amino acid oxidase activity.

[139]. The process of any of paragraphs [1]-[137], wherein the arginase
(a) has at least 70% sequence identity to SEQ ID NO: 16, e.g., at least 75%, at least 80%, at least 85%, at least 90%, at least 91%, at least 92%, at least 93%, at least 94%, at least 95%, at least 96%, at least 97%, at least 98%, or at least 99% sequence identity; or
(b) is a fragment of SEQ ID NO: 16 that has amino acid oxidase activity.

[140]. The process of any of paragraphs [1]-[137], wherein the arginase
(a) has at least 70% sequence identity to SEQ ID NO: 17, e.g., at least 75%, at least 80%, at least 85%, at least 90%, at least 91%, at least 92%, at least 93%, at least 94%, at least 95%, at least 96%, at least 97%, at least 98%, or at least 99% sequence identity; or
(b) is a fragment of SEQ ID NO: 17 that has amino acid oxidase activity.

[141]. The process of any of paragraphs [1]-[137], wherein the arginase
(a) has at least 70% sequence identity to SEQ ID NO: 18, e.g., at least 75%, at least 80%, at least 85%, at least 90%, at least 91%, at least 92%, at least 93%, at least 94%, at least 95%, at least 96%, at least 97%, at least 98%, or at least 99% sequence identity; or
(b) is a fragment of SEQ ID NO: 18 that has amino acid oxidase activity.

[142]. The process of any of paragraphs [1]-[137], wherein the arginase
(a) has at least 70% sequence identity to SEQ ID NO: 19, e.g., at least 75%, at least 80%, at least 85%, at least 90%, at least 91%, at least 92%, at least 93%, at least 94%, at least 95%, at least 96%, at least 97%, at least 98%, or at least 99% sequence identity; or
(b) is a fragment of SEQ ID NO: 19 that has amino acid oxidase activity.

[143]. The process of any of paragraphs [1]-[137], wherein the amino acid oxidase is a thermostable arginase.

[144]. A composition comprising (a) an asparaginase, an arginase, and/or amino acid oxidase, (b) a glucoamylase and (c) an alpha-amylase.

[145]. The composition of paragraph [144], which comprises an asparaginase.

146. The composition of paragraph [145], which comprises an asparaginase of EC 3.5.1.1.

[147]. The composition of paragraph [145], which comprises an asparaginase of EC 3.5.1.38.

[148]. The composition of any of paragraphs [144]-[147], which comprises an arginase.

[149]. The composition of any of paragraphs [144]-[148], which comprises an amino acid oxidase.

[150]. The composition of paragraph [149], which comprises an amino acid oxidase of EC 1.4.3.2.

[151]. The composition of paragraph [149], which comprises an amino acid oxidase of EC 1.4.3.3.

[152]. The composition of paragraph [144], which comprises an asparaginase, an arginase, and an amino acid oxidase.

[153]. The composition of paragraph [152], which comprises an asparaginase of EC 3.5.1.1.

[154]. The composition of paragraph [152], which comprises an asparaginase of EC 3.5.1.38.

[155]. The composition of any of paragraphs [152]-[154], which comprises an amino acid oxidase of EC 1.4.3.2.

[156]. The composition of any of paragraphs [152]-[154], which comprises an amino acid oxidase of EC 1.4.3.3.

[157]. The composition of any of paragraphs [144]-[156], further comprising a pullulanase.

---

The invention claimed is:

1. A process of producing a fermentation product, comprising
   (a) treating a plant extract containing amino acid(s) and soluble sugar(s) with an amino acid oxidase, an arginase, and/or an asparaginase;
   (b) producing molasses from the treated plant extract;
   (c) diluting the molasses; and
   (d) fermenting the diluted molasses with a fermenting organism to produce the fermentation product.

2. The process of claim 1, wherein the plant extract is treated with an asparaginase.

3. The process of claim 2, wherein the asparaginase is an enzyme of EC 3.5.1.1.

4. The process of claim 2, wherein the asparaginase is an enzyme of EC 3.5.1.38.

5. The process of claim 1, wherein the plant extract is treated with an arginase.

6. The process of claim 1, wherein the plant extract is treated with an amino acid oxidase.

7. The process of claim 6, wherein the amino acid oxidase is an enzyme of EC 1.4.3.2.

8. The process of claim 6, wherein the amino acid oxidase is an enzyme of EC 1.4.3.3.

9. The process of claim 1, wherein the plant extract is raw sugarcane juice or clarified sugarcane juice.

10. The process of claim 1, wherein the production of molasses comprises:
    clarification of the plant extract;
    concentration of sugars found in the clarified plant extract to form a syrup; and
    crystallization of sucrose from the syrup to form the molasses.

11. A process of producing a fermentation product, comprising
    (a) treating a plant extract containing amino acid(s) and soluble sugar(s) with an amino acid oxidase, an arginase, and/or an asparaginase;
    (b) producing molasses from the treated plant extract;
    (c) diluting the molasses; and
    (d) fermenting the diluted molasses with a fermenting organism to produce the fermentation product, wherein the plant extract is selected from the group consisting of sweet sorghum extract, sugar beet extract, sugar cane extract, sugar cane juice, clarified sugarcane juice, and combinations thereof.

12. The process of claim 11, wherein the plant extract is treated with an asparaginase.

13. The process of claim 11, wherein the asparaginase is an enzyme of EC 3.5.1.1.

14. The process of claim 11, wherein the asparaginase is an enzyme of EC 3.5.1.38.

15. The process of claim 11, wherein the plant extract is treated with an arginase.

16. The process of claim 11, wherein the plant extract is treated with an amino acid oxidase.

17. The process of claim 11, wherein the plant extract is treated with an arginase.

18. The process of claim 11, wherein the plant extract is treated with an amino acid oxidase.

* * * * *